(12) United States Patent
Nagamatsu et al.

(10) Patent No.: US 11,806,351 B2
(45) Date of Patent: Nov. 7, 2023

(54) USE OF COENZYME FACTOR FOR ACTIVATION OF ATP PRODUCTION IN CELL

(71) Applicant: TERA STONE Co., Ltd, Kanagawa (JP)

(72) Inventors: Tomohisa Nagamatsu, Kumamoto (JP); Norio Akaike, Kumamoto (JP)

(73) Assignee: TERA STONE Co., Ltd, Kanagawa (JP)

( * ) Notice: Subject to any disclaimer, the term of this patent is extended or adjusted under 35 U.S.C. 154(b) by 0 days.

(21) Appl. No.: 17/738,027

(22) Filed: May 6, 2022

(65) Prior Publication Data

US 2022/0265662 A1     Aug. 25, 2022

Related U.S. Application Data

(62) Division of application No. 16/637,280, filed as application No. PCT/JP2019/003860 on Feb. 4, 2019, now Pat. No. 11,439,644.

(30) Foreign Application Priority Data

Feb. 5, 2018   (JP) .................................. 2018-018388
Jan. 23, 2019  (JP) .................................. 2019-009224

(51) Int. Cl.
    *A61K 31/519*   (2006.01)
    *A61K 31/58*    (2006.01)
    *A61P 25/28*    (2006.01)

(52) U.S. Cl.
    CPC ............ *A61K 31/519* (2013.01); *A61K 31/58* (2013.01); *A61P 25/28* (2018.01)

(58) Field of Classification Search
    CPC ....... A61K 31/519; A61K 31/58; A61P 25/24; A61P 25/28; A61P 43/00
    See application file for complete search history.

(56) References Cited

FOREIGN PATENT DOCUMENTS

JP         2005104868 A   *   4/2005

OTHER PUBLICATIONS

Nagamatsu, JP 2005-104868, English translation, Apr. 21, 2005 (Year: 2005).*

Shrestha et. al., Bioorganic & Med. Chemistry, vol. 16, pp. 8685-8696, publ. 2008 (Year: 2008).*
Office Action of China Counterpart Application, with English translation thereof, dated Feb. 24, 2023, pp. 1-19.
"Office Action of Taiwan Counterpart Application", dated Jul. 4, 2022, with English translation thereof, p. 1-p. 10.
Hamed I Ali et al., "Antitumor studies. Part 1: Design, synthesis, antitumor activity, and AutoDock study of 2-deoxo-2-phenyl-5-deazaflavins and 2-deoxo-2-phenylflavin-5-oxides as a new class of antitumor agents," Bioorganic & Medicinal Chemistry, vol. 15, Jan. 2007, pp. 1-29.
Nagamatsu Tomohisa, "Molecular design and enzyme inhibition mode using software supported by computer for antitumor active flavin derivatives," May 2011, Available at: https://kaken.nii.ac.jp/file/KAKENHI-PROJECT-20590102/20590102seika.pdf.

* cited by examiner

*Primary Examiner* — Sarah Pihonak
(74) *Attorney, Agent, or Firm* — JCIP GLOBAL INC.

(57) ABSTRACT

Problem: to provide an activator for activating intracellular ATP production. Solution: use of deazaflavino-testosterone compound represented by the following formula (III):

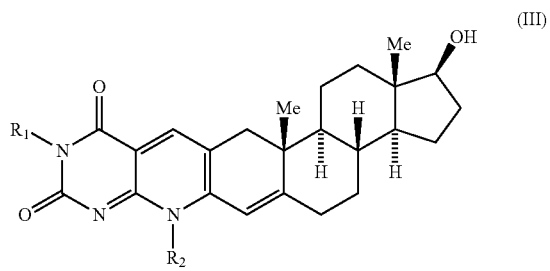

wherein, $R_1$ represents a hydrogen atom, an alkyl group, a halogen-substituted alkyl group, a carboxy-substituted alkyl group, a phenyl group, or a phenyl group substituted by one of a halogen atom, a lower alkyl group, or a lower alkoxy group and $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group for activating intracellular ATP production,
    the use comprising introducing said deazaflavino-testosterone compound to a human-derived neuron cells, wherein said deazaflavino-testosterone compound is used as a coenzyme factor effective for activating intracellular ATP production.

2 Claims, 28 Drawing Sheets

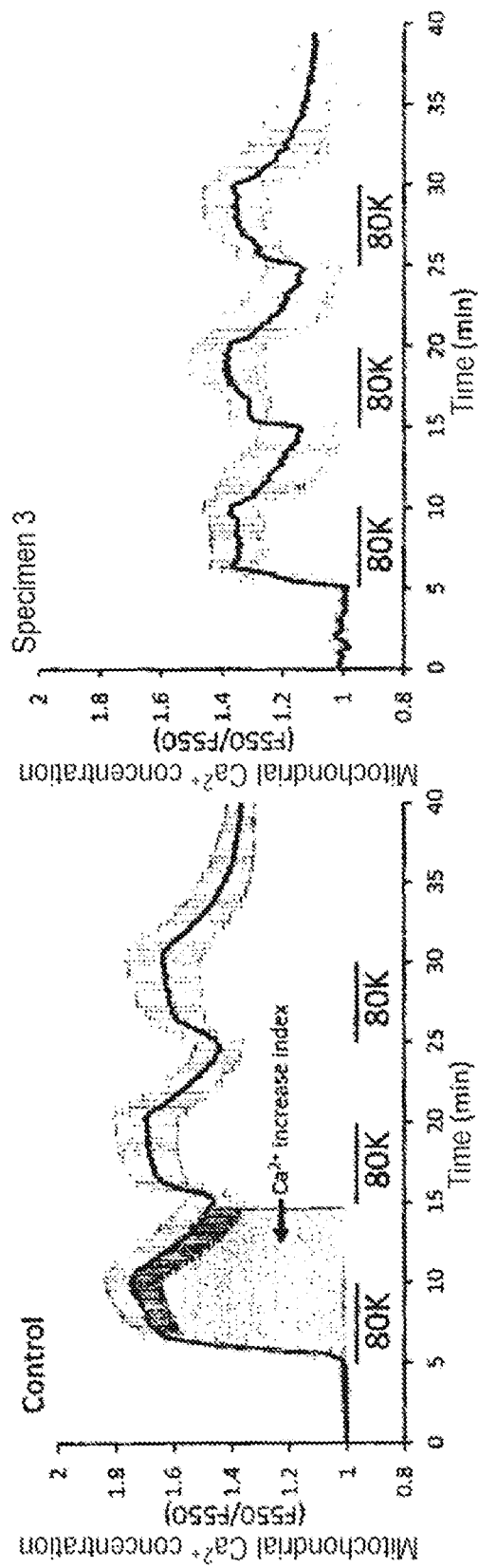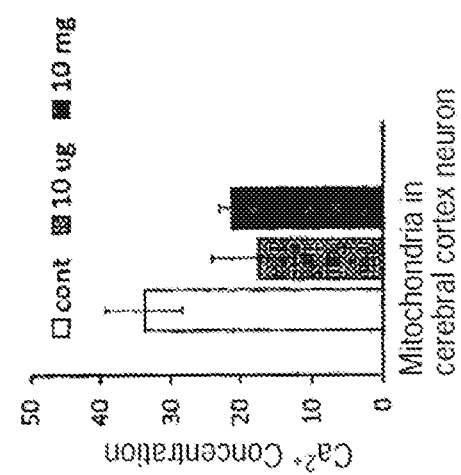
FIG. 12A  FIG. 12B  FIG. 12C

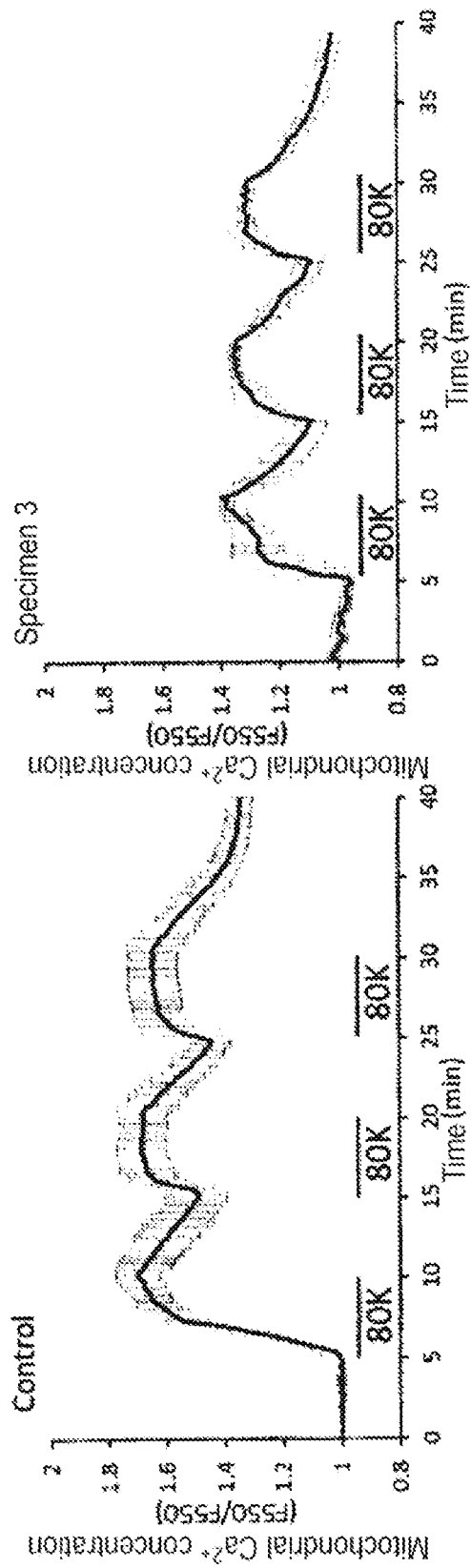
FIG. 13B
FIG. 13A
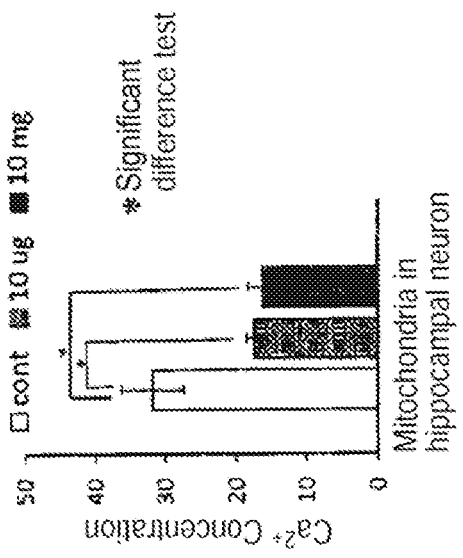
FIG. 13C

Rat exercise footprints in Box measured with video camera

USE OF COENZYME FACTOR FOR ACTIVATION OF ATP PRODUCTION IN CELL

CROSS-REFERENCE TO RELATED APPLICATION

This is a divisional application of patent application Ser. No. 16/637,280, filed on Feb. 7, 2020, wherein the patent application Ser. No. 16/637,280 is a 371 application of the international PCT application serial no. PCT/JP2019/003860, filed on Feb. 4, 2019, which claims the priority benefit of Japan application no. 2018-018388, filed on Feb. 5, 2018, and Japan application no. 2019-009224, filed on Jan. 23, 2019. The entirety of each of the above-mentioned patent applications is hereby incorporated by reference herein and made a part of this specification.

TECHNICAL FIELD

The present invention relates to use of a coenzyme factor for activating intracellular ATP production, more specifically, use of a coenzyme factor that assists a redox enzyme involved in ATP production.

BACKGROUND ART

Neurodegenerative diseases and depression that accompany Alzheimer's disease, Parkinson disease, or cerebral hemorrhage/infarction have shown a drastic increase with the coming of an aging society in recent years and there is increasingly a demand for preventive/remedy of these neurodegenerative diseases.

One of the onset factors of the above-described diseases is the dysfunction of energy production (ATP production) in cells. ATP production occurs in the cytoplasmic matrix, but occurs mainly in the mitochondrial complex under aerobic conditions. Mitochondria are present in all the animal cells and are involved in energy production necessary for the activities of cells via an electron transport system. Since mitochondria and mitochondrial genes are vulnerable to oxidative stress caused by abnormal electron transport, they will result in lower energy metabolism and cell degeneration. Particularly in brain cells requiring a high energy amount, mitochondria are more susceptible to denaturation so that so-called "brain mitochondrial dysfunctions" due to mitochondrial abnormal electron transport that accompanies aging is caused.

On the other hand, a recent research suggests that retardation of aging and prolongation of the lifespan of organisms can be achieved by the activation of Sirtuin genes (Non-Patent Document 1).

A study on the relation between sirtuin genes and mitochondria has proceeded and it suggests that with the activation of sirtuin genes, mitochondria which are intracellular organelles increase in their amount and are activated further not only to promote prevention of dementia, prevention of arteriosclerosis, prevention of hearing impairment, fat combustion, cellular repair, and removal of active oxygen and thereby suppress expression of aging factors but also to provide an effect for curing mitochondrial dysfunctions (Non-Patent Document 2).

For example, the research team of The University of Massachusetts found a memory disorder from mice whose SIRT1 gene, one of sirtuin genes, had been knocked out and advocated the possibility of the present gene participating in memory. Further, the team suggested application of SIRT1 gene activation to the therapy of neurodegenerative diseases by using animal models of Alzheimer's disease and amyotrophic lateral sclerosis. In 2008, on the other hand, Shin-ichiro Imai, a professor of Washington University School of Medicine, identified NMN (Nicotinamide mononucleotide) as a substance controlling the human aging and also succeeded in use of NMN for the reactivation of islets of Langerhans which had once been inactivated with aging. It has been revealed that NMN activates all the genes and vitalizes mitochondria (Non-Patent Document 3).

It has also been revealed that SIRT2, one of longevity protein sirtuin genes discovered by Prof. Imai, et al., is a heterochromatin component that silences transcription at telomeres and the ribosomal DNA and is an NAD-dependent histone deacetylase. This enzyme serves to restore binding of DNA to histones, which has once been weakened by acetylation, by deacetylation, enhance wrapping of DNA around histones, and thereby suppress transcription, which is presumed to be associated with longevity (Non-Patent Document 4).

Suggesting the possibility that a biosynthesis promoter of $NAD^+$ (Nicotinamide Adenine Dinucleotide), an activation factor of the enzyme, has an antiaging effect, Prof. Imai, et al. have reported the possibility that NMN, an intermediate substance for $NAD^+$ synthesis, promotes biosynthesis of $NAD^+$ and this is associated with an antiaging effect (Non-Patent Document 5).

Further, Mills, et al. have reported that long-term administration of a diet comprising NMN to mice enhances $NAD^+$ production in the tissue and can mitigate age-associated physiological dysfunction of individuals (Non-Patent Document 6).

This can be understood from the fact that $NAD^+$ is one of the most important molecules in energy production which is associated with the first stage of oxidative phosphorylation in mitochondria and an oxidation reaction in the TCA cycle.

It is known, on the other hand, that SIRT1, one of longevity protein sirtuin genes, is mainly associated with repair/regeneration of mitochondria that have been injured, though expressed in nuclei. Further, it has been revealed that SIRT3, SIRT4, and SIRT5, of seven mammalian sirtuin genes that have already been discovered, are expressed mainly in mitochondria (Non-Patent Documents 7 and 8).

It is presumed comprehensively based on these results that various sirtuin genes are associated with a lifespan extending effect via activation of mitochondrial function (Non-Patent Document 9).

In mitochondria when normal, NMN (a precursor compound of $NAD^+$ (nicotine amide adenine dinucleotide) is always produced continuously, but when aged or sick, its production amount decreases, leading to a decrease in $NAD^+$. As a result, it causes a reduction in ATP (adenosine triphosphate), a life support energy source produced by oxidative phosphorylation in mitochondria through an electron transport chain or a glycolytic pathway in the cytoplasmic matrix (Non-Patent Document 10). NADH (Dihydro-nicotinamide adenine dinucleotide), a reduced form of $NAD^+$, or $FADH_2$ (Dihydro-flavin adenine dinucleotide) functions as a coenzyme in the TCA (citric acid) circuit of the intramitochondrial matrix or the cytoplasmic glycolytic pathway.

NAD (nicotinamide adenine dinucleotide) is one of coenzymes associated with a redox enzyme and its reduced form, NADH, is a coenzyme most abundantly present in the body.

NAD has a structure in which nicotinamide mononucleotide (NMN) and adenylic acid constitute a phosphodiester bond. Since the nitrogen atom of the pyridine ring in NAD, the oxidized form, is present as a pyridium ion, it is expressed as "$NAD^+$". The important function of $NAD^+$ resides in that the reduction of $NAD^+$ is conjugated with an ATP production mechanism (oxidation reaction).

FAD (Flavin adenine dinucleotide) is a coenzyme also associated with a redox enzyme and $FADH_2$, a reduced form thereof, is used for ATP production in the mitochondrial electron transport chain.

A primary supply destination of FAD in the metabolism of eukaryotic organisms is the intramitochondrial citric acid circuit and the cytoplasmic matrix where B oxidation is performed. In the citric acid circuit, FAD functions as a coenzyme of succinate dehydrogenase that oxidizes succinic acid into fumaric acid, while in the B oxidation, it functions as a coenzyme for the enzymatic reaction of acyl CoA dehydrogenase. It is however presumed to be difficult to develop NMN or $NAD^+$ belonging to a redox (reduction oxidation) type as a pharmaceutical in future, because it is easily decomposed in the metabolic system and in addition, is chemically instable. Moreover, synthesis of it costs high.

There is therefore an eager demand for the development of a chemical fully satisfactory as a pharmaceutical from the viewpoint that it has an excellent effect for activating the ATP production function and shows excellent pharmacokinetics (biological absorption, intracerebral migration, and the like).

The present inventors have proceeded with an extensive investigation on the synthesis of a compound having a flavin skeleton and a pharmacological effect thereof for years. A 5-deazaflavin (pyrimido[4,5-b]quinoline-2,4(3H,10H)-dione) derivative obtained by substituting N at position 5 of riboflavin with CH and having a special chemical structure is a compound synthesized for the first time as a riboflavin analog in 1970. Some of 5-deazaflavin derivatives are known to show excellent antitumor activity or have anti-herpesvirus activity and some of them are used as an antitumor agent or an anti-herpesvirus agent (Patent Documents 1 to 5).

The derivatives have also been studied in terms of a catalytic function for a conversion reaction of an alcohol into ketone or aldehyde that occurs with the change of the structure of the compound, a conversion reaction from amine to imine (ketone), reduction of a carbonyl compound into an alcohol, reduction or asymmetric reduction of an imine to an amine, and similarly to $NAD^+$ (nicotinamide nucleotide) (Non-Patent Document 11). Various patent documents describing them as a mitochondrial function activator have been published (Patent Documents 6 to 8). A document paying attention to redox catalytic activity of the 5-deazaflavin derivatives and applying it to a mitochondrial function activating effect has not yet been found. It is obvious that since 5-deazaflavin derivatives have redox catalytic activity, they have an influence on the ATP production function in mitochondrial oxidative phosphorylation. The 5-deazaflavin skeleton is found in a coenzyme $F_{420}$ (Coenzyme $F_{420}$) which is a coenzyme associated with a redox reaction of methane fermentation and it is also a flavin analog. Its redox behavior is more similar to that of $NAD(P)^+$ than to that of flavin. One of the resonance canonical formulas of it includes, in the molecule thereof, a $NAD(P)^+$ structure and it can be regarded as a "flavin type $NAD(P)^+$" also from the electron density (determined by molecular orbital computational chemistry).

The present inventors have carried out an extensive investigation, considering that since 5-deazaflavins have a redox (oxidation and reduction) function similar to that of $NAD^+$ or FAD, they activate intracellular ATP production and further, directly or indirectly activate sirtuin genes. As a result, it has been found that a 5-deazaflavin compound having a certain structural formula is very chemically stable, can be synthesized at a low cost, activates ATP production, and activates sirtuin genes that control the mitochondrial function, leading to the completion of the present invention.

CITATION LIST

Patent Documents

Patent Document 1: Japanese Patent No. 3073309
Patent Document 2: Japanese Patent Application Laid-Open No. H6-199857
Patent Document 3: Japanese Patent Application Laid-Open No. H11-322746
Patent Document 4: Japanese Patent Application Laid-Open No. 2000-212087
Patent Document 5: Japanese Patent Application Laid-Open No. H6-73058
Patent Document 6: Japanese Patent Application Laid-Open No. 2001-48784
Patent Document 7: Japanese Patent Application Laid-Open No. 2002-322058
Patent Document 8: Japanese Patent Application Laid-Open No. 2008-255059

Non-Patent Documents

Non-Patent Document 1: 140. Mitochondrial control for antiaging, Research reports of The Uehara Memorial Foundation, 25 (2011).
Non-Patent Document 2: Elucidation of metabolic control mechanism of SIRT1.
Non-Patent Document 3: Body function recovery and prolongation of healthy lifespan—Unexpected effect of a substance "NMN" clarified by the research of aging and lifespan.
Non-Patent Document 4: Imai S1, Armstrong C M, Kaeberlein M, Guarente L(2000), Transcriptional silencing and longevity protein Sir2 is an NAD-dependent histone deacetylase. Nature. 403(6771):795-800.
Non-Patent Document 5: Imai (2010) A possibility of nutriceuticals as an anti-aging intervention: activation of sirtuins by promoting mammalian NAD biosynthesis. Pharmacol Res. 62(1):42-7.
Non-Patent Document 6: Mills K F, Yoshida S, Stein L R, Grozio A, Kubota S, Sasaki Y, Redpath P, Migaud M E, Apte R S, Uchida K, Yoshino J, Imai S I (2016) Long-Term Administration of Nicotinamide Mononucleotide Mitigates Age-Associated Physiological Decline in Mice. Cell Metab. 24(6):795-806.
Non-Patent Document 7: Michishita E1, Park J Y, Burneskis J M, Barrett J C, Horikawa I. (2005) Evolutionarily conserved and nonconserved cellular localizations and functions of human SIRT proteins. Mol Biol Cell. Oct; 16(10):4623-35.
Non-Patent Document 8: Pacholec M, Bleasdale J E, Chrunyk B, Cunningham D, Flynn D, Garofalo R S, Griffith D, Griffor M, Loulakis P, Pabst B, Qiu X, Stockman B, Thanabal V, Varghese A, Ward J, Withka J, Ahn K. (2010) SRT1720, SRT2183, SRT1460, and resveratrol are not direct activators of SIRT1. J Biol Chem. 285(11):8340-51.
Non-Patent Document 9: Tang BL(2016) Sirt1 and the Mitochondria Mol. Cells 39(2):87-95.

Non-Patent Document 10: The pathophysiological importance and therapeutic potential of NAD+ biosynthesis in age-related diseases.

Non-Patent Document 11: "Synthesis of heterocyclic compound having redox functionality".

An object of the present invention is to provide a 5-deazaflavin compound selected from various 5-deazaflavin derivatives and having a structural formula effective for activating intracellular ATP production.

Means for Solving the Problems

With a view to achieving the above-described object, the present inventors carried out an extensive investigation, prepared various 5-deazaflavin derivative compounds having respectively different structural formulas as a specimen, and repeated various experiments in vitro with those compounds. As a result, they have found a compound having a structural formula capable of increasing intracellular ATP production.

First, the present inventors payed attention to, as an analog of NMN (refer to FIG. 17), 5-deazaflavin obtained by substituting, by a methylene group, nitrogen at position 5 of the flavin skeleton of riboflavin (Vitamin $B_2$) known as a growth factor and being a water-soluble vitamin. 5-Deazariboflavin was metabolically antagonistic to riboflavin and showed strong anti-coccidium activity. A coenzyme $F_{420}$ (refer to FIG. 18. Redox coenzyme Factor 420($F_{420}$). Discovered from methanogen Coenzyme $F_{420}$ plays an important role in reduction process from carbon dioxide gas to methane or in biosynthesis process of antibiotic. L. D. Eirich, G. D. Vogels, and R. S. Wolfe, Biochemistry, 17, 4583(1978). R. P. Hausinger, W. H. Orme-Johnson, and C. Walsh, Biochemistry, 24, 1629(1985).) having a 5-deazaflavin skeleton has recently been found from a methanogen and known to have an important role in the reduction process of a carbon dioxide gas into methane or the biosynthesis process of an antibiotic. The redox behavior of 5-deazaflavin is similar to that of NAD(P)+ (refer to FIG. 19. Structure of the oxidized form of nicotinamide adenine dinucleotide (NAD+) and nicotinamide adenine dinucleotide phosphate (NADP+). Redox of NAD(P+).) rather than that of flavin. One of the resonance canonical formulas includes, in the molecule thereof, a NAD(P)+ structure and it can be regarded as a "flavin type NAD(P)+" also from the electron density (determined by molecular orbital computational chemistry) (refer to FIG. 20). Huckel MO calculation has revealed that a 5-deazaflavin ring is much deficient, at position 5 thereof, in n electrons (net charge: +0.24) and also nicotinamide nucleotide is similarly deficient, at position 4 thereof, in n electrons (net charge: +0.210). The 5-deazaflavin ring is therefore presumed to belong to both NAD(+) and FAD (refer to FIG. 21. Structure and name of FLAVIN COENZYME) electron transport chains. Nicotinamide adenine dinucleotide (NAD) is an electron transporter used in all the eukaryotic organisms and many archaebacterial and eubacteria.

In fact, fluorescent labeling for mitochondrial membrane potential by MitoTracker fluorescent staining showed that treatment with a novel NMN analog (5-deazaflavin) markedly promoted mitochondrial activity. It is presumed that activation of sirtuin genes activates intracellular organelles "mitochondria", promotes prevention of dementia, prevention of arteriosclerosis, prevention of hearing impairment, fat combustion, cellular repair, and removal of active oxygen harmful for genes, and thereby has an effect for suppressing the expression of aging factors. Compared with β-NMN, 5-deazaflavin serving as an electron transport chains switches on and activates sirtuin genes which are longevity genes at a low dose and at the same time, promotes ATP production by the activation of mitochondria.

The present inventors have presumed that compared with β-NMN whose use is under investigation as a pharmaceutical capable of supplementing NMN, this 5-deazaflavin compound having a redox function similar to that of NAD+ or FAD is very chemically stable and can be synthesized at a low cost, activates NAD+, and directly or indirectly activates the longevity genes (SIRT1 and SIRT3) of mitochondria. In other words, for the purpose of evaluating the activation of the longevity gene SIRT1 which is NAD+ dependently activated and has already been known as a gene important for the maintenance of mitochondrial function, the present inventors carried out screening evaluation of an mRNA increase via q-RT-PCR using HCT116 cells, with the expression of FOX01, a target transcription factor of SIRT1, as an activity index.

As a result, they have revealed that compared with β-NMN, the compounds of the present invention have a SIRT1 activating ability at a less dose. The compounds of the present invention are therefore expected to directly activate NAD+, produce ATP continuously even under pathologic conditions such as ischemia, and thus have a continuous and powerful effect. The compounds of the present invention are therefore presumed to sufficiently have necessary conditions for the development of them as a pharmaceutical. In addition, they have a chemical structure close to an integrated structure of the core portions of the coenzymes NAD+ and FAD from the viewpoints of function and electron theory, in other words, close to a structure present in the natural world as a hybrid of nicotinamide and flavin, so that they are presumed to produce almost no side effects. Further, the structure of the compounds of the present invention have a redox potential higher than that of NAD or FAD as a coenzyme and are excellent in redox ability judging from the measured value of their redox potential.

The present invention has been completed based on the above findings.

Described specifically, the present invention identifies compounds represented by the following formulas (I) to (IV) as a coenzyme factor effective for activating intracellular ATP production.

Chemical formula 1

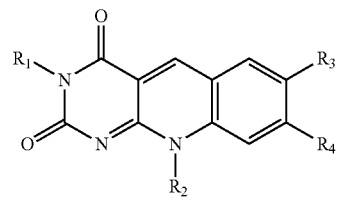

(I)

5-Deazaflavins (Pyrimido[4,5-b]quinoline-2,4 (3H,10H)-diones)

(wherein, $R_1$ represents a hydrogen atom, an alkyl group, a halogen-substituted alkyl group, a carboxy-substituted alkyl group, or a phenyl group, $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group, and $R_3$ and $R_4$ each represent a hydrogen atom, a lower alkyl group, a halogen atom, a hydroxyl group, a nitro group, a cyano group, a lower alkoxy group, a phenyl-substituted lower alkoxy, a lower alkylamino group, a phenyl-substituted lower alkylamino group, or a lower alkylsulfonyl group).

Chemical formula 2

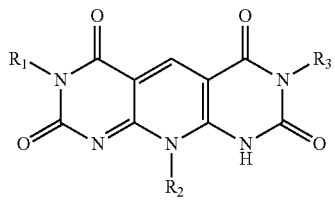

(II)

Pyridodipyrimidines (Pyrido [2,3-d:6,5-d'] dipyrimidine-2,4,6,8(1H,3H,7H,10H)-tetraones)

(wherein, $R_1$ and $R_3$ each represent a hydrogen atom, an alkyl group, a halogen-substituted alkyl group, a carboxy-substituted alkyl group, a phenyl group, a phenyl group substituted by one of a halogen atom, a lower alkyl group, or a lower alkoxy group, or a lower alkyl disubstituted phenyl group and $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group).

Chemical formula 3

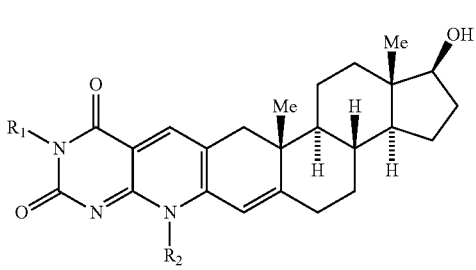

(III)

Deazaflavino-testosterones
(3',8'-Disubstitued 5'-deaza-17β-hydroxyandrost-2,4-dieno[2,3-g]pteridine-2,4'(3'H,8'H)-diones)

(wherein, $R_1$ represents a hydrogen atom, an alkyl group, a halogen-substituted alkyl group, a carboxy-substituted alkyl group, a phenyl group, or a phenyl group substituted by one of a halogen atom, a lower alkyl group, or a lower alkoxy group and $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group).

Chemical formula 4

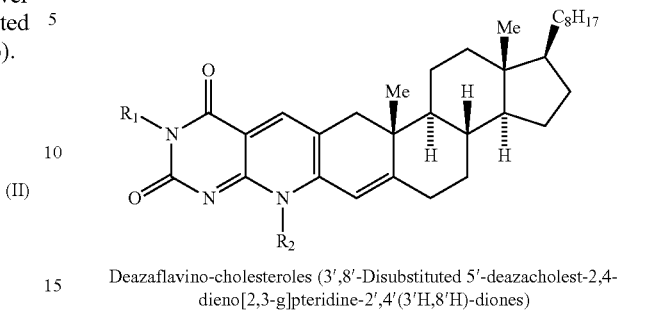

(IV)

Deazaflavino-cholesteroles (3',8'-Disubstituted 5'-deazacholest-2,4-dieno[2,3-g]pteridine-2',4'(3'H,8'H)-diones)

(wherein, $R_1$ represents a hydrogen atom, an alkyl group, a halogen-substituted alkyl group, a carboxy-substituted alkyl group, a phenyl group, or a phenyl group substituted by one of a halogen atom, a lower alkyl group, or a lower alkoxy group and $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group).

Advantageous Effect of the Invention

Using a coenzyme factor provided by the present invention and capable of activating ATP production can improve the dysfunction of energy production in cells.

It is therefore extremely useful as a preventive/remedy for neurodegenerative diseases and depression that accompany Alzheimer's diseases, Parkinson's diseases, cerebral hemorrhage/infarction, or the like.

BRIEF DESCRIPTION OF THE DRAWINGS

FIG. 12A to FIG. 12C show the measurement of a $K^+$ depolarization-induced $Ca^{2+}$ concentration increase in mitochondria present in cerebral cortex neurons (neurons) and an inhibitory effect of Specimen 3 thereon. This depolarization of the cellular membrane is caused by intraperitoneally administering physiological saline (Control) and Specimen 3 (10 µg/kg) to adult C57BL/6N mice (from 10 to 17 week old, weight: from 28 to 31 g), forming a thin brain slice including the cortex and the hippocampus regions after 22 hours, and adding 80 mM KCl (80 K) to an extracellular fluid.

FIG. 13A to FIG. 13C show, similar to FIG. 12A to FIG. 12C, the measurement of a $K^+$ depolarization-induced $Ca^{2+}$ concentration increase in mitochondria in hippocampal neurons (neurons) and an inhibitory effect of Specimen 3 thereon.

FIG. 29A: Control, FIG. 29B: 10 mg/kg of β-NMN, FIG. 29C: 30 mg/kg of β-NMN, and FIG. 29D: 100 mg/kg of β-NMN. β-NMN was subcutaneously administered at each dose and whole brain slice preparations were formed after 24 hours and stained with Xrhod-1, a mitochondria-specific $Ca^{2+}$ indicator. The time-dependent increase in mitochondrial $Ca^{2+}$ obtained by three times stimulation with 80K ACSF was measured from the red fluorescence imaging (>600 nm) when excited at 580 nm. Solid line: response at a cerebral cortex (CTX) site; dotted line: response at a hippocampal CA1 site (CA1). Shown are an average of from 5 to 6 cases and a standard deviation.

FIG. 30A: Control, FIG. 30B: 0.01 mg/kg of TND1128, FIG. 30C: 0.1 mg/kg of TND1128, and FIG. 30D: 1.0 mg/kg of TND1128 (subcutaneous administration). As in FIG. 29A to FIG. 29D, the time-dependent mitochondrial $Ca^{2+}$ increase obtained by three times stimulation with 80K ACSF was measured from the red fluorescence imaging (>600 nm) of Xrhod-1 loaded preparations when excited at 580 nm. Solid line: response at a cerebral cortex (CTX) site; dotted line: response at a hippocampal CA1 site (CA1). Shown are an average of from 5 to 6 cases and a standard deviation.

FIG. 31A: effect of β-NMN on the total mitochondrial $Ca^{2+}$ uptake amount at the cerebral cortex (CTX) (white) and the hippocampus (CA1) (black) when exposed to 80K ACSF three successive times. FIG. 31B: the dose response relationship of the mitochondrial $Ca^{2+}$ uptake each time when exposed to 80K ACSF at the cerebral cortex. FIG. 31C: the dose response relationship of the mitochondrial $Ca^{2+}$ uptake each time when exposed to 80K ACSF at the hippocampus. *: Significant difference ($P<0.05$) provided by multiple comparison by Tukey's method.

FIG. 32A: effect of TND1128 on the total mitochondrial Ca$^{2+}$ uptake amount at the cerebral cortex (CTX) (white) and the hippocampus (CA1) (black) when exposed to 80K ACSF three successive times. FIG. 32B: the dose response relationship on the mitochondrial Ca$^{2+}$ uptake each time when exposed to 80K ACSF in the cerebral cortex. FIG. 32C: the dose response relationship on the mitochondrial Ca$^{2+}$ uptake each time when exposed to 80K ACSF in the hippocampus. *: Significant difference (P<0.05) provided by multiple comparison by Tukey's method.

FIG. 33A: Control, FIG. 33B: 10 mg/kg of β-NMN, FIG. 33C: 30 mg/kg of β-NMN, and FIG. 33D: 100 mg/kg of β-NMN. Solid line: response at a cerebral cortex (CTX) site; dotted line: response at a hippocampus CA1 site (CA1). Shown are an average of from 5 to 6 cases and a standard deviation.

FIG. 34A: Control, FIG. 34B: 0.01 mg/kg of TND1128, FIG. 34C: 0.1 mg/kg of TND1128, and FIG. 34D: 1.0 mg/kg of TND1128 (subcutaneous administration). As in FIG. 33A to FIG. 33D, a ratio of fluorescence intensity (F360 and F380) of a bluish green color (>500 nm) of Fura-4F when the preparations were exposed to excited lights of 360 nm and 380 nm was found at every 10 seconds with the passage of time. Solid line: response at a cerebral cortex (CTX) site; dotted line: response at a hippocampus CA1 site (CA1). Shown are an average of from 5 to 6 cases and a standard deviation.

FIG. 35A: effects of β-NMN on the total cytoplasmic Ca$^{2+}$ uptake amount at the cerebral cortex (CTX) (white) and the hippocampus (CA1) (black) when exposed to 80K ACSF three successive times. FIG. 35B: the dose response relationship of a cytoplasmic Ca$^{2+}$ uptake each time when exposed to 80K ACSF at the cerebral cortex. FIG. 35C: the dose response relationship of a cytoplasmic Ca$^{2+}$ uptake each time when exposed to 80K ACSF at the hippocampus.

FIG. 36A: effects of β-NMN on the total cytoplasmic Ca$^{2+}$ uptake amount at the cerebral cortex (CTX) (white) and the hippocampus (CA1) (black) when exposed to 80K ACSF three successive times. FIG. 36B: the dose response relationship of the cytoplasmic Ca$^{2+}$ uptake each time when exposed to 80K ACSF at the cerebral cortex. FIG. 36C: the dose response relationship of the cytoplasmic Ca$^{2+}$ uptake each time when exposed to 80K ACSF at the hippocampus. * Significant difference (P<0.05) provided by multiple comparison by Tukey's method.

Figure 1:
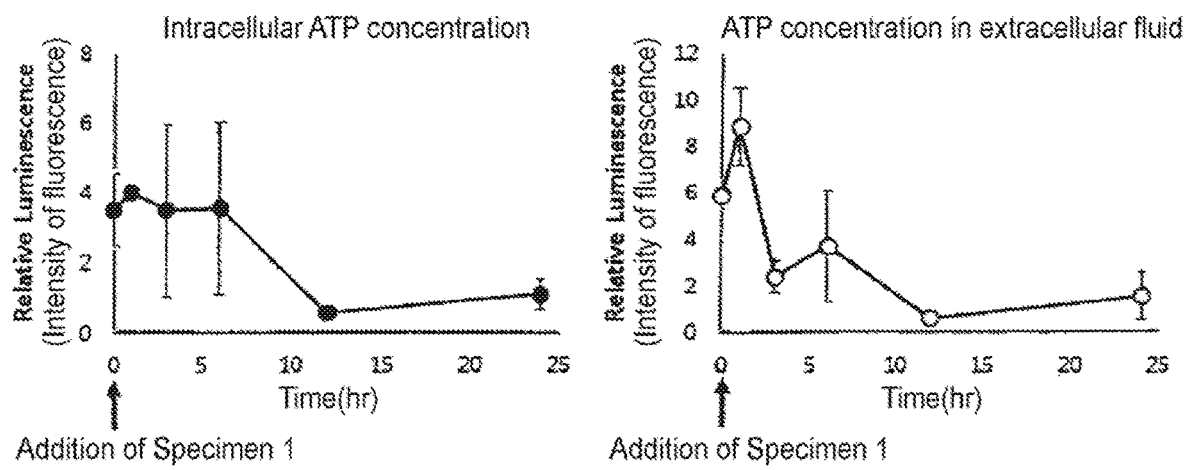
FIG. 1 shows the fluorescence measurement results of intracellular and extracellular ATP concentrations of cultured cells of a human-derived neuroblast (neuroblastoma) SH-SY5Y strain to which Specimen 1 was added.

MODE FOR CARRYING OUT THE INVENTION (Structure of Compound)

In the present invention, use of respective compounds having structural formulas represented by the formulas (I), (II), (III), and (IV) is effective for activating the intracellular ATP production.

Specific examples of these compounds and documents showing the production methods thereof are shown in Tables 1 to 4.

TABLE 1

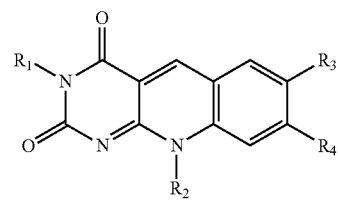

(I)

| Compound No. | R$_1$ | R$_2$ | R$_3$ | R$_4$ | Document of production method |
|---|---|---|---|---|---|
| I-1 | H | Me | H | H | (4) |
| I-2 | H | Me | Me | Me | (4) |
| I-3 | H | Et | H | H | (4) |
| I-4 | H | Et | Me | H | (4) |
| I-5 | H | n-Pr | H | H | (4) |
| I-6 | H | n-Bu | H | H | (1) (4) |

TABLE 1-continued (I)

| Compound No. | $R_1$ | $R_2$ | $R_3$ | $R_4$ | Document of production method |
|---|---|---|---|---|---|
| I-1 | H | Me | H | H | (4) |
| I-2 | H | Me | Me | Me | (4) |
| I-3 | H | Et | H | H | (4) |
| I-4 | H | Et | Me | H | (4) |
| I-5 | H | n-Pr | H | H | (4) |
| I-6 | H | n-Bu | H | H | (1) (4) |
| I-7 | H | n-Bu | $NO_2$ | H | (1) |
| I-8 | H | n-Bu | H | Cl | (1) |
| I-9 | H | $CH_3[CH_2]_7$ | H | H | (1) |
| I-10 | H | $CH_3[CH_2]_7$ | $NO_2$ | H | (1) |
| I-11 | H | $CH_3[CH_2]_7$ | H | Cl | (1) |
| I-12 | H | $CH_3[CH_2]_7$ | H | $OCH_2Ph$ | (13) |
| I-13 | H | $CH_3[CH_2]_7$ | H | OMe | (13) |
| I-14 | H | $CH_3[CH_2]_7$ | H | COMe | (13) |
| I-15 | H | $CH_3[CH_2]_{11}$ | H | H | (1) |
| I-16 | H | $CH_3[CH_2]_{11}$ | $NO_2$ | H | (1) |
| I-17 | H | $CH_3[CH_2]_{11}$ | H | Cl | (1) |
| I-18 | H | $HO[CHOH]_3CH_2$ | H | OBn | (13) |
| I-19 | H | $HO[CHOAc]_3CH_2$ | H | OBn | (13) |
| I-20 | H | Ph | H | H | (1) |
| I-21 | H | Ph | $NO_2$ | H | (1) |
| I-22 | H | Ph | H | Cl | (1) |
| I-23 | H | Ph | H | OH | (1) |
| I-24 | H | $2,4\text{-}Me_2\text{-}C_6H_3$ | H | H | (1) |
| I-25 | H | $2,4\text{-}Me_2\text{-}C_6H_3$ | $NO_2$ | H | (1) |
| I-26 | H | $2,4\text{-}Me_2\text{-}C_6H_3$ | H | Cl | (1) |
| I-27 | H | $3,4\text{-}Me_2\text{-}C_6H_3$ | H | H | (1) |
| I-28 | H | $3,4\text{-}Me_2\text{-}C_6H_3$ | $NO_2$ | H | (1) |
| I-29 | H | $3,4\text{-}Me_2\text{-}C_6H_3$ | H | Cl | (1) |
| I-30 | H | $4\text{-}Cl\text{-}C_6H_4$ | H | H | (1) |
| I-31 | H | $4\text{-}Cl\text{-}C_6H_4$ | H | Cl | (1) |
| I-32 | Me | Me | H | H | (4) (9) |
| I-33 | Me | Me | Me | H | (6) |
| I-34 | Me | Me | H | Me | (5) |
| I-35 | Me | Me | H | F | (9) |
| I-36 | Me | Me | Cl | H | (6) (9) |
| I-37 | Me | Me | H | Cl | (5) (9) |
| I-38 | Me | Me | Cl | Cl | (5) (9) |
| I-39 | Me | Me | H | OH | (1) (9) |
| I-40 | Me | Me | H | OMe | (5) (9) |
| I-41 | Me | Me | H | $N_3$ | (10) |
| I-42 | Me | Me | H | $NH_2$ | (10) |
| I-43 | Me | Me | H | $NMe_2$ | (10) |
| I-44 | Me | Me | H | CN | (6) (9) |
| I-45 | Me | Me | H | $NHCH_2Ph$ | (9) |
| I-46 | Me | Me | H | NHCOMe | (10) |
| I-47 | Me | Me | H | NHCOPh | (10) |
| I-48 | Me | Me | H | $OCH_2Ph$ | (9) |
| I-49 | Me | Me | —O—$CH_2$—O— | | (6) |
| I-50 | Me | Et | H | H | (4) Specimen 1 |
| I-51 | Me | Et | Me | H | (4) |
| I-52 | Me | Et | H | OH | (12) |
| I-53 | Me | n-Pr | H | H | (1) (4) |
| I-54 | Me | n-Bu | H | H | (1) Specimen 2 |
| I-55 | Me | n-Bu | H | OH | (1) |
| I-56 | Me | n-Bu | H | OH | (12) |
| I-57 | Me | $C_6H_{11}$ | H | Cl | (1) |
| I-58 | Me | $CH_3[CH_2]_5$ | H | H | (2) |
| I-59 | Me | $CH_3[CH_2]_7$ | H | H | (2) |
| I-60 | Me | $CH_3[CH_2]_7$ | H | F | (14) |
| I-61 | Me | $CH_3[CH_2]_7$ | H | OH | (12) |
| I-62 | Me | $CH_3[CH_2]_7$ | H | $NH(CH_2)_6NH_2$ | (14) |
| I-63 | Me | $CH_3[CH_2]_{11}$ | H | H | (2) |
| I-64 | Me | $CH_3[CH_2]_{11}$ | H | OH | (12) |
| I-65 | Me | $CH_3[CH_2]_{17}$ | H | H | (2) |
| I-66 | Me | $PhCH_2$ | H | H | (1) |
| I-67 | Me | $HO_2C[CH_2]_3$ | H | OH | (12) |
| I-68 | Me | $HO_2C[CH_2]_3$ | H | OH | (12) |
| I-69 | Me | Ph | H | H | (1) |
| I-70 | Me | Ph | Me | H | (7) |
| I-71 | Me | Ph | H | Me | (7) |
| I-72 | Me | Ph | OMe | H | (7) |
| I-73 | Me | Ph | H | OMe | (7) |
| I-74 | Me | Ph | Cl | H | (7) |
| I-75 | Me | Ph | H | Cl | (1) Specimen 4 |
| I-76 | Me | Ph | H | Br | (3) |
| I-77 | Me | $3\text{-}Me\text{-}C_6H_4$ | H | H | (1) |
| I-78 | Me | $4\text{-}Me\text{-}C_6H_4$ | H | H | (1) |
| I-79 | Me | $4\text{-}Me\text{-}C_6H_4$ | Me | H | (3) |
| I-80 | Me | $4\text{-}Me\text{-}C_6H_4$ | H | Me | (3) |
| I-81 | Me | $4\text{-}Me\text{-}C_6H_4$ | Cl | H | (11) |
| I-82 | Me | $4\text{-}Me\text{-}C_6H_4$ | OH | H | (11) |
| I-83 | Me | $4\text{-}Me\text{-}C_6H_4$ | $NMe_2$ | H | (11) |
| I-84 | Me | $4\text{-}Me\text{-}C_6H_4$ | SMe | H | (11) |
| I-85 | Me | $4\text{-}Me\text{-}C_6H_4$ | $SO_2Me$ | H | (11) |
| I-86 | Me | $3,4\text{-}Me_2\text{-}C_6H_3$ | H | H | (7) |
| I-87 | Me | $3,4\text{-}Me_2\text{-}C_6H_3$ | $NO_2$ | H | (1) |
| I-88 | Me | $4\text{-}MeO\text{-}C_6H_4$ | H | H | (7) |
| I-89 | Me | $4\text{-}F\text{-}C_6H_4$ | H | H | (7) |
| I-90 | Me | $4\text{-}Cl\text{-}C_6H_4$ | H | H | (1) |
| I-91 | Me | $4\text{-}Cl\text{-}C_6H_4$ | H | Cl | (1) |
| I-92 | Me | $4\text{-}Br\text{-}C_6H_4$ | H | H | (3) |
| I-93 | $Br(CH_2)_6$ | $CH_3[CH_2]_7$ | H | H | (14) |
| I-94 | $N_3(CH_2)_6$ | $CH_3[CH_2]_7$ | H | H | (14) |
| I-95 | $NH_2(CH_2)_6$ | $CH_3[CH_2]_7$ | H | H | (14) |

TABLE 1-continued (I)

$$R_1-N, R_2, R_3, R_4 \text{ flavin-like structure}$$

| | | | | | |
|---|---|---|---|---|---|
| I-96 | Ph | Me | H | H | (8) |
| I-97 | Ph | Me | H | OH | (1) |
| I-98 | Ph | Et | H | H | (8) |
| I-99 | Ph | Et | H | OH | (12) |
| I-100 | Ph | n-Pr | H | H | (8) |
| I-101 | Ph | n-Bu | H | H | (1) (8) |
| I-102 | Ph | n-Bu | $NO_2$ | H | (1) |
| I-103 | Ph | n-Bu | H | OH | (12) |
| I-104 | Ph | n-Bu | H | Cl | (1) |
| I-105 | Ph | $CH_3[CH_2]_5$ | H | H | (2) |
| I-106 | Ph | $CH_3[CH_2]_7$ | H | H | (1) |
| I-107 | Ph | $CH_3[CH_2]_7$ | H | Cl | (1) (2) |
| I-108 | Ph | $CH_3[CH_2]_7$ | H | OH | (12) |
| I-109 | Ph | $CH_3[CH_2]_{11}$ | H | H | (1) (2) |
| I-110 | Ph | $CH_3[CH_2]_{11}$ | H | Cl | (1) |
| I-111 | Ph | $CH_3[CH_2]_{12}$ | H | OH | (12) |
| I-112 | Ph | $CH_3[CH_2]_{17}$ | H | H | (2) |
| I-113 | Ph | Ph | H | H | (1) |
| I-114 | Ph | Ph | H | Cl | (1) |
| I-115 | Ph | $3,4\text{-Me}_2\text{—C}_6H_3$ | H | H | (1) |
| I-116 | Ph | $3,4\text{-Me}_2\text{—C}_6H_3$ | H | Cl | (1) |
| I-117 | Ph | $4\text{-Cl—C}_6H_4$ | H | H | (1) |
| I-118 | Ph | $4\text{-Cl—C}_6H_4$ | H | Cl | (1) |

Documents:
(1) T. Nagamatsu, Y. Hashiguchi, and Y. Yoneda, J. Chem. Soc., Perkin Trans. 1, 561-565 (1984)
(2) K. Kuroda, T. Nagamatsu, Y. Sakuma, and F. Yoneda, J. Heterocyclic Chem., 19, 929-931(1982)
(3) K. Kuroda, T, Nagamatsu, R. Yanada, and F. Yoneda, J. Chem. Soc., Perkin Trans. 1, 547-550 (1993)
(4) F. Yoneda, Y. Sakuma, S. Mizumoto, and R. Ito, J. Chem. Soc., Perkin Trans. 1, 1805-1808 (1976)
(5) K. Mori, K. Shinozuka, Y. Sakuma, and F. Yoneda, J. Chem. Soc., Chem. Comm., 764 (1978)
(6) F. Yoneda, K. Mori, and Y. Sakuma, J. Chem. Soc., Perkin Trans, 1, 978-981 (1980)
(7) F. Yoneda, K. Tsukuda, K. Shinozuka, F. Hirayama, K. Uekama, and A. Koshiro, Chem. Pharm. Bull., 28, 3049-3056 (1980)
(8) F. Yoneda, K. Mori, M. Ono, Y. Kadokawa, E. Nagao, and H. Yamaguchi, Chem. Pharm. Bull., 28, 3514-3620 (1980)
(9) F. Yoneda, K. Mori, S. Matsuo, Y. Kadokawa and Y. Samuma, J. Chem. Soc., Perkin Trans. 1, 1836-1839 (1981)
(10) F. Yoneda, K. Mori, Y. Sakuma, and A. Koshiro, J. Heterocyclic Chem., 19, 945-947 (1982)
(11) K. Tanaka, T. Kimura, X. Chen, T. Kawamoto, and F. Yoneda, Chem. Pharm. Bull., 88, 312-317 (1990)
(12) R. Hirayama, M. Kawase, T. Kimachi, K. Tanaka, and F. Yoneda, J. Heterocyclic Chem., 26, 1255-1259 (1989)
(13) T. Kimachi, K. Tanaka, and F. Yoneda, J. Heterocyclic Chem., 28, 439-443 (1991)
(14) Y. Eikyu, Y. Nakamura, T. Akiyama, F. Yoneda, K. Tanaka, and K. Fuji, Chem. Pharm. Bull., 40, 291-293 (1992)

TABLE 2

(II)

| Compound No. | $R_1$ | $R_2$ | $R_3$ | Document of production method |
|---|---|---|---|---|
| II-1 | H | $CH_3[CH_2]_7$ | H | (15) |
| II-2 | H | $CH_3[CH_2]_{11}$ | H | (15) |
| II-3 | H | $CH_3[CH_2]_{17}$ | H | (15) |
| II-4 | H | Me | Me | (16) |

TABLE 2-continued (II)

| Compound No. | $R_1$ | $R_2$ | $R_3$ | Document of production method |
|---|---|---|---|---|
| II-5 | H | Et | Me | (16) |
| II-6 | H | n-Bu | Me | (16) (19) |
| II-7 | H | $CH_3[CH_2]_7$ | Me | (16) (19) |
| II-8 | H | $CH_3[CH_2]_{11}$ | Me | (16) (19) |
| II-9 | H | $CH_3[CH_2]_{17}$ | Me | (18) (19) |
| II-10 | H | $C_6H_5[CH_2]_2$ | Me | (16) |
| II-11 | Me | Me | Me | (15) (16) (17) |
| II-12 | Me | Et | Me | (15) (17) Specimen 5 |
| II-13 | Me | n-Pr | Me | (16) (17) |
| II-14 | Me | n-Bu | Me | (15) (16) (17) |
| II-15 | Me | $CH_3[CH_2]_7$ | Me | (15) (16) (17) |
| II-16 | Me | $CH_3[CH_2]_{11}$ | Me | (15) (16) |
| II-17 | Me | $CH_3[CH_2]_{17}$ | Me | (15) |
| II-18 | Me | $Ph[CH_2]_2$ | Me | (15) |
| II-19 | Me | Ph | Me | (15) |
| II-20 | Me | $4\text{-Me—C}_6H_4$ | Me | (15) |
| II-21 | Me | $4\text{-Cl—C}_6H_4$ | Me | (15) |
| II-22 | Me | $4\text{-Br—C}_6H_4$ | Me | (15) |
| II-23 | Me | $4\text{-MeO—C}_6H_4$ | Me | (15) |
| II-24 | Me | $3,4\text{-Me}_2\text{—C}_6H_4$ | Me | (15) |
| II-25 | $Br(CH_2)_{10}$ | n-Bu | Me | (19) |
| II-26 | $Br(CH_2)_{10}$ | $CH_3[CH_2]_7$ | Me | (19) |
| II-27 | $Br(CH_2)_{10}$ | $CH_3[CH_2]_{11}$ | Me | (19) |
| II-28 | $Br(CH_2)_{10}$ | $CH_3[CH_2]_{18}$ | Me | (19) |
| II-29 | Ph | Ph | Ph | (15) |
| II-30 | Ph | $4\text{-Me—C}_6H_4$ | Ph | (15) |
| II-31 | Ph | $4\text{-Cl—C}_6H_4$ | Ph | (15) Specimen 6 |
| II-32 | Ph | $3,4\text{-Me}_2\text{—C}_6H_4$ | Ph | (15) |

Documents:
(15) T. Nagamatsu, H. Yamato, M. Ono, S. Takarada, and F. Yoneda, J. Chem. Soc., Perkin Trans. 1, 2101-2109 (1992)
(18) T. Nagamatsu, Y. Sakuma, and Y. Yoneda, Synthesis, 923-924 (1983)
(17) F. Yoneda, T. Nagamatsu, M. Takamoto, Chem. Pharm. Bull., 31, 344-347 (1983)
(18) F. Yoneda, H. Yamato, T. Nagamatsu, and H. Egawa, J. Polymer Sci.:Plymer Lett. Ed., 20, 667-670 (1982)
(19) F. Yoneda, K. Tanaka, H. Yamato, K. Moriyama, and T. Nagamatsu, J. Am. Chem. Soc., 111, 9199-9202 (1989)

TABLE 3

(III)

| Compound No. | $R_1$ | $R_2$ | Document of production method |
|---|---|---|---|
| III-1 | H | Me | (20) (21) |
| III-2 | Me | Me | (20) (21) Specimen 7 |
| III-3 | Me | Et | (Unknown compound) |
| III-4 | Me | n-Bu | (Unknown compound) Specimen 3 |
| III-5 | Me | Bn | (Unknown compound) |
| III-6 | Me | Ph | (Unknown compound) |

TABLE 3-continued

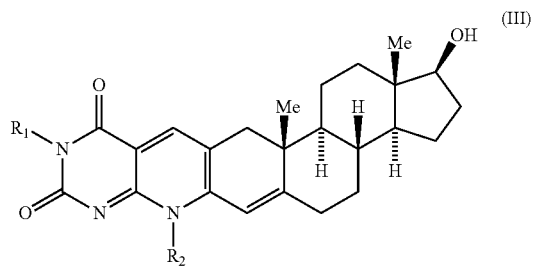

(III)

| Compound No. | R₁ | R₂ | Document of production method |
|---|---|---|---|
| III-7 | Me | 4-Me—C₆H₄ | (Unknown compound) |
| III-8 | Me | 4-MeO—C₆H₄ | (Unknown compound) |
| III-9 | Me | 3,4-OCH₂O—C₆H₃ | (Unknown compound) |
| III-10 | Me | 4-HO—C₆H₄ | (Unknown compound) |
| III-11 | Me | 4-F—C₆H₄ | (Unknown compound) |
| III-12 | Me | 4-Cl—C₆H₄ | (Unknown compound) |
| III-13 | Me | 4-Br—C₆H₄ | (Unknown compound) |
| III-14 | Ph | Et | (Unknown compound) Specimen 8 |
| III-15 | Ph | n-Bu | (Unknown compound) |
| III-16 | Ph | Bn | (Unknown compound) |
| III-17 | Ph | Ph | (Unknown compound) |
| III-18 | Ph | 4-Me—C₆H₄ | (Unknown compound) |
| III-19 | Ph | 4-Me₂—C₆H₃ | (Unknown compound) |
| III-20 | Ph | 4-MeO—C₆H₄ | (Unknown compound) |
| III-21 | Ph | 4-F—C₆H₄ | (Unknown compound) |
| III-22 | Pb | 4-Cl—C₆H₄ | (Unknown compound) |
| III-23 | Ph | 4-Br—C₆H₄ | (Unknown compound) |

Documents:
(20) T. Nagamatsu, H. Yamada, and K. Shiromoto, Heterocycles, 63, 9-16 (2004)
(21) Japanese Patent Application Laid-Open No. 2005-104868

TABLE 4

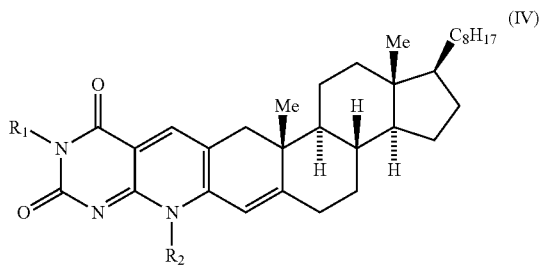

(IV)

| Compound No. | R₁ | R₂ | Document of production method |
|---|---|---|---|
| IV-1 | R | Me | (22) |
| IV-2 | H | Et | (22) |
| IV-3 | H | n-Bu | (22) |
| IV-4 | H | Ph | (22) |
| IV-5 | H | 3-Me—C₆H₄ | (22) |
| IV-6 | H | 3,4-Me₂—C₆H₃ | (22) |
| IV-7 | H | 4-MeO—C₆H₄ | (22) |
| IV-8 | H | 4-F—C₆H₄ | (22) |
| IV-9 | H | 4-Cl—C₆H₄ | (22) |
| IV-10 | Me | Me | (22) Specimen 9 |
| IV-11 | Me | Et | (22) |
| IV-12 | Me | n-Bu | (22) |
| IV-13 | Me | Ph | (22) |
| IV-14 | Me | 3-Me—C₆H₄ | (22) |
| IV-15 | Me | 3,4-Me₂—C₆H₃ | (22) Specimen 10 |
| IV-16 | Me | 4-MeO—C₆H₄ | (22) |
| IV-17 | Me | 4-F—C₆H₄ | (22) |
| IV-18 | Me | 4-Cl—C₆H₄ | (22) |
| IV-19 | Me | 4-Br—C₆H₄ | (22) |
| IV-20 | Ph | Me | (22) |
| IV-21 | Ph | Ph | (22) |

TABLE 4-continued

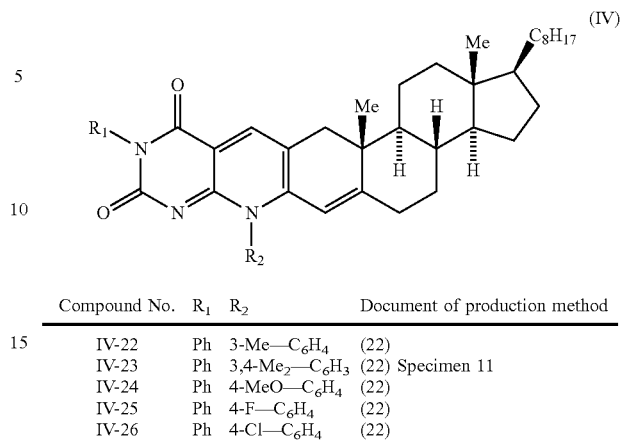

(IV)

| Compound No. | R₁ | R₂ | Document of production method |
|---|---|---|---|
| IV-22 | Ph | 3-Me—C₆H₄ | (22) |
| IV-23 | Ph | 3,4-Me₂—C₆H₃ | (22) Specimen 11 |
| IV-24 | Ph | 4-MeO—C₆H₄ | (22) |
| IV-25 | Ph | 4-F—C₆H₄ | (22) |
| IV-26 | Ph | 4-Cl—C₆H₄ | (22) |

Documents:
(22) A. R. Shrestha, T. Shindo, N. Ashida, and T, Nagamatsu, Bioorg. & Med. Chem., 16, 8685-8696 (2008)

(Production Method of Compound)

D-deazaflavin compounds (from I-1 to I-118) (3) represented by the formula I can be synthesized by the production methods described in the known documents (from 1 to 14). In particular, most of the derivatives can be synthesized by the general production method of Document (1) described in (Production method A). Described specifically, a 6-N-substituted-aminourasil (1) and a suitable o-halogenobenzaldehyde (2) are heated and refluxed in dimethylformamide (DMF). The heating time for from 3 to 7 hours is adequate. The reaction liquid is concentrated under reduced pressure and a residue is recrystallized from a suitable solvent (alcohol, dioxane, DMF, or the like) to obtain a corresponding 5-deazaflavin (3).

Chemical Formula 5

(Production method A)

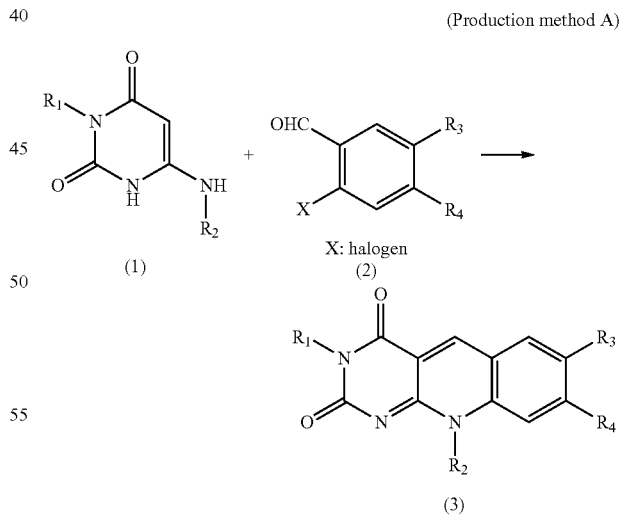

Pyridodipyrimidine compounds (II) (from II-1 to II-32) (5) represented by the formula II can be synthesized by the production method described in the known documents (from 15 to 19). In particular, most of the derivatives can be synthesized by the general production method of Document (15) described in (Production method B). Described specifically, a 6-N-substituted aminouracil (1) and a suitable 3-substituted-6-chlorouracil-5-carbaldehyde (4) are heated and refluxed in dimethylformamide or acetic acid. The heating time for from 2 to 5 hours is adequate. The reaction liquid is concentrated under reduced pressure and the residue is recrystallized from a suitable solvent (alcohol, acetic acid, DMF, or the like) to obtain a corresponding pyridodipyrimidine (5).

Chemical Formula 6

(Production method B)

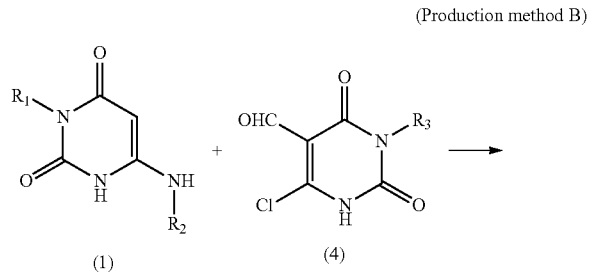

Deazaflavino-testosterone compounds (III) (from III-1 to III-2) (7) represented by the formula III can be synthesized by the production method described in the known documents (20, 21). In a similar manner, the unknown compounds (from III-3 to III-23) can be synthesized. Described specifically, a 6-N-monosubstituted-aminouracil (1) and 2-hydroxymethylene testosterone (6) are added to diphenyl ether. After further addition of p-toluenesulfonic acid, the resulting mixture is heated and stirred at 180° C. for from 30 minutes to 60 minutes in an argon atmosphere. After the reaction, the resulting reaction product is subjected to column chromatography to purify it. The reaction product for the synthesis can also be performed by heating under pressure in dioxane for several hours.

Chemical formula 7

(Production method C)

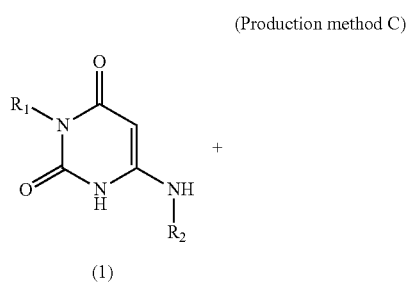

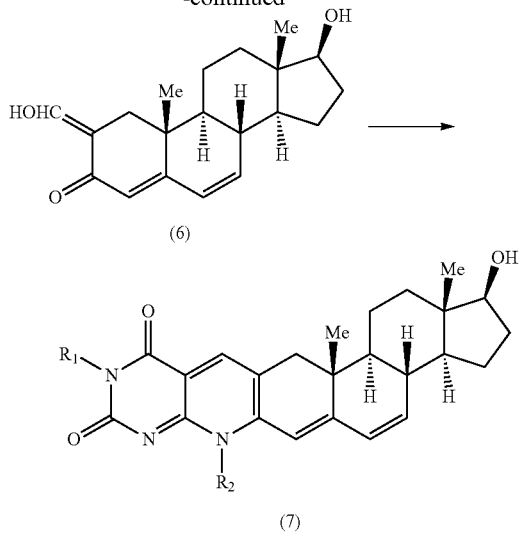

Production Example 1

General Synthesis of 8'-substituted-5'-deaza-17β-hydroxy-3'-methylandrost-2,4-dieno[2,3-g]pteridine-2',4'(3'H,8'H)-dione derivatives (from III-3 to III-13)

To dioxane (50 ml) are added p-toluenesulfonic acid (60 mg, 0.32 mmol) and 6-(monosubstituted-amino)-3-methyluracil (1) (2.84 mmol), followed by the further addition of 2-hydroxymethylene testosterone (6) (1.0 g, 3.16 mmol). Then, the resulting mixture is heated in a sealed tube for 12 hours in argon atmosphere. After the reaction, the reaction product is separated and purified by column chromatography (Fuji Silysia, from 230 to 400 mesh; eluent: ethyl acetate: ethanol=12:1 or ethyl acetate alone) to obtain crystalline powder. Further, recrystallization can be carried out using a mixed solution of ethyl acetate and n-hexane.

Compound III-3 (5'-Deaza-8'-ethyl-17β-hydroxy-3'-methylandrost-2,4-dieno[2,3-g]pteridine-2',4'(3'H,8'H)-dione); yellow crystalline powder(0.77 g, 60%), mp 260° C. (decomp.); $^1$H-NMR (300 MHz, CDCl$_3$) δ: 0.81 (3H, s, 18-CH$_3$), 1.00 (3H, s, 19-CH$_3$), 1.41 (3H, t, J=7.2 Hz, 8'-CH$_2$CH$_3$), 2.46-2.62 (2H, br dd, 6-H), 2.67 (1H, d, J=15.6 Hz, 1β-H), 2.92 (1H, d, J=15.6 Hz, 1α-H), 3.43 (3H, s, 3'-CH$_3$), 3.68 (1H, dd, J$_{16α,17α}$=8.7 Hz, J$_{16β,17α}$=8.1 Hz, 17α-H), 4.46-4.73 (1H, m, 8'-CH$_a$H$_b$), 4.73-5.00 (1H, m, 8'-CH$_a$H$_b$), 6.39 (1H, s, 4-H), 8.25 (1H, s, 5'-H)

Compound III-4 (8'-n-Butyl-5'-deaza-17β-hydroxy-3'-methylandrost-2,4-dieno[2,3-g]pteridine-2',4'(3'H,8'H)-dione); yellow crystalline powder (0.79 g, 58%), mp 246° C. (decomp.); $^1$H-NMR (300 MHz, CDCl$_3$) δ: 0.81 (3H, s, 18-CH$_3$), 0.99 (3H, s, 19-CH$_3$), 1.50 (3H, t, J=7.2 Hz, 8'-CH$_2$CH$_2$CH$_2$CH$_3$), 2.46-2.61 (2H, br dd, 6-H), 2.66 (1H, d, J=15.6 Hz, 1β-H), 2.91 (1H, d, J=15.6 Hz, 1α-H), 3.45 (3H, s, 3'-CH$_3$), 3.69 (1H, dd, J$_{16α,17α}$=7.8 Hz, J$_{16β,17α}$=8.1 Hz, 17α-H), 4.28-4.60 (1H, m, 8'-CH$_a$H$_b$), 4.60-4.92 (1H, m, 8'-CH$_a$H$_b$), 6.35 (1H, s, 4-H), 8.25 (1H, s, 5'-H)

Compound III-5 (8'-Benzyl-5'-deaza-17β-hydroxy-3'-methylandrost-2,4-dieno[2,3-g]pteridine-2',4'(3'H,8'H)-dione); yellow crystalline powder (0.63 g, 43%), mp 215° C.; $^1$H-NMR (300 MHz, CDCl$_3$) δ: 0.78 (3H, s, 18-CH$_3$), 0.95 (3H, s, 19-CH$_3$), 2.37-2.45 (2H, br dd, 6-H), 2.64 (1H, d, J=15.5 Hz, 1β-H), 2.90 (1H, d, J=15.5 Hz, 1α-H), 3.45 (3H, s, 3'-CH$_3$), 3.66 (1H, dd, J$_{16\alpha,17\alpha}$=8.4 Hz, J$_{16\beta,17\alpha}$=8.5 Hz, 17α-H), 5.59 (1H, br d, J=15.3 Hz, 8'-CH$_a$H$_b$), 6.26 (1H, br d, J=15.3 Hz, 8'-CH$_a$H$_b$), 6.28 (1H, s, 4-H), 7.07-7.19 (2H, m, Bn-mH), 7.25-7.35 (3H, m, Bn-o, pH), 8.33 (1H, s, 5'-H)

Compound III-6 (5'-Deaza-17β-hydroxy-3'-methyl-8'-phenylandrost-2,4-dieno[2,3-g]pteridine-2',4'(3'H,8'H)-dione); orange crystalline powder (0.54 g, 38%), mp 215° C. (decomp.); $^1$H-NMR (300 MHz, CDCl$_3$) δ: 0.80 (3H, s, 18-CH$_3$), 1.01 (3H, s, 19-CH$_3$), 2.20-2.43 (2H, br dd, 6-H), 2.76 (1H, d, J=15.9 Hz, 1β-H), 2.96 (1H, d, J=15.9 Hz, 1α-H), 3.40 (3H, s, 3'-CH$_3$), 3.67 (1H, dd, J$_{16\alpha,17\alpha}$=8.7 Hz, J$_{16\beta,17\alpha}$=8.9 Hz, 17α-H), 5.60 (1H, s, 4-H), 6.90-7.22 (2H, m, Ph-mH), 7.22-7.49 (3H, m, Ph-o, pH), 8.39 (1H, s, 5'-H)

Compound III-7 (5'-Deaza-17β-hydroxy-3'-methyl-8'-(4-methylphenyl)androst-2,4-dieno[2,3-g]pteridine-2',4'(3'H, 8'H)-dione); orange crystalline powder (0.58 g, 40%), mp 205° C. (decomp.); $^1$H-NMR (300 MHz, CDCl$_3$) δ: 0.81 (3H, s, 18-CH$_3$), 1.02 (3H, s, 19-CH$_3$), 2.92 (1H, d, J=15.9 Hz, 1β-H), 3.10 (1H, d, J=15.9 Hz, 1α-H), 2.46 (3H, s, 8'-CH$_3$), 3.40 (3H, s, 3'-CH$_3$), 3.67 (1H, dd, J$_{16\alpha,17\alpha}$=8.4 Hz, J$_{16\beta,17\alpha}$=8.7 Hz, 17α-H), 5.56 (1H, s, 4-H), 6.88-7.20 (2H, m, Ar-mH), 7.20-7.47 (2H, m, Ar-oH), 8.37 (1H, s, 5'-H)

Compound III-8 (5'-Deaza-17β-hydroxy-8'-(4-methoxyphenyl)-3'-methylandrost-2,4-dieno[2,3-g]pteridine-2',4' (3'H,8'H)-dione); orange crystalline powder (0.69 g, 47%), mp 220° C. (decomp.); $^1$H-NMR (300 MHz, CDCl$_3$) δ: 0.80 (3H, s, 18-CH$_3$), 1.02 (3H, s, 19-CH$_3$), 2.18-2.41 (2H, br dd, 6-H), 2.70 (1H, d, J=15.6 Hz, 1β-H), 2.96 (1H, d, J=15.6 Hz, 1α-H), 3.40 (3H, s, 3'-CH$_3$), 3.67 (1H, dd, J$_{16\alpha,17\alpha}$=8.7 Hz, J$_{16\beta,17\alpha}$=8.4 Hz, 17α-H), 3.89 (3H, s, OCH$_3$), 5.61 (1H, s, 4-H), 7.02-7.24 (4H, m, Ar-m, oH), 8.36 (1H, s, 5'-H)

Compound III-9 (5'-Deaza-17β-hydroxy-3'-methyl-8'-(3,4-methylenedioxyphenyl)-androst-2,4-dieno[2,3-g]pteridine-2',4'(3'H,8'H)-dione); orange crystalline powder (0.72 g, 47%), mp 214° C.; $^1$H-NMR (300 MHz, CDCl$_3$) δ: 0.79 (3H, s, 18-CH$_3$), 1.01 (3H, s, 19-CH$_3$), 2.22-2.46 (2H, br dd, 6-H), 2.70 (1H, d, J=15.6 Hz, 1β-H), 2.96 (1H, d, J=15.6 Hz, 1α-H), 3.40 (3H, s, 3'-CH$_3$), 3.67 (1H, dd, J$_{16\alpha,17\alpha}$=9.9 Hz, J$_{16\beta,17\alpha}$=8.4 Hz, 17β-H), 5.67 (1H, s, 4-H), 6.08 (2H, s, OCH$_2$O), 6.51-7.17 (1H, m, Ar-mH), 6.86-6.98 (2H, m, Ar-oH), 8.36 (1H, s, 5'-H)

Compound III-10 (5'-Deaza-17β-hydroxy-8'-(4-hydroxyphenyl)-3'-methylandrost-2,4-dieno[2,3-g]pteridine-2',4' (3'H,8'H)-dione); orange crystalline powder (0.47 g, 32%), mp 280° C. (decomp.); $^1$H-NMR (300 MHz, CDCl$_3$) δ: 0.79 (3H, s, 18-CH$_3$), 1.00 (3H, s, 19-CH$_3$), 2.61-2.78 (2H, br dd, 6-H), 2.71 (1H, d, J=15.6 Hz, 1β-H), 2.98 (1H, d, J=15.6 Hz, 1α-H), 3.45 (3H, s, 3'-CH$_3$), 3.67 (1H, dd, J$_{16\alpha,17\alpha}$=7.6 Hz, J$_{16\beta,17\alpha}$=8.4 Hz, 17α-H), 5.68 (1H, s, 4-H), 6.73-6.98 (4H, m, Ar-m, oH), 8.40 (1H, s, 5'-H)

Compound III-11 (5'-Deaza-8'-(4-fluorophenyl)-17β-hydroxy-3'-methylandrost-2,4-dieno[2,3-g]pteridine-2',4'(3'H, 8'H)-dione); orange crystalline powder (0.69 g, 47%), mp 270° C. (decomp.); $^1$H-NMR (300 MHz, CDCl$_3$) δ: 0.80 (3H, s, 18-CH$_3$), 1.00 (3H, s, 19-CH$_3$), 2.68 (2H, dd, J=15.0, 6-H), 2.93 (1H, d, J=15.0 Hz, 1β-H), 3.11 (1H, d, J=15.0 Hz, 1α-H), 3.70 (3H, s, 3'-CH$_3$), 3.56-3.80 (1H, br dd, 17α-H), 6.54 (1H, s, 4-H), 7.12-7.66 (4H, m, Ar-m, oH), 8.50 (1H, s, 5'-H)

Compound III-12 (8'-(4-Chlorophenyl)-5'-deaza-17β-hydroxy-3'-methylandrost-2,4-dieno[2,3-g]pteridine-2',4'(3'H, 8'H)-dione); yellow crystalline powder (0.74 g, 49%), mp 270° C. (decomp.); $^1$H-NMR (300 MHz, CDCl$_3$) δ: 0.80 (3H, s, 18-CH$_3$), 1.03 (3H, s, 19-CH$_3$), 2.19-2.42 (2H, br dd, 6-H), 2.70 (1H, d, J=15.6 Hz, 1β-H), 3.96 (1H, d, J=15.6 Hz, 1α-H), 3.40 (3H, s, 3'-CH$_3$), 3.67 (1H, dd, J$_{16\alpha,17\alpha}$=8.4 Hz, J$_{16\beta,17\alpha}$=8.4 Hz, 17α-H), 5.53 (1H, s, 4-H), 7.06-7.21 (2H, m, Ar-mH), 7.50-7.60 (2H, m, Ar-oH), 8.37 (1H, s, 5'-H)

Compound III-13 (8'-(4-Bromophenyl)-5'-deaza-17β-hydroxy-3'-methylandrost-2,4-dieno[2,3-g]pteridine-2',4'(3'H, 8'H)-dione); orange crystalline powder (0.72 g, 44%), mp 250° C. (decomp.); $^1$H-NMR (300 MHz, CDCl$_3$) δ: 0.80 (3H, s, 18-CH$_3$), 1.03 (3H, s, 19-CH$_3$), 2.25-2.42 (2H, br dd, 6-H), 2.70 (1H, d, J=15.3 Hz, 1β-H), 3.96 (1H, d, J=15.3 Hz, 1α-H), 3.39 (3H, s, 3'-CH$_3$), 3.67 (1H, dd, J$_{16\alpha,17\alpha}$=8.7 Hz, J$_{16\beta,17\alpha}$=8.1 Hz, 17α-H), 5.53 (1H, s, 4-H), 6.99-7.15 (2H, m, Ar-mH), 7.65-7.75 (2H, m, Ar-oH), 8.38 (1H, s, 5'-H)

Production Example 2

General Synthesis of 8'-substituted-5'-deaza-17β-hydroxy-3'-phenylandrost-2,4-dieno[2,3-g]pteridine-2',4'(3'H, 8'H)-dione derivatives (from III-14 to III-23)

To diphenyl ether (1 ml) were added p-toluenesulfonic acid (60 mg, 0.32 mmol), 6-(monosubstituted amino)-3-phenyluracil (1) (0.66 g, 2.84 mmol) and 2-hydroxymethylene testosterone (6) (1.0 g, 3.16 mmol) and the resulting mixture was stirred at 155° C. for 45 minutes in a nitrogen atmosphere. After the reaction, the reaction product was separated and purified by column chromatography (Fuji Silysia from 230 to 400 mesh; eluent:ethyl acetate:ethanol=10:1 or ethyl acetate alone) to obtain crystalline powder. Further, recrystallization can be carried out using a mixed solution of ethyl acetate and n-hexane.

Compound III-14 (5'-Deaza-8'-ethyl-17β-hydroxy-3'-phenylandrost-2,4-dieno[2,3-g]pteridine-2',4'(3'H, 8'H)-dione); yellow crystalline powder (0.79 g, 54%), mp 240° C. (decomp.); 1H-NMR (300 MHz, CDCl$_3$) δ: 0.81 (3H, s, 18-CH$_3$), 1.01 (3H, s, 19-CH$_3$), 1.45 (3H, t, J=7.5 Hz, 8'-CH$_2$CH$_3$), 2.52-2.61 (2H, br dd, 6-H), 2.67(1H, d, J=15.6 Hz, 1β-H), 2.93(1H, d, J=15.6 Hz, 1α-H), 3.68 (1H, dd, J$_{16\alpha,17\alpha}$=7.5 Hz, J$_{16\beta,17\alpha}$=8.1 Hz, 17α-H), 4.46-4.76(1H, m, 8'-CH$_a$H$_b$), 4.76-5.05(1H, m, 8'-CH$_a$H$_b$), 6.41(1H, s, 4-H), 7.21-7.45 (2H, m, Ph-mH), 7.45-7.52 (3H, m, Ph-o, pH), 8.27 (1H, s, 5'-H)

Compound III-15 (8'-n-Butyl-5'-deaza-17β-hydroxy-3'-phenylandrost-2,4-dieno [2,3-g]pteridine-2',4'(3'H,8'H)-dione); yellow crystalline powder (0.77 g, 50%), mp 200° C.; $^1$H-NMR (300 MHz, CDCl$_3$) δ: 0.78 (3H, s, 18-CH$_3$), 0.99 (3H, s, 19-CH$_3$), 1.18 (3H, t, J=7.2 Hz, 8'-CH$_2$CH$_2$CH$_2$CH$_3$), 2.45-2.62 (2H, br dd, 6-H), 2.65 (1H, d, J=15.6 Hz, 1β-H), 2.91(1H, d, J=15.6 Hz, 1α-H), 3.63 (1H, dd, J$_{16\alpha,17\alpha}$=7.1 Hz, J$_{16\beta,17\alpha}$=7.1 Hz, 17α-H), 4.35-4.64 (1H, m, 8'-CH$_a$H$_b$), 4.64-4.94 (1H, m, 8'-CH$_a$H$_b$), 6.39 (1H, s, 4-H), 7.21-7.52 (5H, m, Ph-o, m, pH), 8.27 (1H, s, 5'-H)

Compound III-16 (8'-Benzyl-5'-deaza-17β-hydroxy-3'-phenylandrost-2,4-dieno[2,3-g]pteridine-2',4'(3'H,8'H)-dione); yellow crystalline powder (0.72 g, 44%), mp 224° C.; $^1$H-NMR (300 MHz, CDCl$_3$) δ: 0.81 (3H, s, 18-CH$_3$), 0.92 (3H, s, 19-CH$_3$), 2.30 (2H, dd, J=10.5 Hz, 6-H), 2.63 (1H, d, J=15.6 Hz, 1β-H), 2.87 (1H, d, J=15.6 Hz, 1α-H), 3.67 (1H, dd, J$_{16\alpha,17\alpha}$=8.4 Hz, J$_{16\beta,17\alpha}$=7.8 Hz, 17α-H), 5.37-5.61 (1H, br, 8'-CH$_a$H$_b$), 6.41-6.64 (1H, br, 8'-CH$_a$H$_b$), 7.02 (1H, s, 4-H), 7.24-7.56 (10H, m, Bn-o, m, pH and Ph-o, m, pH), 8.33 (1H, s, 5'-H)

Compound III-17 (5'-Deaza-17β-hydroxy-3',8'-diphenylandrost-2,4-dieno[2,3-g]pteridine-2',4'(3'H,8'H)-dione); orange crystalline powder (0.57 g, 36%), mp 257° C.; $^1$H-NMR (300 MHz, CDCl$_3$) δ: 0.79 (3H, s, 18-CH$_3$), 1.04 (3H, s, 19-CH$_3$), 2.71 (1H, d, J=15.6 Hz, 1β-H), 2.98 (1H, d, J=15.6 Hz, 1α-H), 3.65 (1H, dd, $J_{16α,17α}$=8.4 Hz, $J_{16β,17α}$=8.7 Hz, 17α-H), 5.57(1H, s, 4-H), 7.16-7.66(10H, m, 3'-Ph-o, m, pH and 8'-Ph-o, m, pH), 8.40 (1H, s, 5'-H)

Compound III-18 (5'-Deaza-17β-hydroxy-8'-(4-methylphenyl)-3'-phenylandrost-2,4-dieno[2,3-g]pteridine-2',4'(3'H,8'H)-dione); orange crystalline powder (0.90 g, 55%), mp 246° C. (decomp.); $^1$H-NMR (300 MHz, CDCl$_3$) δ: 0.79 (3H, s, 18-CH$_3$), 0.88 (3H, s, 19-CH$_3$), 2.47 (3H, s, 8'-CH$_3$), 2.58-2.74 (2H, br dd, 6-H), 2.92 (1H, d, J=15.0 Hz, 1β-H), 3.16 (1H, d, J=15.0 Hz, 1α-H), 3.68 (1H, dd, $J_{16α,17α}$=8.7 Hz, $J_{16β,17α}$=7.8 Hz, 17α-H), 6.61 (1H, s, 4-H), 6.89-7.49 (7H, m, 3'-Ph-m, pH and 8'-Ar-o, mH), 8.40-8.56 (2H, m, 3'-Ph-oH), 8.49 (1H, s, 5'-H)

Compound III-19 (5'-Deaza-17β-hydroxy-8'-(3,4-dimethylphenyl)-3'-phenylandrost-2,4-dieno[2,3-g]pteridine-2',4'(3'H,8'H)-dione); orange crystalline powder (0.90 g, 54%), mp 260° C. (decomp.); $^1$H-NMR (300 MHz, CDCl$_3$) δ: 0.77 (3H, s, 18-CH$_3$), 0.80 (3H, s, 19-CH$_3$), 2.33 (3H, s, 8'-Ar—CH$_3$), 2.35 (3H, s, 8'-Ar—CH$_3$), 2.71(1H, d, J=15.0 Hz, 1β-H), 2.97(1H, d, J=15.0 Hz, 1α-H), 3.67 (1H, dd, $J_{16α,17α}$=7.5 Hz, $J_{16β,17α}$=8.4 Hz, 17α-H), 5.60 (1H, s, 4-H), 6.88-7.50 (8H, m, 3'-Ph-o, m, pH and 8'-Ar-o, mH), 8.38 (1H, s, 5'-H)

Compound III-20 (5'-Deaza-17β-hydroxy-8'-(4-methoxyphenyl)-3'-phenylandrost-2,4-dieno[2,3-g]pteridine-2',4'(3'H,8'H)-dione); orange crystalline powder(0.96 g, 57%), mp 250° C. (decomp.); $^1$H-NMR (300 MHz, CDCl$_3$) δ: 0.78 (3H, s, 18-CH$_3$), 0.81 (3H, s, 19-CH$_3$), 2.23-2.38 (2H, br dd, 6-H), 2.71 (1H, d, J=15.6 Hz, 1β-H), 2.93 (1H, d, J=15.6 Hz, 1α-H), 3.62 (1H, dd, $J_{16α,17α}$=6.9 Hz, $J_{16β,17α}$=6.6 Hz, 17α-H), 3.87 (3H, s, OCH$_3$), 6.19 (1H, s, 4-H), 7.00-7.13 (7H, m, 3'-Ph-m, pH and 8'-Ar-o, mH), 7.17-7.50 (2H, m, 3'-Ph-oH), 8.38 (1H, s, 5'-H)

Compound III-21 (5'-Deaza-8'-(4-fluorophenyl)-17β-hydroxy-3'-phenylandrost-2,4-dieno[2,3-g]pteridine-2',4'(3'H,8'H)-dione); orange crystalline powder(0.61 g, 37%), mp 260° C. (decomp.); $^1$H-NMR (300 MHz, CDCl$_3$) δ: 0.79 (3H, s, 18-CH$_3$), 1.04 (3H, s, 19-CH$_3$), 2.70 (1H, d, J=15.9 Hz, 1β-H), 2.97 (1H, d, J=15.9 Hz, 1α-H), 3.66 (1H, dd, $J_{16α,17α}$=8.1 Hz, $J_{16β,17α}$=8.7 Hz, 17α-H), 5.54(1H, s, 4-H), 7.18-7.54 (10H, m, 3'-Ph-o, m, pH and 8'-Ph-o, m, pH), 8.39 (1H, s, 5'-H)

Compound III-22 (8'-(4-Chlorophenyl)-5'-deaza-17β-hydroxy-3'-phenylandrost-2,4-dieno[2,3-g]pteridine-2',4'(3'H,8'H)-dione); orange crystalline powder (0.56 g, 33%), mp 241° C. (decomp.); $^1$H-NMR (300 MHz, CDCl$_3$) δ: 0.77 (3H, s, 18-CH$_3$), 0.85 (3H, s, 19-CH$_3$), 2.29-2.44 (2H, br dd, 6-H), 2.79 (1H, d, J=16.2 Hz, 1β-H), 3.07 (1H, d, J=16.2 Hz, 1α-H), 3.67 (1H, dd, $J_{16α,17α}$=7.8 Hz, $J_{16β,17α}$=8.4 Hz, 17α-H), 6.46 (1H, s, 4-H), 7.17-7.59 (10H, m, 3'-Ph-o, m, pH and 8'-Ph-o, m, pH), 8.47 (1H, s, 5'-H)

Compound III-23 (8'-(4-Bromophenyl)-5'-deaza-17β-hydroxy-3'-phenylandrost-2,4-dieno[2,3-g]pteridine-2',4'(3'H,8'H)-dione); orange crystalline powder (0.93, 51, mp 300° C. (decomp.); $^1$H-NMR (300 MHz, CDCl$_3$) δ: 0.81 (3H, s, 18-CH$_3$), 0.83 (3H, s, 19-CH$_3$), 2.69 (1H, d, J=15.0 Hz, 1β-H), 3.12 (1H, d, J=15.0 Hz, 1α-H), 3.07 (1H, dd, $J_{16α,17α}$=7.9 Hz, $J_{16β,17α}$=8.7 Hz, 17α-H), 6.56 (1H, s, 4-H), 6.69-7.52 (7H, m, 3'-Ph-m, pH and 8'-Ar-o, mH), 7.67-7.79 (2H, m, 3'-Ph-oH), 8.48 (1H, s, 5'-H)

Instrumental analysis values of the above novel compounds (from III-3 to III-23) are shown in Table 5 and Table 6.

TABLE 5

Physical data of 8'-substituted-5'-deaza-17β-hydroxy-3'-methylandrost-2,4-dieno[2,3-g]pteridine-2',4'(3'H,8'H)-diones (III-3-III-13)

| Compd. No. | R | Yield (%)[a] Formula | Mp (° C.) | Analysis (%) Calcd. (Found) | | |
|---|---|---|---|---|---|---|
| | | | | C | H | N |
| III-3 | Et | 60<br>$C_{27}H_{35}N_3O_3$ | 260 (decomp.) | c | | |
| III-4 | Bu | 58<br>$C_{29}H_{39}N_3O_3$ | 246 | 72.92<br>(72.88 | 8.23<br>7.84 | 8.80<br>9.17) |
| III-5 | Bn | 43<br>$C_{32}H_{37}N_3O_3$•3/2H$_2$O | 215 | 71.35<br>(71.55 | 7.48<br>7.30 | 7.80<br>7.83) |
| III-6 | Ph | 38<br>$C_{31}H_{35}N_3O_3$•8/5H$_2$O | 215 (decomp.) | 70.72<br>(70.32 | 7.31<br>7.13 | 7.98<br>8.08) |
| III-7 | 4-Me—C$_6$H$_4$ | 40<br>$C_{32}H_{37}N_3O_3$•1/4H$_2$O | 205 (decomp.) | 74.46<br>(74.25 | 7.32<br>6.93 | 8.14<br>8.17) |
| III-8 | 4-MeO—C$_6$H$_4$ | 46<br>$C_{32}H_{37}N_3O_4$•H$_2$O | 220 (decomp.) | 70.44<br>(70.06 | 7.20<br>7.15 | 7.70<br>8.05) |
| III-9 | 3,4-OCH$_2$O—C$_6$H$_4$ | 47<br>$C_{32}H_{35}N_3O_5$•6/5H$_2$O | 214 | 68.24<br>(68.26 | 6.69<br>6.49 | 7.46<br>7.24) |
| III-10 | 4-HO—C$_6$H$_4$ | 32<br>$C_{31}H_{35}N_3O_4$•1/2H$_2$O | 280 (decomp.) | 71.24<br>(71.04 | 6.94<br>6.74 | 8.04<br>8.23) |
| III-11 | 4-F—C$_6$H$_4$ | 47<br>$C_{31}H_{34}FN_3O_3$•3/2H$_2$O | 270 (decomp.) | 68.61<br>(68.54 | 6.87<br>6.48 | 7.74<br>7.79) |
| III-12 | 4-Cl—C$_6$H$_4$ | 49<br>$C_{31}H_{34}ClN_3O_3$•1/2H$_2$O | 270 (decomp.) | 68.81<br>(68.48 | 6.52<br>6.20 | 7.77<br>7.64) |
| III-13 | 4-Br—C$_6$H$_4$ | 44<br>$C_{31}H_{34}BrN_3O_3$•1/2H$_2$O | 250 (decomp.) | 63.59<br>(63.88 | 6.02<br>6.06 | 7.18<br>7.18) |

[a] All compounds were obtained as yellow powder.
[b] All compounds were recrystallized from EtOAc-n-hexane.
[c] Mass Spectrum: MH$^+$ = 450 (Matrix:Gly).

TABLE 6

Physical data of 8'-substituted-5'-deaza-17β-hydroxy-3'-phenylandrost-2,4-dieno[2,3-g]pteridine-2',4'(3'H,8'H)-diones (III-14-III-23)

| Compd. No. | R | Yield (%)[a] Formula | Mp (° C.) | Analysis (%) Calcd. (Found) | | |
|---|---|---|---|---|---|---|
| | | | | C | H | N |
| III-14 | Et | 54 | 240 | 73.82 | 7.36 | 8.07 |
| | | $C_{32}H_{37}N_3O_3 \cdot 1/2H_2O$ | (decomp.) | (73.48 | 7.64 | 7.94) |
| III-15 | Bu | 50 | 200 | 73.46 | 7.76 | 7.56 |
| | | $C_{34}H_{43}N_3O_3 \cdot 9/10H_2O$ | | (73.25 | 7.66 | 7.77) |
| III-16 | Bn | 44 | 224 | 75.10 | 6.98 | 7.10 |
| | | $C_{37}H_{39}N_3O_3 \cdot H_2O$ | | (75.38 | 7.06 | 7.45) |
| III-17 | Ph | 36 | 257 | 75.63 | 6.76 | 7.35 |
| | | $C_{36}H_{37}N_3O_3 \cdot 2/3H_2O$ | | (75.55 | 6.58 | 7.69) |
| III-18 | 4-Me—$C_6H_4$ | 55 | 246 | 73.97 | 7.05 | 6.99 |
| | | $C_{37}H_{39}N_3O_3 \cdot 3/2H_2O$ | | (73.78 | 6.66 | 7.33) |
| III-19 | 3,4-$Me_2$—$C_6H_4$ | 54 | 260 | 75.72 | 7.13 | 6.97 |
| | | $C_{38}H_{41}N_3O_3 \cdot 5/6H_2O$ | (decomp.) | (75.49 | 6.75 | 6.83) |
| III-20 | 4-MeO—$C_6H_4$ | 57 | 250 | 73.85 | 6.76 | 6.98 |
| | | $C_{37}H_{39}N_3O_4 \cdot 2/3H_2O$ | (decomp.) | (73.54 | 6.75 | 7.07) |
| III-21 | 4-F—$C_6H_4$ | 37 | 260 | 73.70 | 6.36 | 7.16 |
| | | $C_{36}H_{36}FN_3O_3 \cdot 1/2H_2O$ | (decomp.) | (73.81 | 6.72 | 6.97) |
| III-22 | 4-Cl—$C_6H_4$ | 33 | 241 | 70.89 | 6.24 | 6.89 |
| | | $C_{36}H_{36}ClN_3O_3 \cdot 7/8H_2O$ | (decomp.) | (71.06 | 6.48 | 6.50) |
| III-23 | 4-Br—$C_6H_4$ | 51 | 300 | | c | |
| | | $C_{36}H_{36}BrN_3O_3$ | (decomp.) | | | |

[a] All compounds were obtained as yellow powder.
[b] All compounds were recrystallized from EtOAc-n-hexane.
[c] Mass Spectrum: MH$^+$ = 640, MH$^+$ + 2 = 642 (Matrix:Gly).

Pyridodipyrimidine compounds (IV) (from IV-1 to IV-26) (9) represented by the formula IV can be synthesized by a production method described in the known document (22) (Production method D). Described specifically, p-toluenesulfonic acid, 3-substituted-6-monosubstituted aminouracil (1), and 2-hydroxymethylenecholest-4-en-3-one (8) are added to diphenyl ether and the resulting mixture is heated and stirred at 180° C. for 45 minutes in a nitrogen atmosphere. After the reaction, the reaction product is separated and purified by column chromatography (Fuji Silysia, from 230 to 400 mesh; eluent: ethyl acetate) to obtain crystalline powder.

Chemical Formula 8

(Production method D)

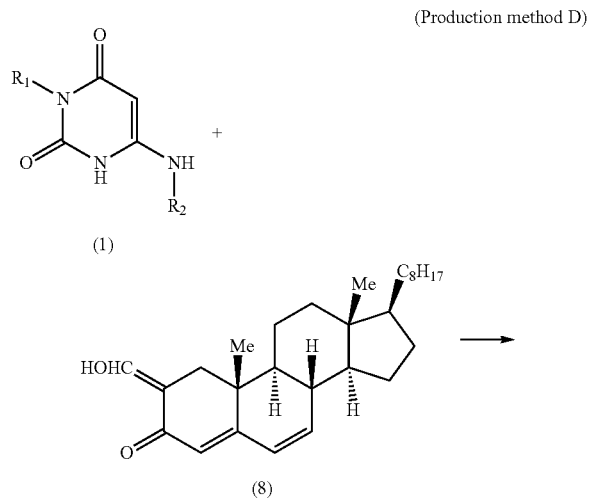

-continued

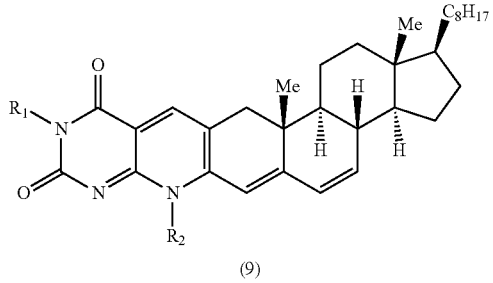

Next, direct or indirect contribution of the addition of each of Compounds No. I-50 (Specimen 1), I-54 (Specimen 2), III-4 (Specimen 3), and I-75 (Specimen 4) to intracellular ATP production was verified by an experiment, so that it will next be described in Examples.

Example 1

After the addition of Specimen 1 to cultured cells of a human-derived neuroblast (Neuroblastoma) SH-SY5Y strain, fluorescence measurement of an intracellular/extracellular ATP concentration was performed. The results are shown in FIG. 1. In the cells, an increase in ATP production (increase in fluorescence intensity) is observed for 5 hours immediately after the addition of Specimen 1 (1 μM) and the effect disappears after 12 hours. It is to be noted that no morphological change of the cultured cells by the treatment with the specimen is observed.

Also outside the cells, an increase in ATP production is observed for 5 hours immediately after the addition of Specimen 1 (1 μM) and an ATP concentration increases, which is presumed to occur due to the outflow of ATP, which has shown an increase in the cells, therefrom.

Example 2

Figure 2A:
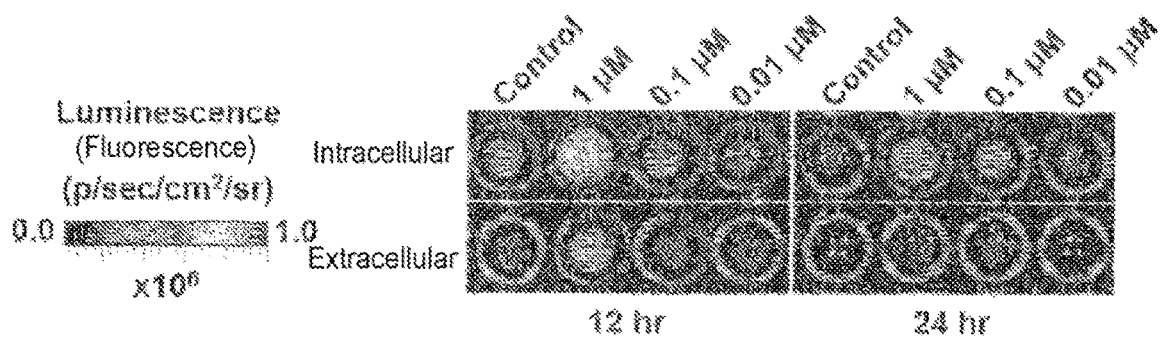
FIG. 2A shows the fluorescence measurement results of cultured astrocytes, one of glial cells of the central nerve system, to which Specimen 1 was added.
Figure 2B:
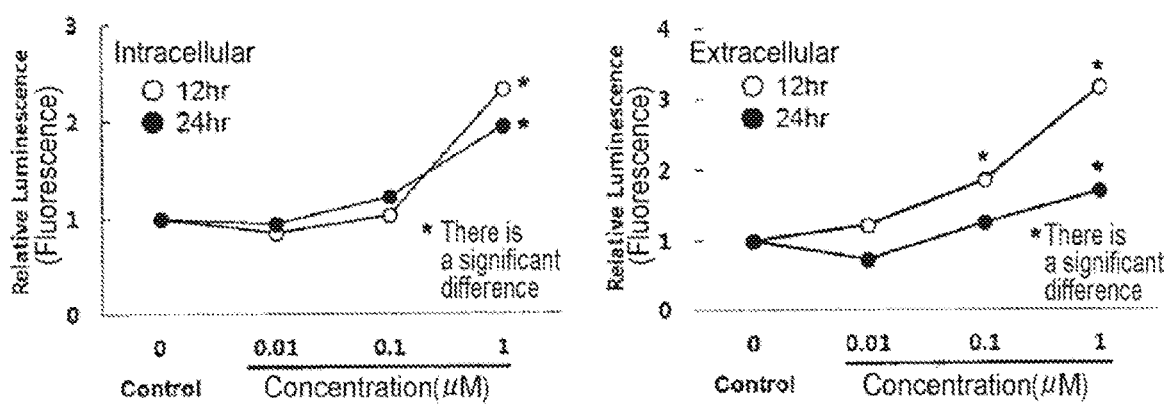
FIG. 2B shows the quantified measurement results of FIG. 2A.

Specimen 1 was added to astrocytes, one of glial cells of the central nerve system, after culturing and the fluorescence measurement results are shown in FIG. 2A and FIG. 2B.

The ATP amount in the glial cells significantly increased 12 hours and 24 hours after the administration of 1 μM of Specimen 1 and an extracellular amount also shows a similar tendency.

Example 3

Figure 3:
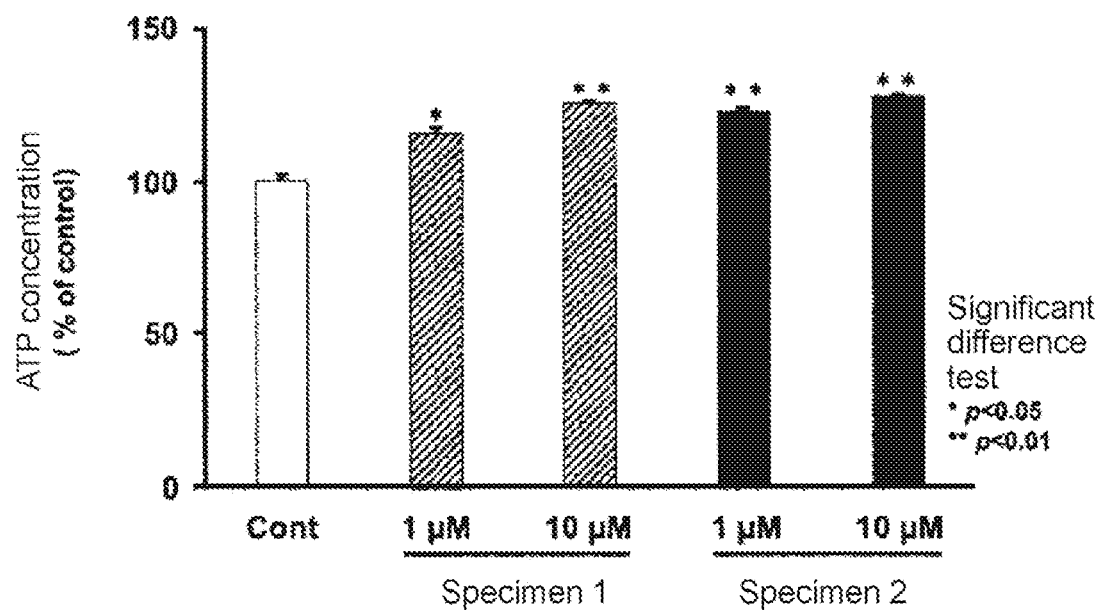
FIG. 3 shows relative comparison between the intracellular ATP concentration after addition of Specimens 1 and 2 to cultured human glioma U251 cells (Sig1-R transfected cells) and that without addition (Cont.).

To cultured human glioma US251 cells (Sig1-R transfected cells) were added Specimens 1 and 2, respectively and intercomparison was performed between intracellular ATP concentration after addition and that without addition (Cont.). As a result, it was verified as shown in FIG. 3 that Specimen 1 and Specimen 2 significantly increased the ATP production amount of human glioma U251 cells. Specimen 2 having higher lipophilicity is more effective than Specimen 1. It is to be noted that fluorescence measurement was performed 6 hours after the administration of the specimens.

In Examples 1 to 3, an experiment on brain neurons (neurons) was performed. The brain neurons (neurons) require oxygen ($O_2$) and glucose. These two substances are first taken into glias (astrocytes) from the blood and then, transmitted from the glias to neurons. The specimen also shows similar transmission. An increase in ATP amount in the glias caused by the addition of the specimen therefore shows direct promotion of the activity of the glias and at the same time, suggests indirect activation of the neurons.

Example 4

Hippocampal neurons were collected from a juvenile (0 day after birth) ICR mouse brain and neurons were cultured on a culture dish.

Specimen 1 was added once to the cells in the initial stage of growth (on culture day 1) and after three days (on culture day 4), the number of neuron axons, dendrites, and growing synapses of the hippocampal neurons (neurons) was quantified. Specimen 1 (0.1 μM, 0.3 μM, 1.0 μM) was added once on culture day 1. Axon and Dendrite were immunostained with a tau antibody and a MAP2 antibody, respectively, three days after the addition (on culture day 4) and morphology thereof was observed.

Figure 4:
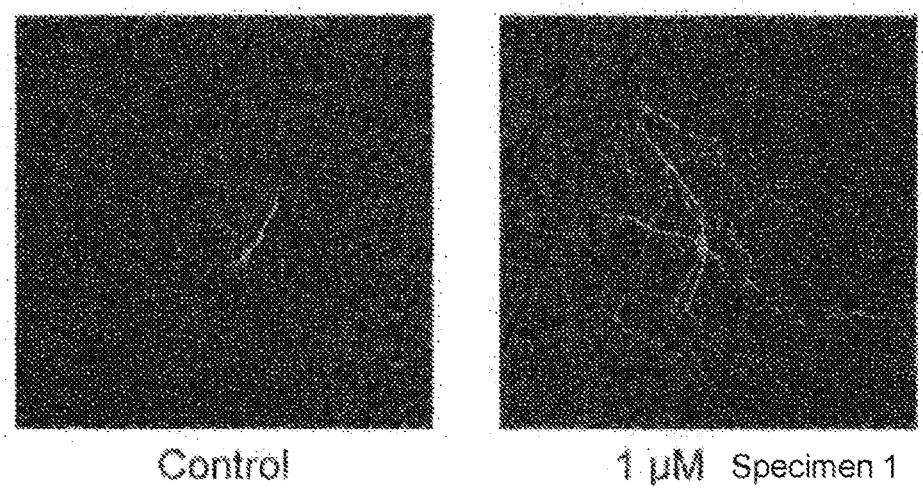
FIG. 4 is an immunostained image showing elongation/growth/branching of a neuron axon of a hippocampal neuron after collecting the hippocampal neuron from a juvenile (0 day after birth) ICR mouse brain, culturing the neurons on a culture dish, and adding Specimen 1 thereto.

FIG. 4 shows immunostained images of the hippocampal neuron axon. On culture day 4, the axon was immunostained with a tau antibody. In these images, a left one shows Control (control group) and a right one shows a specimen-added neuron obtained by adding Specimen 1 (1 μM) once on culture day 1.

Figure 5:
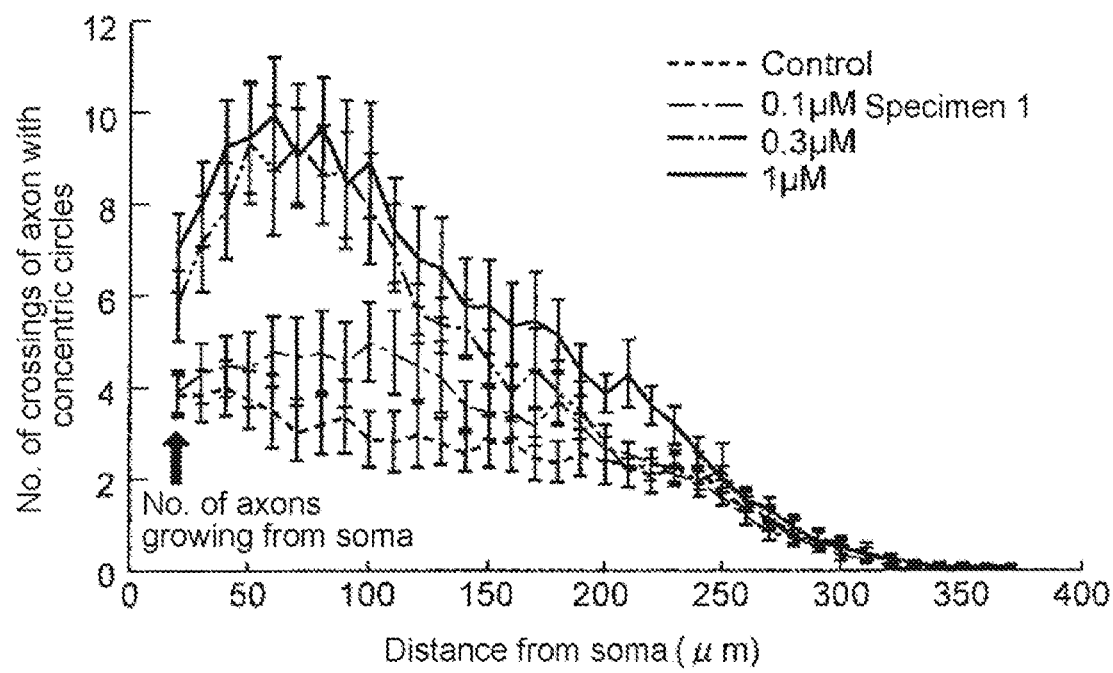
FIG. 5 shows the measurement results of the number of branches of a hippocampal neuron axon after Specimen 1 was added thereto as in FIG. 4.

FIG. 5 shows the number of branches of hippocampal neuron axons and the number of branches of the axons stained with a tau antibody was quantified on culture day 4. An experiment was performed by drawing concentric circles (not shown) at an interval of 10 μm with a soma as a center and the number of axons crossing the circles was measured.

FIGS. 4 and 5 show that Specimen 1 concentration-dependently increases the elongation/growth of neuron axons and the number of branches. The respective specimens having a concentration of 0.3 μM and 1.0 μM exhibited almost similar maximum drug efficacy.

Figure 6:
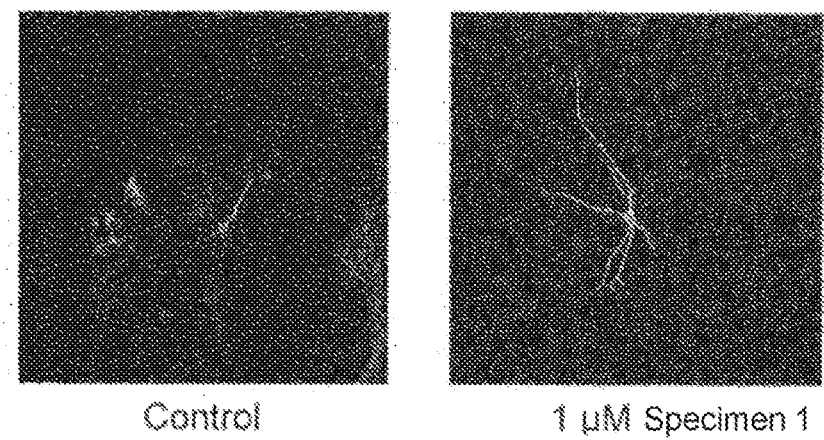
FIG. 6 is an immunostained image showing elongation/growth/branching of a hippocampal neuron dendrite after Specimen 1 was added thereto as in FIG. 4.

FIG. 6 shows an immunostained image of a hippocampal neuron dendrite. The dendrite was immunostained with a MAP2 antibody on culture day 4. A left image shows Control (control group) and a right image shows neurons to which Specimen 1 (1 μM) was added once on culture Day 1.

Figure 7:
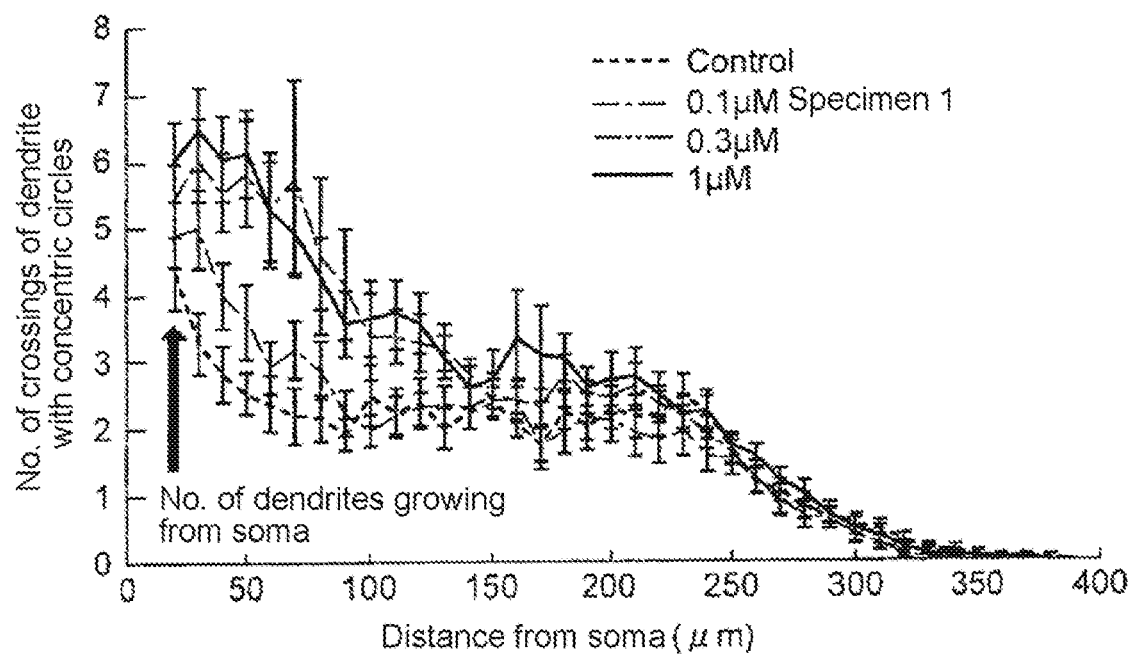
FIG. 7 shows the measurement results of the number of branches of a hippocampal neuron dendrite after Specimen 1 was added thereto as in FIG. 6.

FIG. 7 shows the number of branches of a hippocampal neuron dendrite. The dendrite was immunostained with a MAP2 antibody on culture day 4 and the number of branches of the dendrite was quantified. An experiment was performed by drawing concentric circles (not shown) at an interval of 10 μm with a soma as a center and the number of dendrites crossing the circles was counted.

FIGS. 6 and 7 show that Specimen 1 concentration-dependently extended the dendrite and increased the number of branches thereof. The respective specimens having concentrations of 0.3 μM and 1.0 μM showed almost similar maximum drug efficacy.

Then, excitatory synapses on culture 14 day were immunostained with a VGLUT1 antibody and the number of synapses was quantified.

Figure 8:
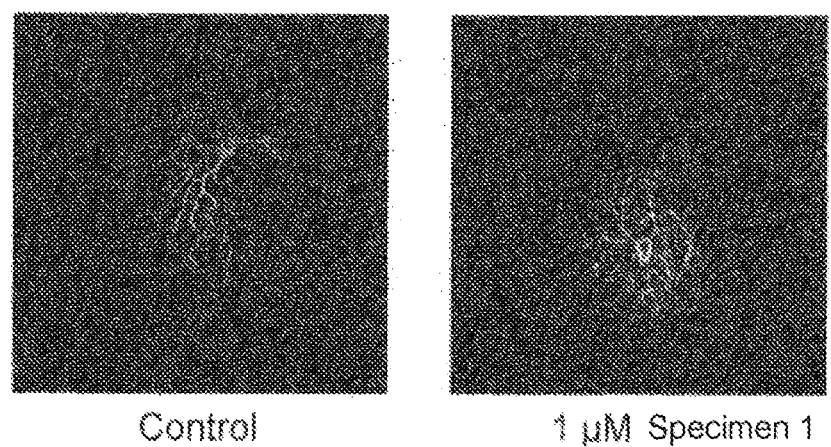
FIG. 8 is an immunostained image of a synapse in an autapse preparation obtained by culturing as in FIG. 4 and immunostaining an excitatory synapse on culture day 14.

FIG. 8 shows an immunostained image of a synapse in an autapse preparation. The left image shows Control (control group) and the right image shows neurons obtained by adding Specimen 1 (1 μM) only once on culture day 1 and then immunostaining an excitatory synapse with a VGLUT1 antibody on culture day 14.

Figure 9:
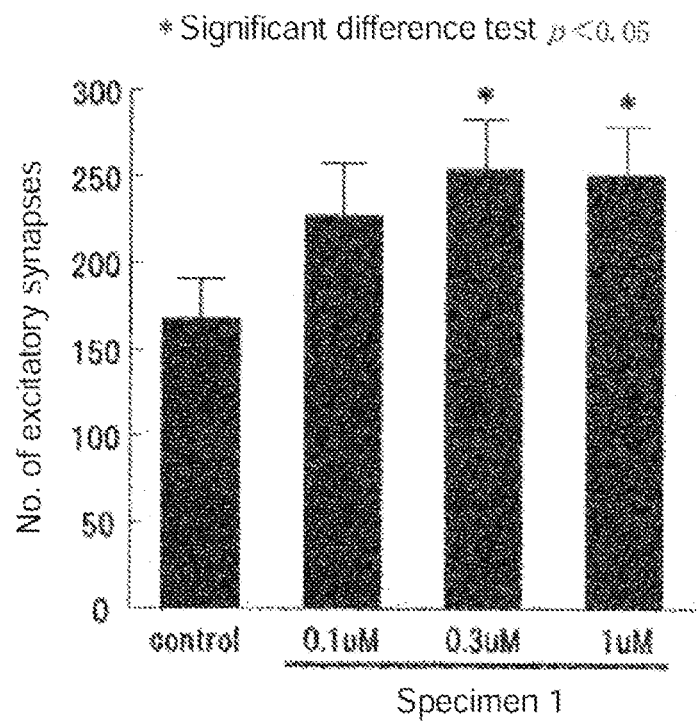
FIG. 9 shows the number of excitatory synapses on culture day 14 quantified after culturing as in FIG. 4.

FIG. 9 shows an increase in excitatory synapse projected to hippocampal neurons. The brain has two synapses, that is, glutamatergic and GABAergic synapses which speedily transmit excitation and inhibition of neurons. FIG. 9 shows the quantified number of excitatory synapses immunostained with a VGLUT1 antibody on culture day 14.

FIGS. 8 and 9 show that addition of Specimen 1 in an amount of 0.3 μM significantly increased the number of excitatory synapses to the maximum.

Example 5

As in Example 4, hippocampal neurons were collected from a juvenile (0 day after birth) ICR mouse brain and the neurons were cultured on a culture dish.

Specimen 1 was administered once to the mature cultured hippocampal cells (on culture day 11) and three days later (on culture day 14), the neuron axons and dendrites of the hippocampal neurons (neurons) were observed. The axons on culture day 14 showed marked elongation and marked crossings therebetween and the number of the axons cannot be quantified, so that only the morphology of the dendrites was observed.

Figure 10:
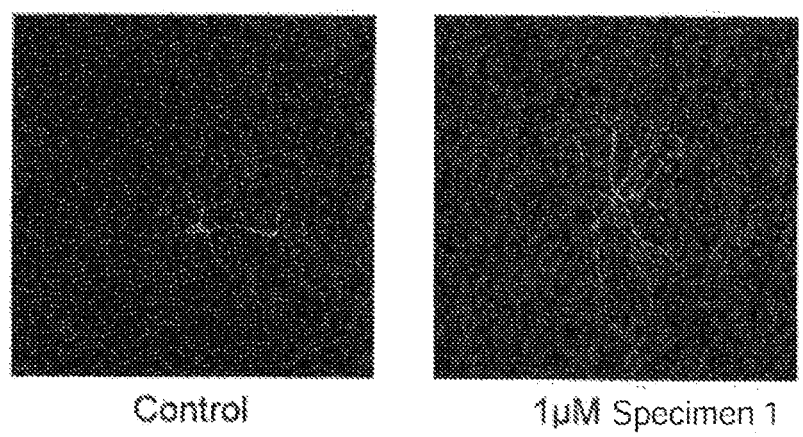
FIG. 10 is an immunostained image of a hippocampal neuron dendrite quantified three days (on culture day 14) after single administration of Specimen 1 to a mature cultured hippocampal neuron (on culture day 11).

FIG. 10 includes immunostained images of the hippocampal neuron dendrite. A left one is an image of Control (control group) and a right one is an image on culture day 14 obtained by administering Specimen 1 and immunostaining with a MAP2 antibody on culture day 14.

Figure 11:
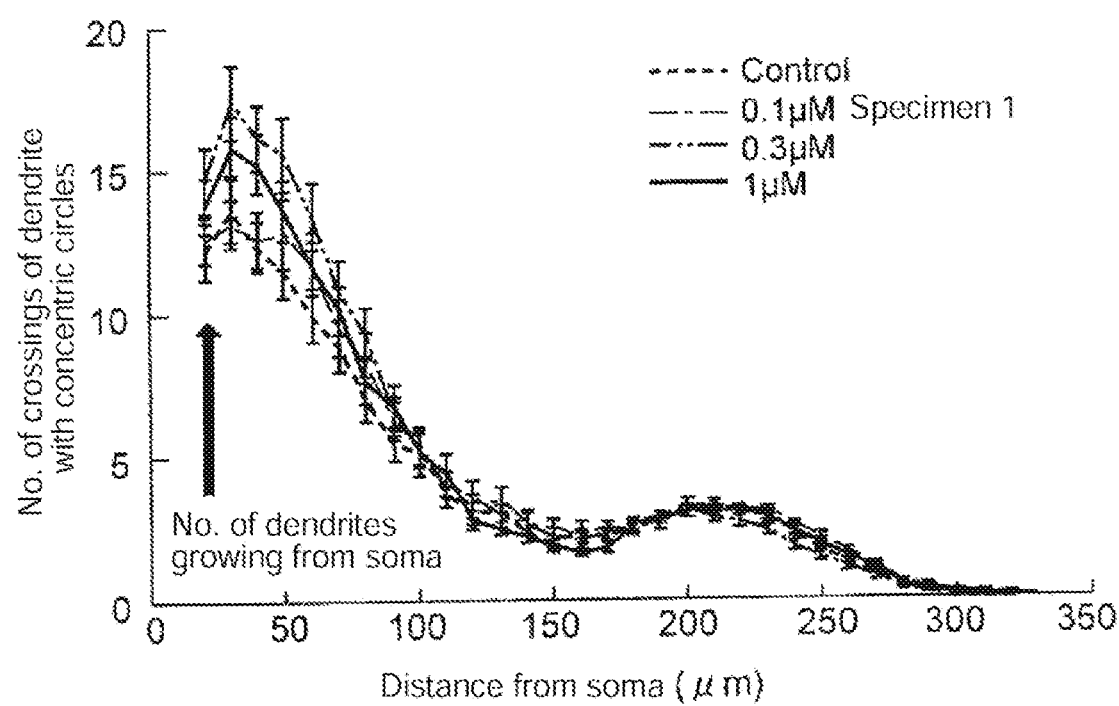
FIG. 11 shows the number of branches of a dendrite measured after immunostaining with a MAP2 antibody in the growth stage on culture day 14 as in FIG. 10.

FIG. 11 shows the number of branches of a dendrite immunostained with a MAP2 antibody on culture day 14, that is, in the latter growth stage and quantified at a specimen concentration of from 0.1 to 1 μM. Concentric circles were drawn at an interval of 10 μm with a soma as a center and the number of dendrites crossing the circles was measured.

Compared with the number of dendrites of the immature cultured cells on day 4 (FIG. 7), the number of dendrites growing from the soma increases, depending on the number of culturing days (FIG. 11). Although the number of dendrites tends to increase even in the mature cultured cell at concentrations of the specimen added (0.3 μM and 1 μM), an increase in the number of branches was not so more marked than that caused by the drug efficacy observed in the cells on culture day 4.

The experimental results in Examples 4 and 5 have indirectly proved that due to the addition of the specimen, increase or promotion of the growth/branching/the number of synapses of immature/mature cultured neurons of rats is promoted by increased ATP production in neurons.

Example 6

One of adult C57BL/6N mice (from 10 to 17 weeks old, weight: from 28 to 31 g) was intraperitoneally administered with physiological saline (Control) and the other one with Specimen 3 (10 μg/kg). After 22 hours, a thin brain slice preparation of each mouse including the cortex and the hippocampus was made. Depolarization of a cellular membrane was caused by the addition of 80 mM KCl (80K) to an extracellular fluid and an increase in mitochondrial $Ca^{2+}$ concentration resulting therefrom was measured by a fluorescent method with Rhod-2 (Note 1). Positive participation of Specimen 3 to the ATP activity in mitochondria was indirectly verified (Note 3) by using, as an index, how the $Ca^{2+}$ concentration to be increased by 80K (Note 2) is suppressed by Specimen 3 in the brain slice.

(Note 1) Rhod-2: $Ca^{2+}$ fluorescent dye selectively incorporated in mitochondria (Note 2) The depolarization of the neuronal membrane by 80K occurs due to both the flow of $Ca^{2+}$ from the outside to the inside of the cell and the release of $Ca^{2+}$ from an intracellular Ca store. The free $Ca^{2+}$ which has increased in the cell easily enters the mitochondria, an intracellular independent organ. This results in an increase in the mitochondrial $Ca^{2+}$ concentration.

(Note 3) The free $Ca^{2+}$ which has increased in the neuronal cytoplasm due to 80K stimulation-induced depolarization speedily and immediately transmits into the mitochondria from the cytoplasm. A decrease in the mitochondrial free $Ca^{2+}$ concentration caused by the specimen occurs because the free $Ca^{2+}$ is scooped out of the cell by an outward Ca pump present in the neuron cytoplasm membrane or adsorption and fixing to a portion inside the mitochondria. Energy for it is supplied from ATP produced in the mitochondria. Based on the results thus obtained, intraperitoneally injected Specimen 3 passes from the blood to glia (astrocyte) cells and is then, incorporated in the mitochondria in the cerebral cortex or hippocampal neuron, by which ATP production in the mitochondria is activated and neurons are activated. The Ca pump on the neuron cytoplasm gets ATP, an energy source, from the mitochondria, while discharges extra intracellular free $Ca^{2+}$ out of the cell and indirectly protects neurons.

FIG. 12A to FIG. 12C show the measurement of a $K^+$ depolarization-induced $Ca^{2+}$ concentration increase in mitochondria present in the cerebral cortex neurons (neurons) and an inhibitory effect of Specimen 3 thereon.

FIG. 12A shows a control reaction when a brain slice preparation obtained from a normal mouse is treated with a 80 mM KCl extracellular fluid (application for 5 minutes, followed by washing for 5 minutes) three successive times. Fluorescence measurement results of a mitochondrial $Ca^{2+}$ increase are plotted along the ordinate.

FIG. 12B shows variations of a mitochondrial $Ca^{2+}$ concentration when a 80K extracellular fluid is given to a brain slice preparation excised and obtained from a rat 22 hours after it was intraperitoneally (i.p.) injected with 10 μg/kg of Specimen 3. Compared with a, suppression of the $Ca^{2+}$ concentration increase and a faster recovery from the $Ca^{2+}$ concentration increased by 80K depolarization can be observed.

FIG. 12C shows a comparison between Control and Specimen 3 in the effect on the mitochondrial $Ca^{2+}$ concentration in the cerebral cortex neuron. The maximum efficacy for suppressing the $Ca^{2+}$ concentration at 10 μm/kg is observed (the same results as those at an injection of 10 mg/kg, 1000 times the amount) (n=3 average: data obtained from three slices obtained from the same individual).

FIG. 13A to FIG. 13C show the measurement of a $K^+$ depolarization-induced mitochondrial $Ca^{2+}$ concentration increase in hippocampal neurons (neurons).

FIG. 13A shows a control reaction when a 80 mM KCl extracellular fluid (application for 5 minutes, followed by washing for 5 minutes) is given three successive times.

FIG. 13B shows variations of a mitochondrial $Ca^{2+}$ concentration when a 80K extracellular fluid is given to a brain slice preparation made 22 hours after intraperitoneal injection of 10 μg/kg of Specimen 3.

FIG. 13C shows a comparison among Control and 10 μg/kg and 10 mg/kg i.p. of Specimen 3 in the inhibitory effect on a mitochondrial $Ca^{2+}$ concentration increase in hippocampal neurons. The maximum effect is attained at 10 μg/kg (n=3, average: data from three slices obtained from the same individual).

Based on the experimental results in Example 6, the 10 μg/kg i.p. pretreatment in vivo with Specimen 3 decreases a 80K depolarization-induced increase in mitochondrial $Ca^{2+}$ concentration in the mouse cortex and hippocampal neurons (neurons) markedly and at the maximum. These results suggest that Specimen 3 relieves the damage of neurons which has occurred at the time of cerebral ischemia or the like.

This suggests that against a Ca load due to a mitochondrial free $Ca^{2+}$ increase that damages adult mouse brain neurons, an ATP increase caused by Specimen 3 activates a Ca pump on the cellular membrane, decreases the mitochondrial free $Ca^{2+}$ amount, and thereby contributes to prevention of neuronal apoptosis (indirect proof of ATP increase).

Example 7

An experiment was made for confirming the effect of the addition of a specimen to cerebral ischemia model adult rats having deteriorated exercise performance.

Intracerebral hemorrhage model rats were prepared by making a small hole into the skull of adult Wistar rats (weight: from 200 to 230 g) under inhalation anesthesia, administering 1.2 μl of a physiological saline to the right brain striatum in Control group and a physiological saline comprising 0.24 U collagenase (type IV) to that of a hemorrhage group.

Figure 14:
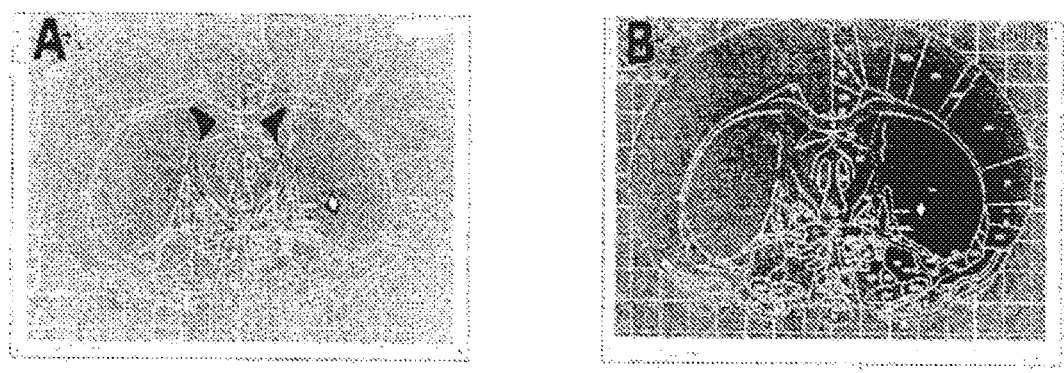
FIG. 14 shows the respective brain cross-sections of intracerebral hemorrhage model rats obtained by making a small hole into the skull of adult Wistar rats (weight: from 200 to 230 g) under inhalation anesthesia and then injecting 1.2 µl of a physiological saline to the right brain striatum in Control group and a physiological saline comprising 0.24 U collagenase (type N) to that in a hemorrhage group.

FIG. 14 shows the respective brain cross-sections of the intracerebral hemorrhage model rats.

In order to confirm the brain cell protective action of Specimen 4 for the intracerebral hemorrhage model rats, 100 μg/kg of Specimen 4 was injected into a spot (white lozenge in the drawing) one hour after administration of collagenase, and exercise footprints of the rat were quantitatively measured. (A: Control, B: Hemorrhage group. Pay attention to color change (to black) after hemorrhage).

For the measurement of the amount of exercise, the moving image of the rats was photographed for 5 minutes. The free movement (exercise distance and exercise speed) during the latter 3 minutes of the photographing time was analyzed.

Figure 15:
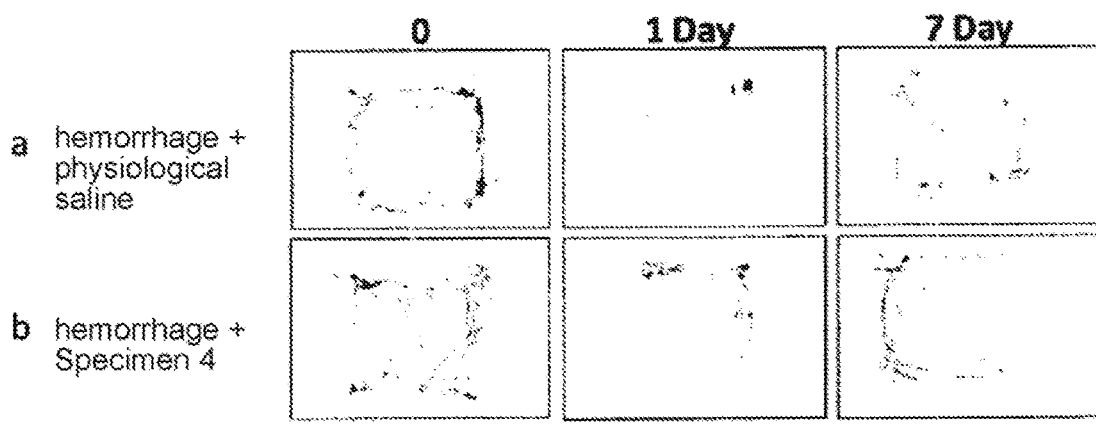
FIG. 15 shows the quantitative measurement of exercise footprints of an intracerebral hemorrhage model rat after injecting 100 µg/kg of Specimen 4 to the brain spot thereof one hour after collagenase administration in order to verify the brain cell protective action of Specimen 4.

FIG. 15 shows the measurement of exercise footprints of the rats. Rat exercise footprints in Box measured with video camera. While FIG. 16 shows the measurement of daily changes of the exercise distance and exercise speed.

Figure 16:
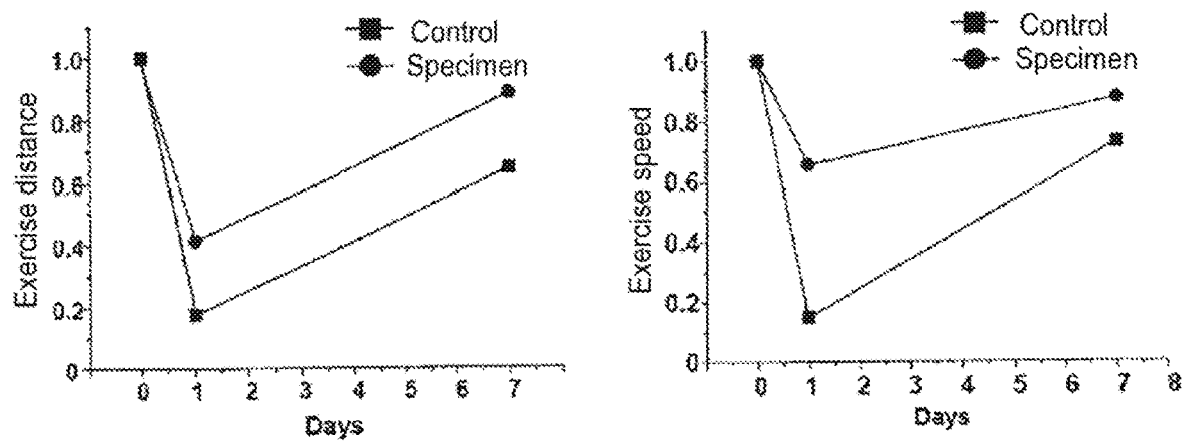
FIG. 16 shows the daily changes of an exercise distance and an exercise speed of a rat administered or not administered with Specimen 4, which was measured as in FIG. 15.
Figure 17:
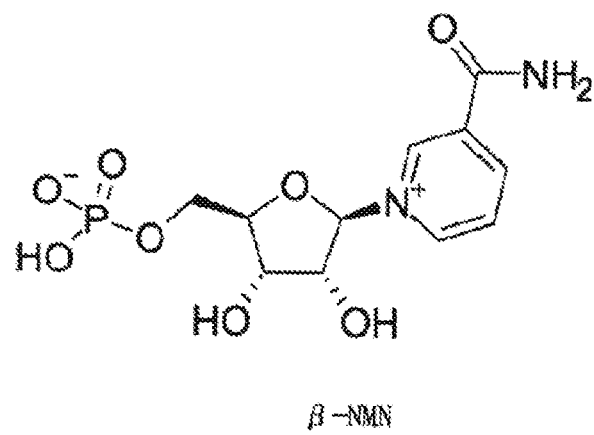
FIG. 17 shows the chemical structural formula of β-NMN.
Figure 18:
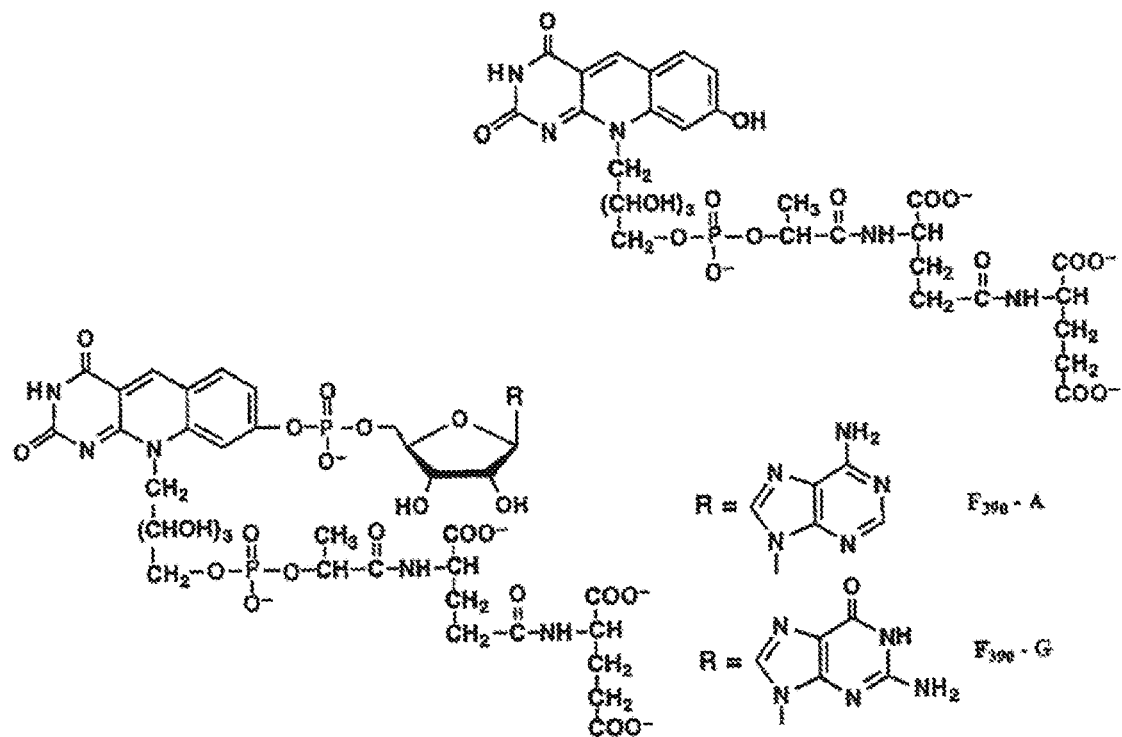
FIG. 18 shows the chemical structural formula of a coenzyme $F_{420}$.
Figure 19:
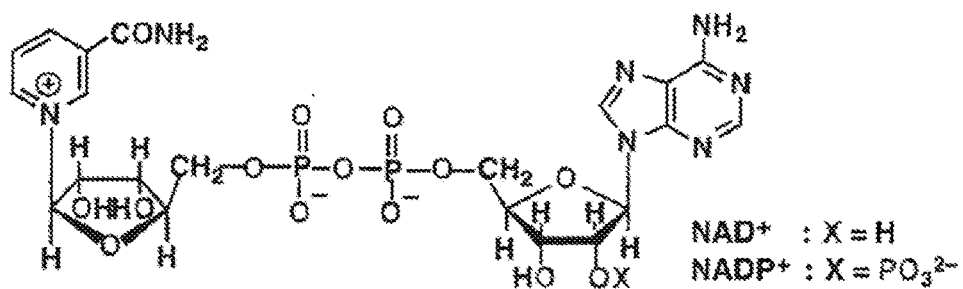
FIG. 19 shows the chemical structural formula of NAD(P)$^+$ and describes the redox reaction thereof.
Figure 19:
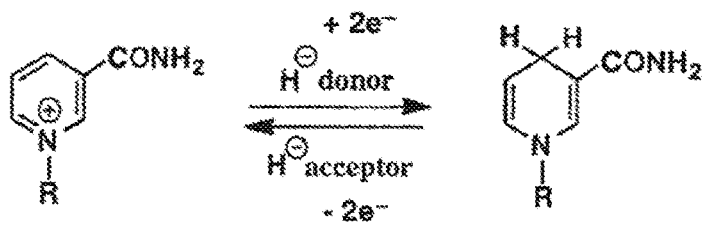
Figure 20:
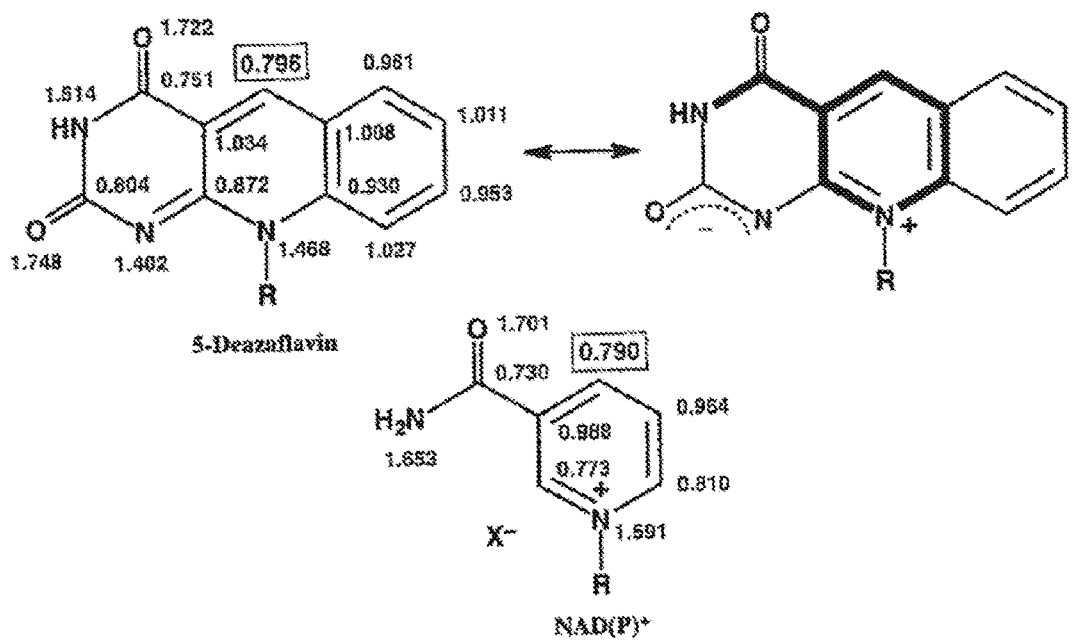
FIG. 20 shows electron densities determined by molecular orbital computational chemistry of the flavin rings of 5-deazaflavin and NAD(P)$^+$.
Figure 21:
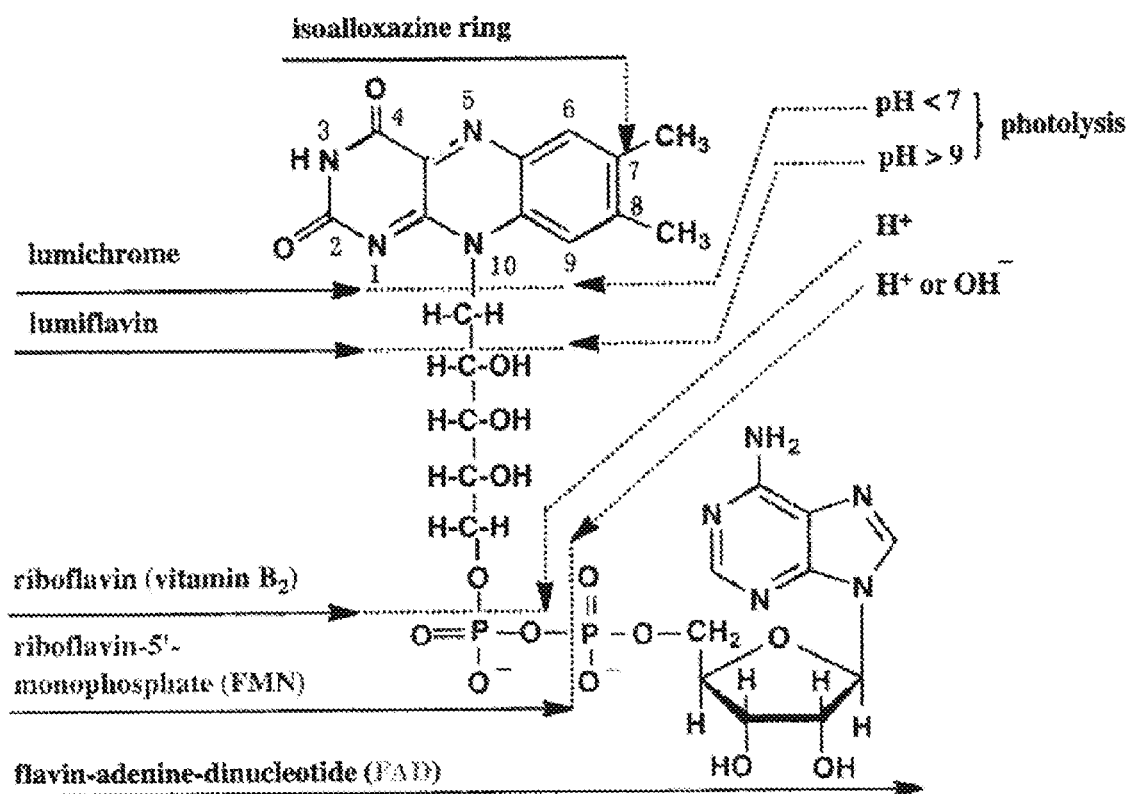
FIG. 21 is a view describing the similarity of the structure between NAD$^+$ and FAD.
Figures 22A, 22B:
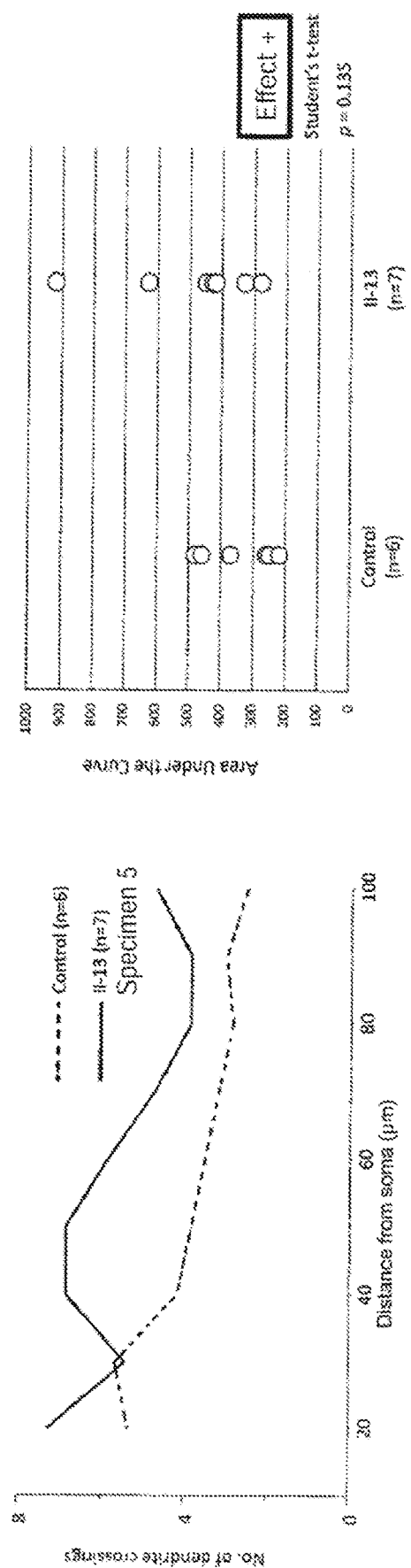
FIG. 22A and FIG. 22B show the quantification and test results of the number of branches of the hippocampal neuron dendrite after addition of Specimen 5.
Figures 23A, 23B:
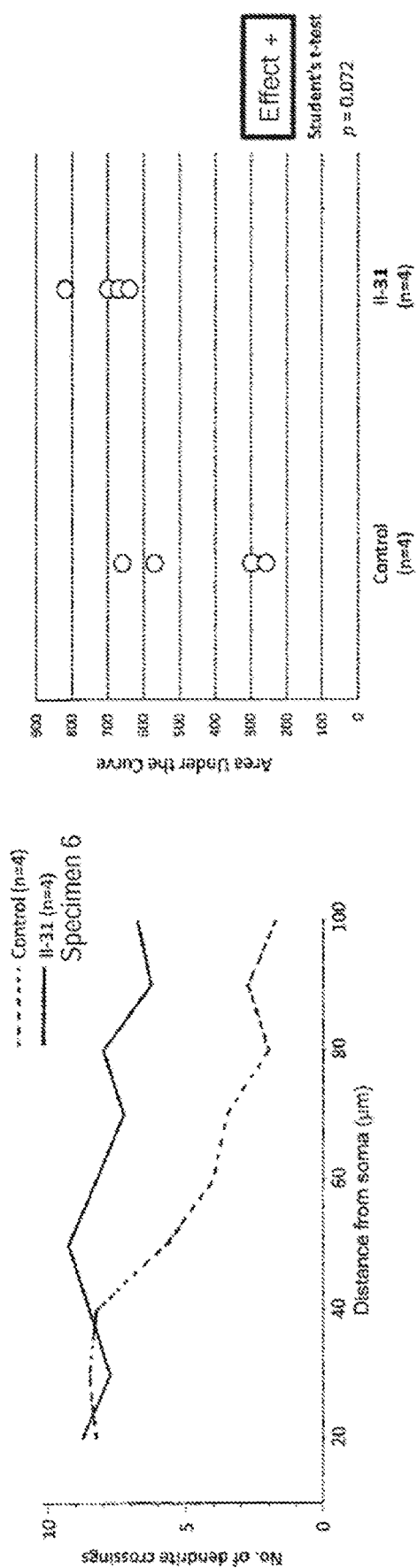
FIG. 23A and FIG. 23B show the quantification and test results of the number of branches of the hippocampal neuron dendrite after addition of Specimen 6.
Figures 24A, 24B:
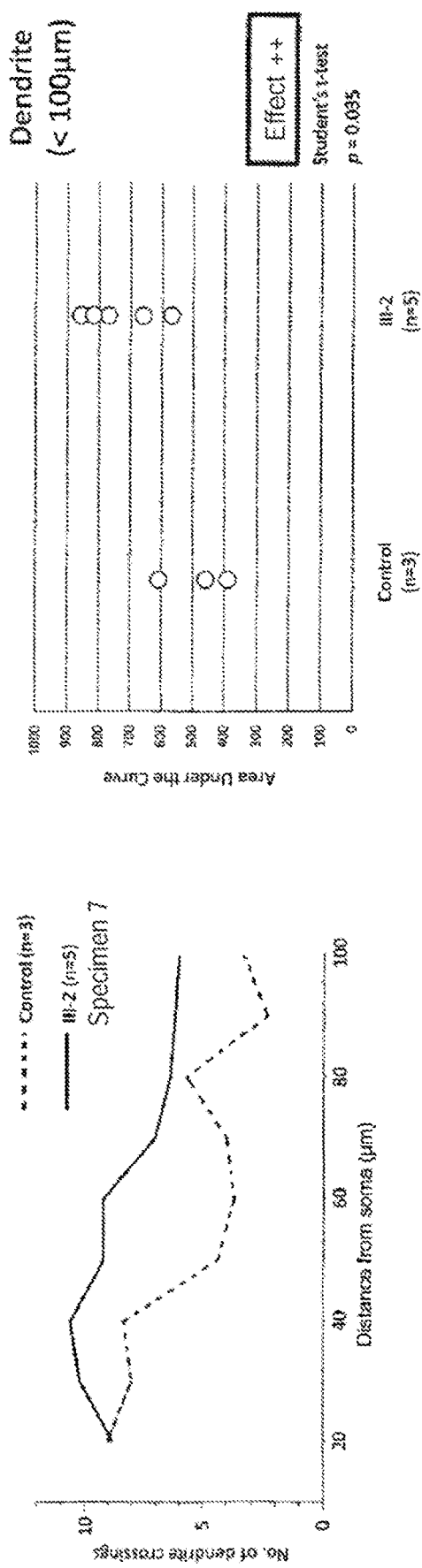
FIG. 24A and FIG. 24B show the quantification and test results of the number of branches of the hippocampal neuron dendrite after addition of Specimen 7.
Figures 25A, 25B:
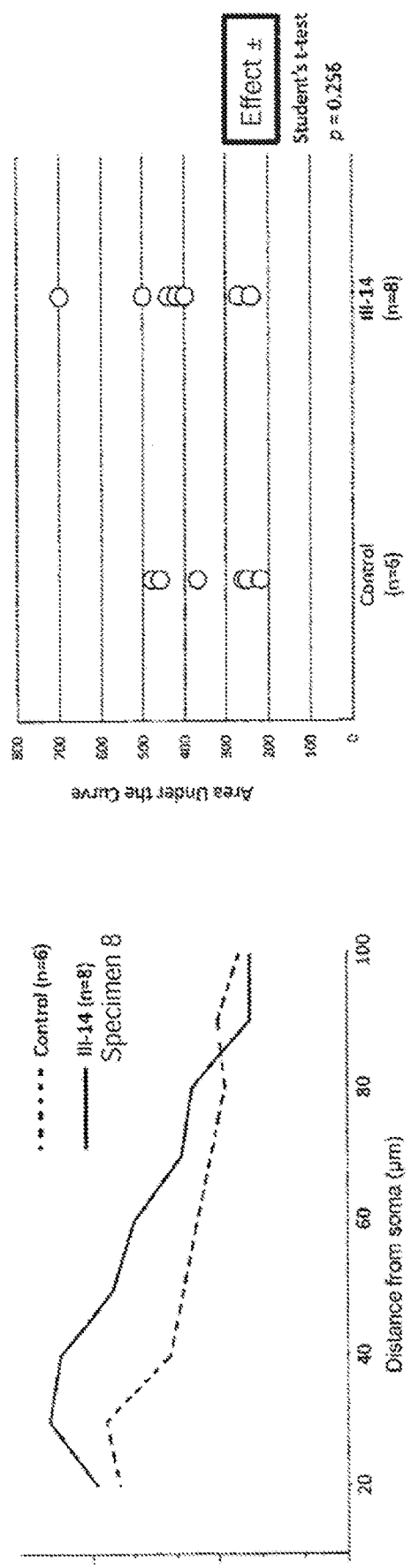
FIG. 25A and FIG. 25B show the quantification and test results of the number of branches of the hippocampal neuron dendrite after addition of Specimen 8.
Figure 26B:
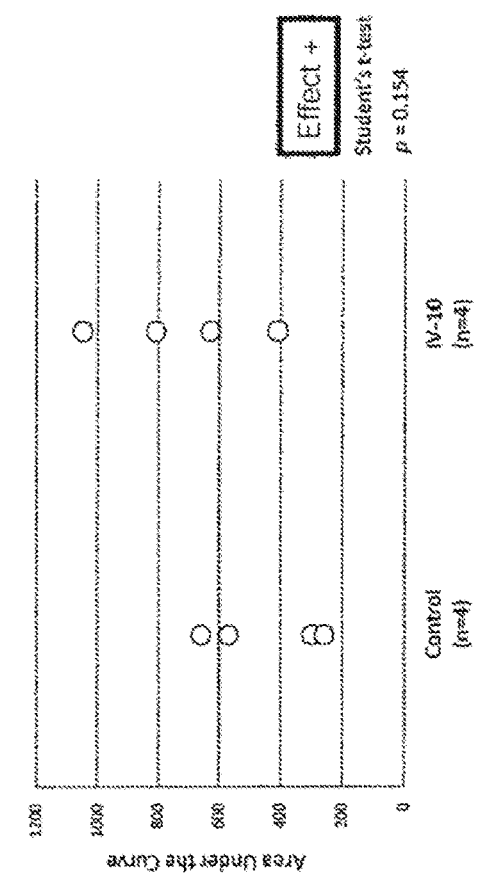
FIG. 26A and FIG. 26B show the quantification and test results of the number of branches of the hippocampal neuron dendrite after addition of Specimen 9.
Figure 26A:
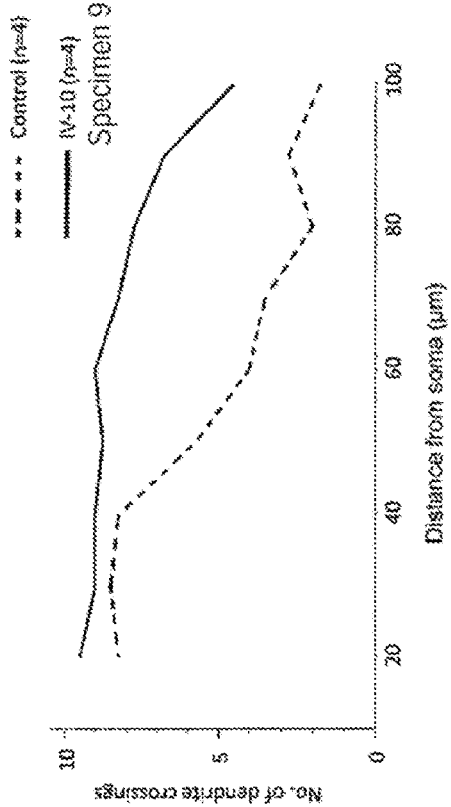
Figure 27B:
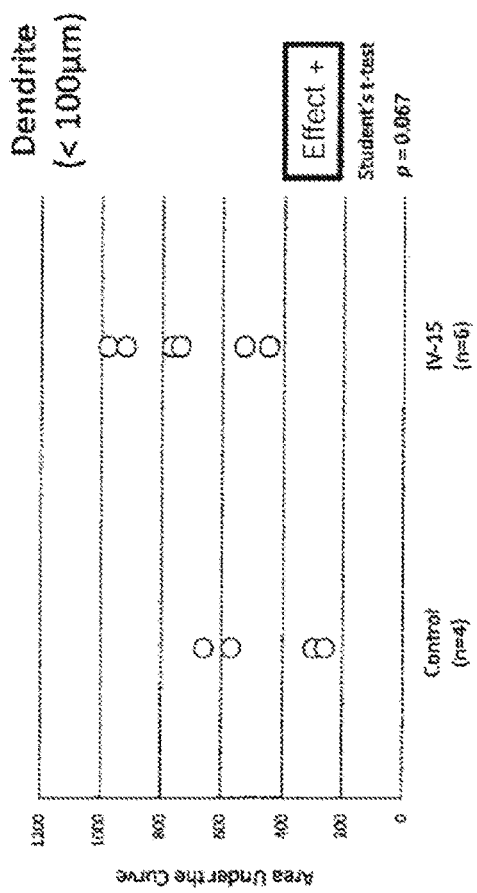
FIG. 27A and FIG. 27B show the quantification and test results of the number of branches of the hippocampal neuron dendrite after addition of Specimen 10.
Figure 27A:
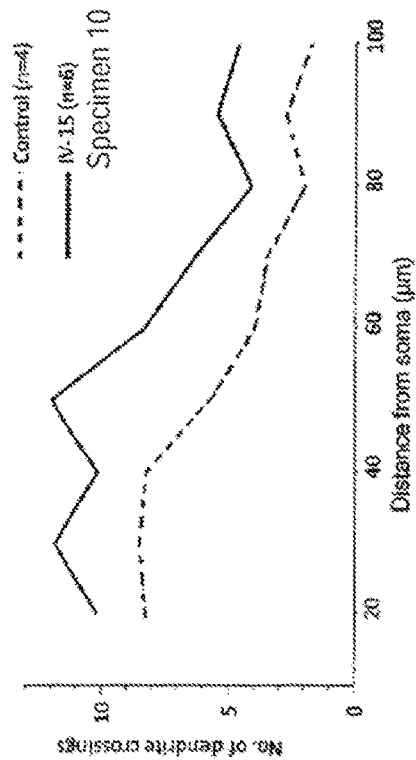
Figure 28B:
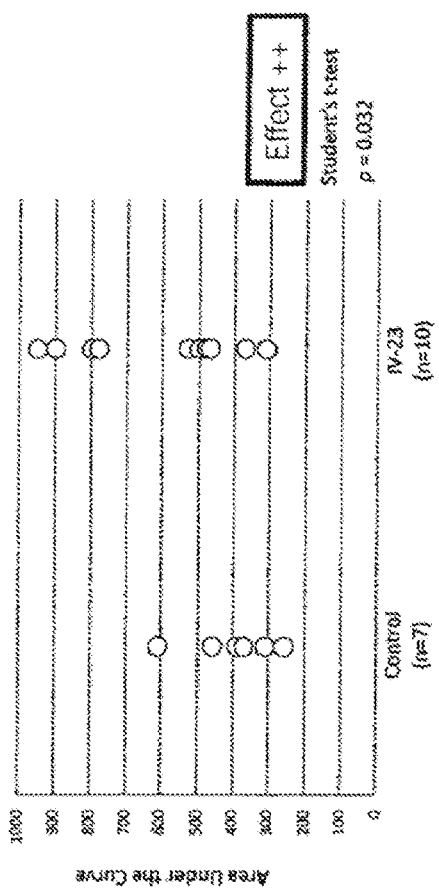
FIG. 28A and FIG. 28B show the quantification and test results of the number of branches of the hippocampal neuron dendrite after addition of Specimen 11.
Figure 28A:
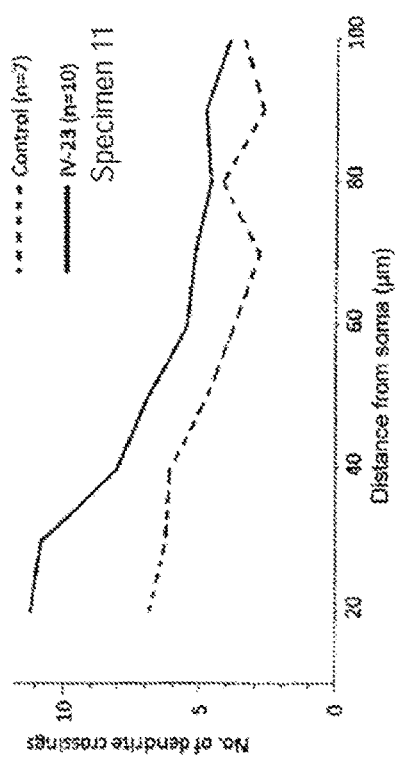

Specimen 4 ameliorates an ischemic decrease in exercise distance and exercise speed that occurs due to the cerebral ischemia of the rat (FIGS. 15 and 16). This effect can be observed both in hemorrhage day 1 and one week after hemorrhage.

The experimental results suggest that Specimen 4 contributes to prevention of ischemic damage of adult rat brain cells (indirect proof of ATP increase).

Next, tested was whether the addition of the following compounds as a specimen: Compounds No. II-12 (Specimen 5), II-31 (Specimen 6), III-2 (Specimen 7), III-14 (Specimen 8), IV-10 (Specimen 9), IV-15 (Specimen 10), and IV-23 (Specimen 11) significantly increased the number of branches of a hippocampus neuron dendrite or not.

Hippocampal neurons were collected from the juvenile (Day 0 after birth) ICR mouse brain and cultured on a culture dish.

Each specimen was added once to the cells in the initial growth stage (on culture day 1); the resulting cells were immunostained with a MAP2 antibody three days later (on culture day 4), and the number of branches of the dendrite was quantified.

The measurement was performed by drawing 20 µm to 100 µm concentric circles (not shown) at an interval of 10 µm with a soma as a center and counting the number of dendrites crossing the circles.

A line graph of the number of dendrite crossings counted for each distance from the soma was drawn and a Student's t-test, paired (t-test, two tailed distribution) was carried out using an area under the line graph (Area under the Curve: AUC).

When the number of cases of a specimen was sufficient, the test was performed while eliminating the maximum and minimum values. The concentrations of the specimens to be added were each 0.3 µM.

Whether the dendrite showed significant elongation or not was judged by a p-value calculated from a t-value as follows: when p<0.05, the dendrite showed significant elongation (effect++); when 0.05<p<0.2, the elongation was at distal or proximal site (effect+); and when p>0.2, there was no significant difference (effect: ±).

FIG. 22A to FIG. 28B show the results of adding Specimens 5 to 11, respectively and carrying out a quantitative test of the number of branches of the hippocampal neuron dendrite.

In these drawings, a shows the number of dendrite crossings relative to a distance from soma and b shows the test results obtained by comparison in AUC.

A solid line shows a specimen addition case and a dotted line shows a case where a specimen is not added (control). It is to be noted that n is the number of preparations.

As is apparent from the graphs, a statistically significant difference is recognized (p<0.05) only from Specimen 7 (III-2) and Specimen [[II]]11 (IV-23) and an effect on dendrite elongation is recognized also from the other specimens, that is, 5 (II-[[13]]12), 6 (II-31), 8 (III-[[2]]14), 9 (IV-10), and 10 (IV-15).

Next, Specimen 1 (TND1128) was selected and a comparison experiment in effect between it and β-NMN was made. In the experiment, compared and evaluated is their inhibitory effect on marked variations of cytoplasmic and mitochondrial $Ca^{2+}$ concentrations caused by exposure of mouse brain slice preparations to severe depolarization stimulation. A preliminary experiment by the present inventors and the like provided the finding that SIRT1 showed a significant increase in a nematode treated for 24 hours with Specimen 1 (TND1128), so that comparison was made to know whether a similar effect is achieved by β-NMN 24 hours after administration thereof.

Experimental Method

Formation of brain slice preparation and measurement of calcium concentration: Used was a whole brain half-cut preparation obtained by cutting a whole brain slice (300 µm) of a mouse (C57B/6NL), pretreated with Specimen 1 for 24 hours by subcutaneous administration, at a median line. The preparation was stored at room temperature in an artificial cerebrospinal fluid (ACSF) aerated with 95% $O_2$ and 5% $CO_2$ and was double stained with Xrhod-1/AM (Kd=700 µM) which would be incorporated selectively in mitochondria and fura-4F/AM (Kd=770 µM) which would remain in the cytoplasm. The resulting preparation was placed in a chamber provided on a stage of an inverted fluorescence microscope (Olympus IX71), covered with a piece of black cotton, fixed with a platinum ring, and refluxed (70 ml/hr) in ACSF aerated with 95% $O_2$ and 5% $CO_2$. A fluorescent image of the preparation was acquired using a 4× objective lens and respective images of the hippocampal ventral part and cerebral cortex temporal region were obtained in one screen. For the measurement of a mitochondrial calcium concentration, a change in intensity of red fluorescence (>600 nm) caused by excitation light at 580 nm was determined and for the measurement of a cytoplasmic calcium concentration, a ratio of fluorescence (>500 nm) between excitation at 360 nm and that at 380 nm was determined. A hippocampal CA1 site and a cerebral cortex were used as two regions of interest (ROI).

Drug Preparation Method and Administration Method

In water was dissolved β-NMN to give a 10 mg/kg, 30 mg/kg, or 100 mg/kg solution; Specimen 1 was dissolved in an alcohol to give a solution of 1 mg/ml and then the resulting solution was diluted with water to give a 0.01 mg/kg, 0.1 mg/kg or 1.0 mg/kg solution; and they were subcutaneously administered to mice 24 hours before the formation of the preparation (0.1 ml/10 g).

Efficacy Evaluation Method

In the present test, an operation of exposing the brain preparations formed from mice administered with two drugs having respective concentrations to isotonic 80 mM KCl-ACSF (artificial cerebrospinal fluid) for 5 minutes and then returning them in normal ACSF for 5 minutes was performed three successive times to give a severe calcium load to the preparations. Variations in cytoplasmic and mitochondrial calcium concentrations at that time were measured.

Experimental Results

Figure 29A:
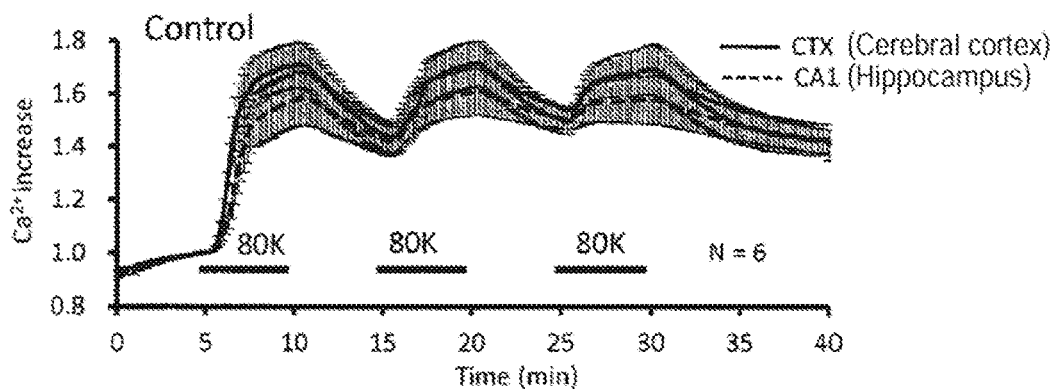
FIG. 29A to FIG. 29D show the analysis results of the mitochondrial $Ca^{2+}$ of the brain preparations of mice pretreated for 24 hours with β-NMN by subcutaneous administration. Preparations stained with Xrhod-1, a mitochondria-selective $Ca^{2+}$ indicator, were subjected to an operation including 80K ACSF exposure for 5 minutes three times repeatedly. The dose response relationship of β-NMN effecting the mitochondrial $Ca^{2+}$ variations at that time.
Figure 29B:
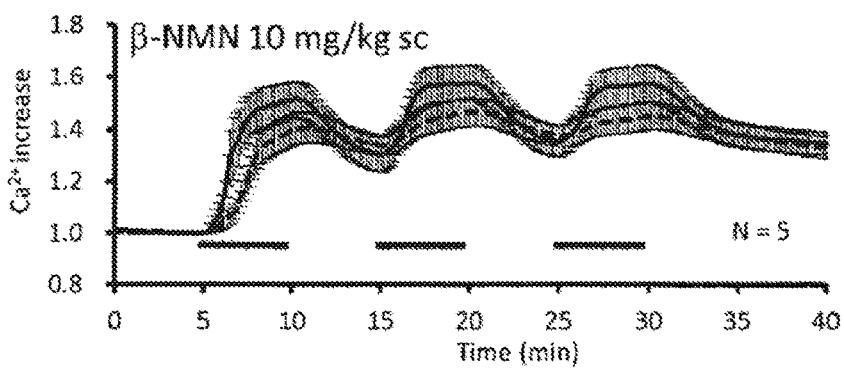
Figure 29C:
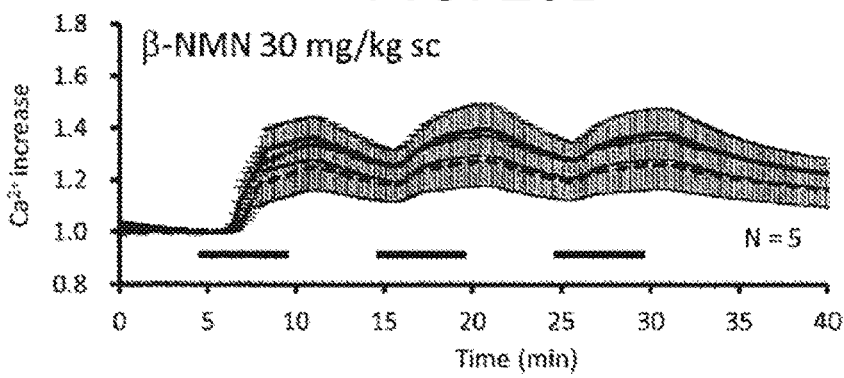
Figure 29D:
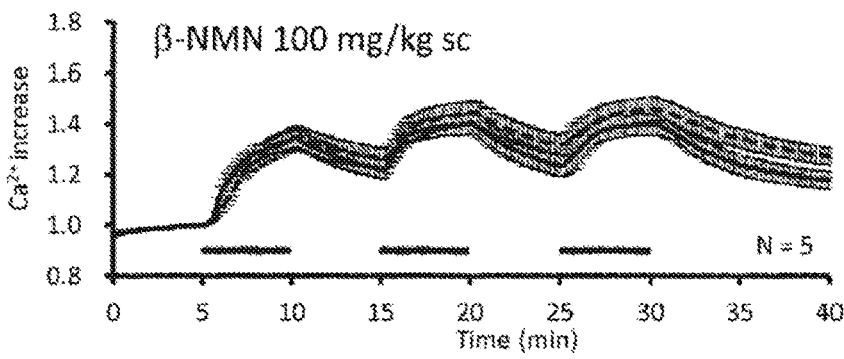
Figure 30A:
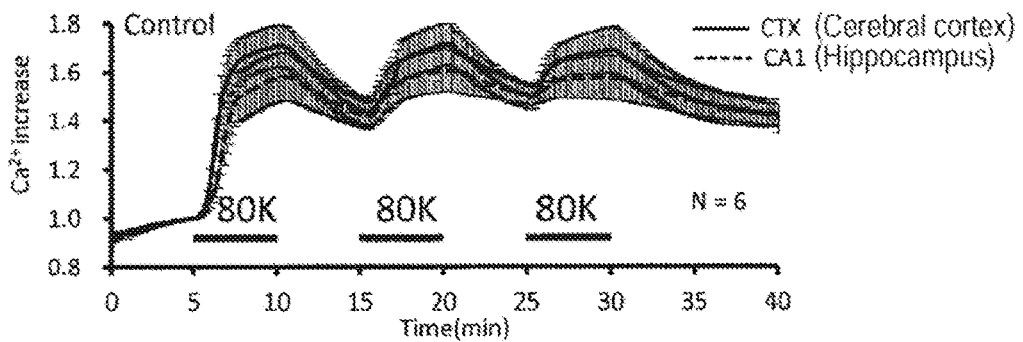
FIG. 30A to FIG. 30D show the analysis results of the mitochondrial $Ca^{2+}$ of brain preparations of mice pretreated for 24 hours with Specimen 1 (TND1128) by subcutaneous administration. Preparations stained with Xrhod-1, a mitochondria-selective $Ca^{2+}$ indicator, were subjected to an operation including 80K ACSF exposure for 5 minutes and washing for 5 minutes three times repeatedly, as in FIG. 29A to FIG. 29D. The dose response relationship of Specimen 1 (TND1128) effecting the mitochondrial $Ca^{2+}$ variations at that time
Figure 30B:
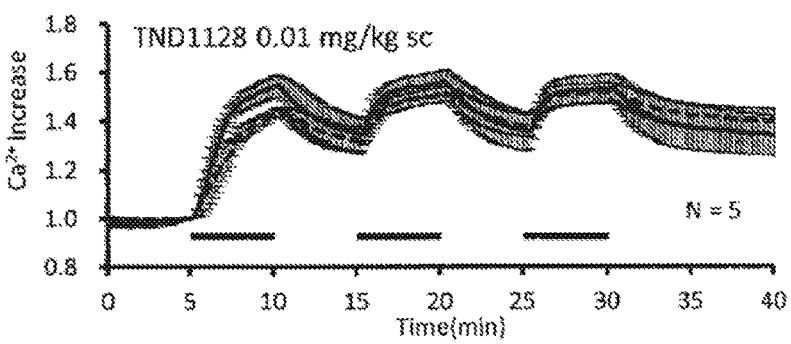
Figure 30C:
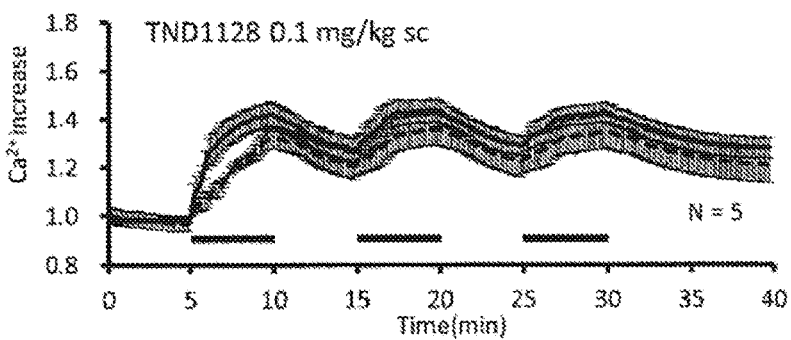
Figure 30D:
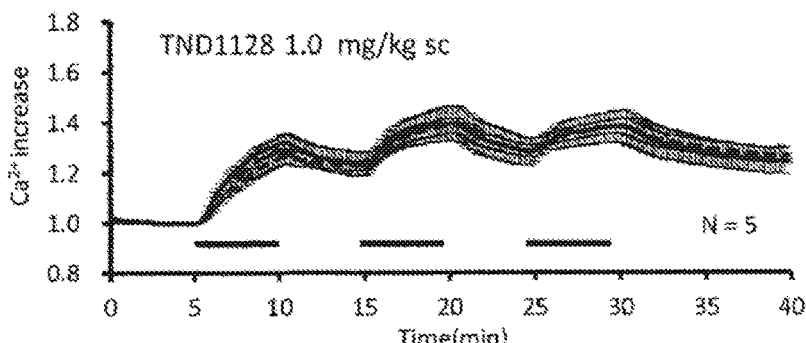
Figure 31A:
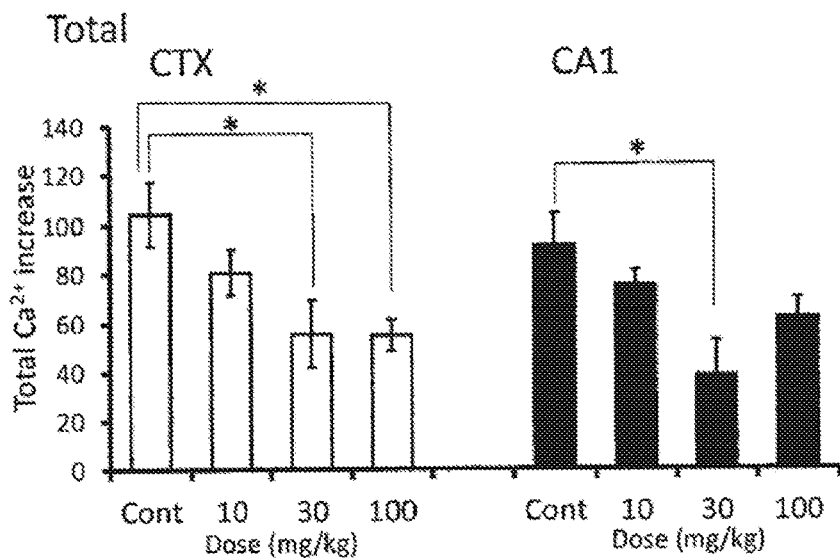
FIG. 31A to FIG. 31C show the dose response relationship of the protective effects of β-NMN on a mitochondrial $Ca^{2+}$ concentration when exposed to 80K ACSF. Statistic analysis of β-NMN effects on 80K induced mitochondrial $Ca^{2+}$ increase. The data in FIG. 29A to FIG. 29D are quantitatively shown (refer to FIG. 37).
Figure 31B:
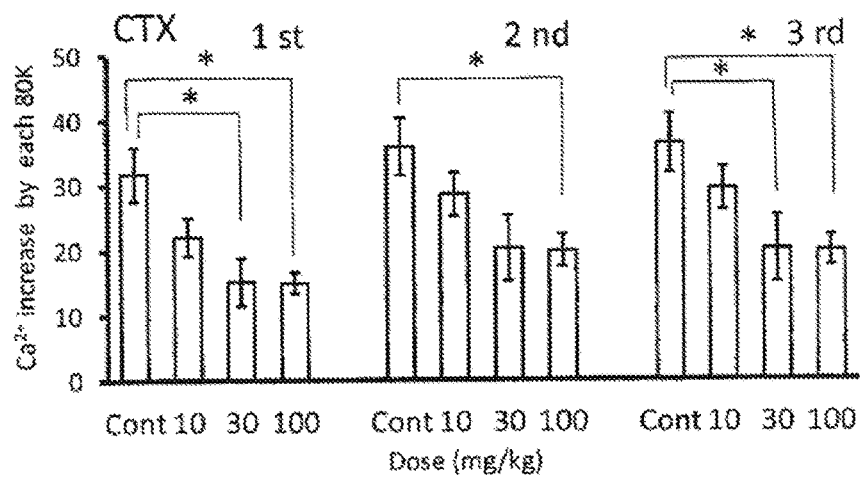
Figure 31C:
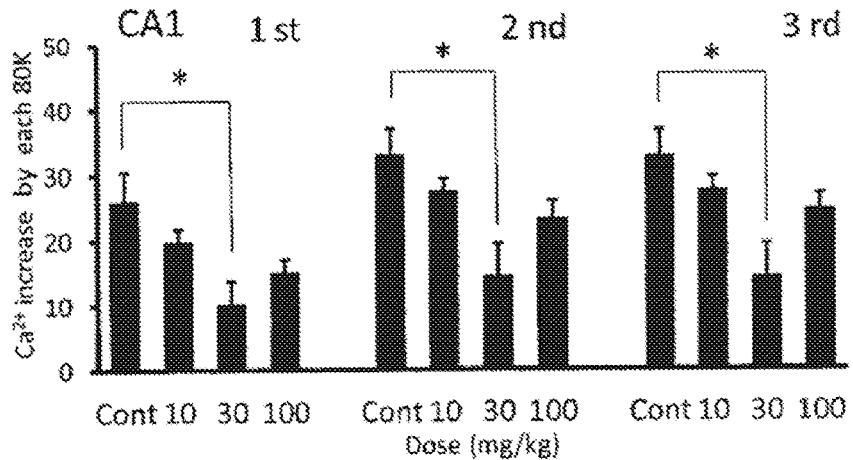
Figure 32A:
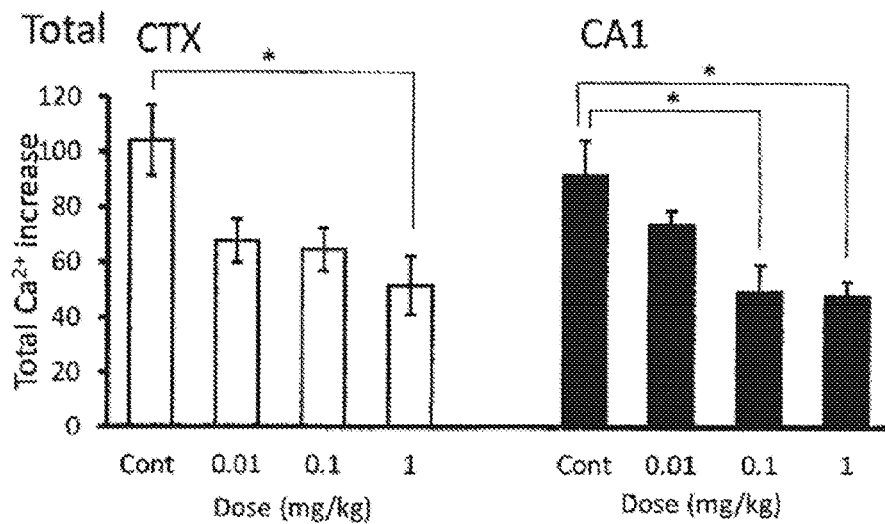
FIG. 32A to FIG. 32C show the dose response relationship of the protective effects of Specimen 1 (TND1128) on a mitochondrial Ca$^{2+}$ concentration when exposed to 80K ACSF. Dose response relationship to effects of 1128 on mitochondrial Ca$^{2+}$ increase induced by three times 80 K challenge. The data in FIG. [[29]]30A to FIG. 30D are quantitatively shown (refer to FIG. 37).
Figure 32B:
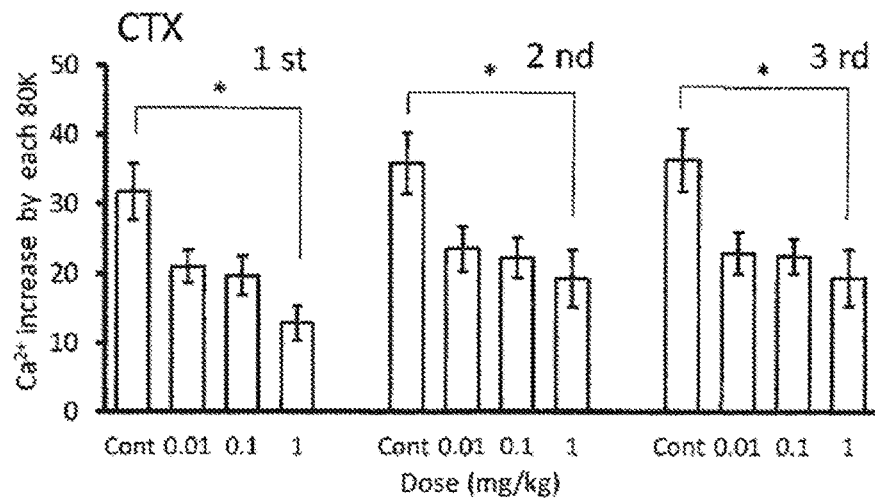
Figure 32C:
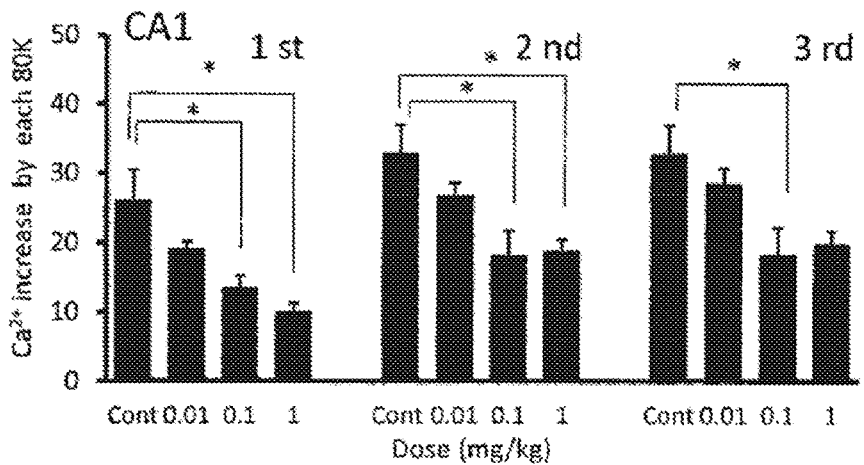
Figure 33A:
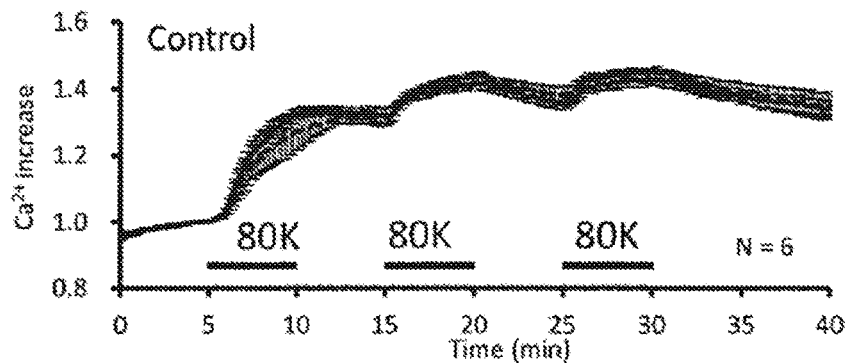
FIG. 33A to FIG. 33D show the analysis results of the cytoplasmic Ca$^{2+}$ of the mice brain preparations pretreated for 24 hours with β-NMN by subcutaneous administration. β-NMN was subcutaneously administered at each dose, whole brain slice preparations were formed after 24 hours of the administration, and the brain slice preparations were loaded with a Ca$^{2+}$ indicator Fura-4F capable of being retained in the cytoplasm. A time-dependent cytoplasmic Ca$^{2+}$ increase induced by three times 80K-ACSF stimulation obtained by exposing the brain preparations to excited lights of 360 nm and 380 nm and finding a ratio of fluorescence intensity (F360 and F380) of a bluish green color (>500 nm) at every 10 seconds with the passage of time.
Figure 33B:
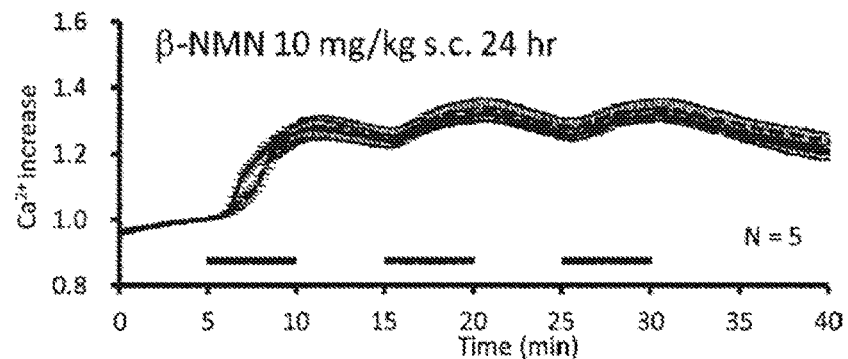
Figure 33C:
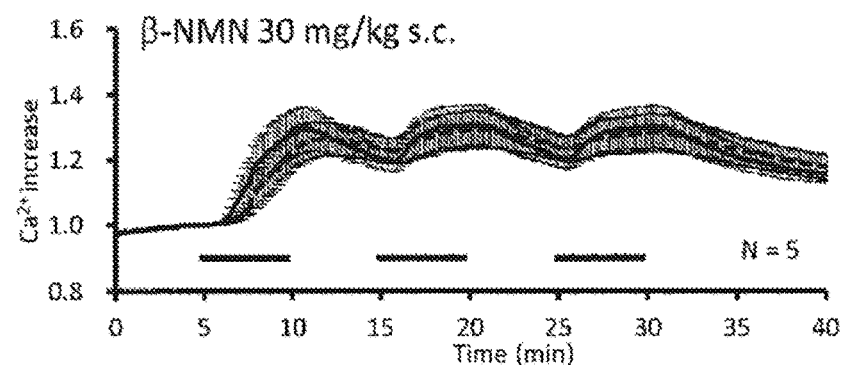
Figure 33D:
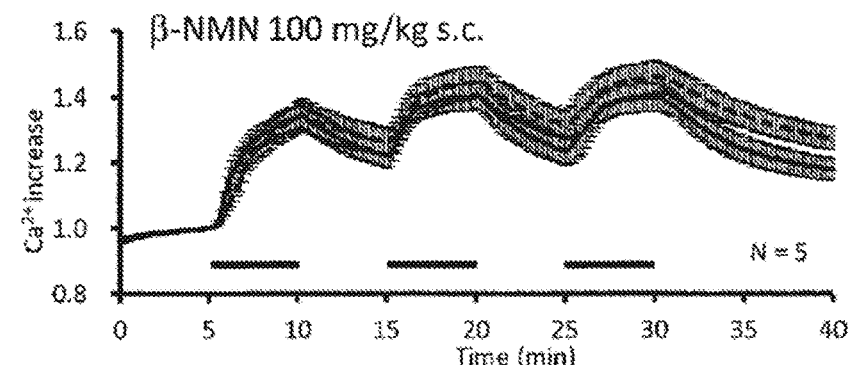
Figure 34A:
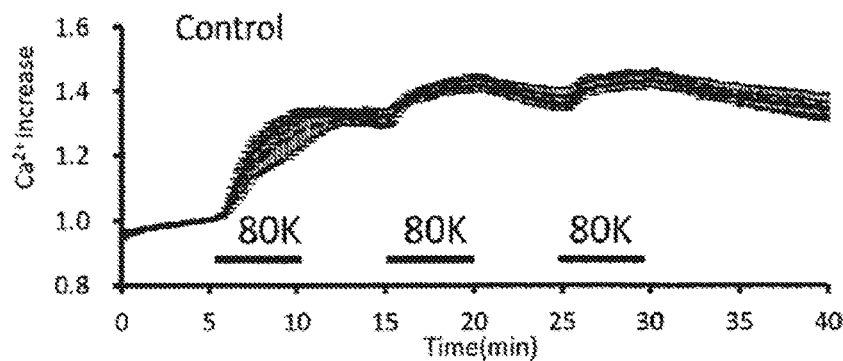
FIG. 34A to FIG. 34D show the analysis results of the cytoplasmic Ca$^{2+}$ of the mice brain preparations pretreated for 24 hours with Specimen 1 (TND1128) by subcutaneous administration. Preparations loaded with Fura-4F, a cytoplasm-selective Ca$^{2+}$ indicator, were subjected to an operation including 80K ACSF exposure for 5 minutes three times repeatedly, as in FIG. 29A to FIG. 29D. The dose response relationship of TND1128 effecting the cytoplasmic Ca$^{2+}$ variations at that time.
Figure 34B:
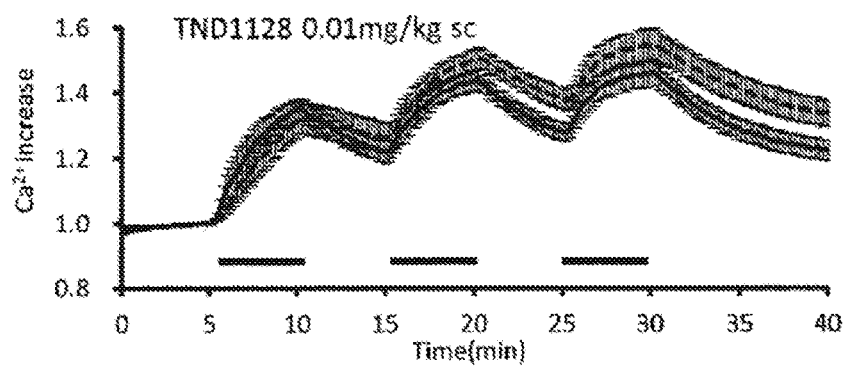
Figure 34C:
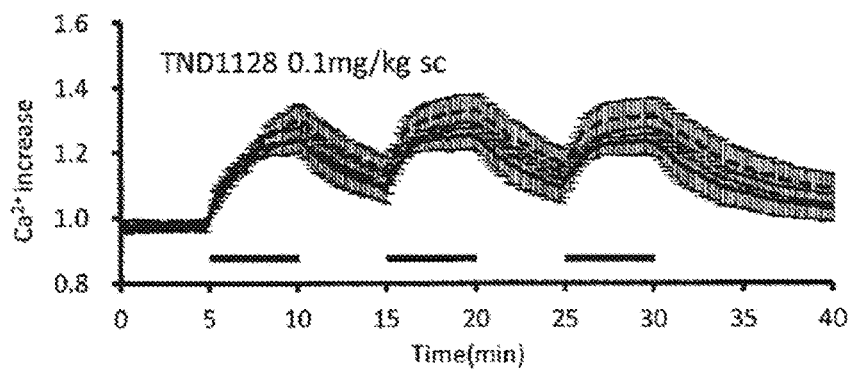
Figure 34D:
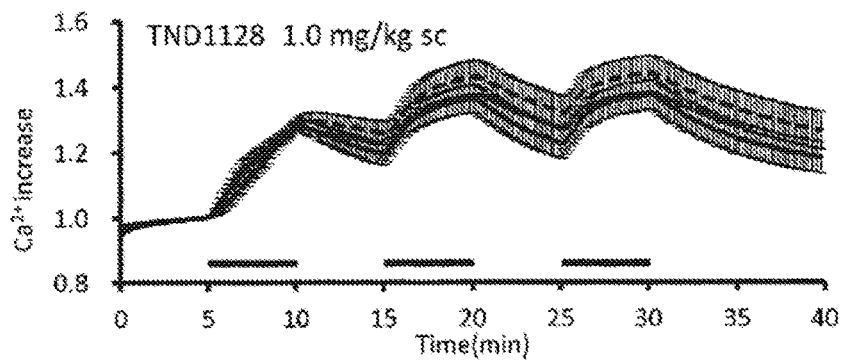
Figure 35A:
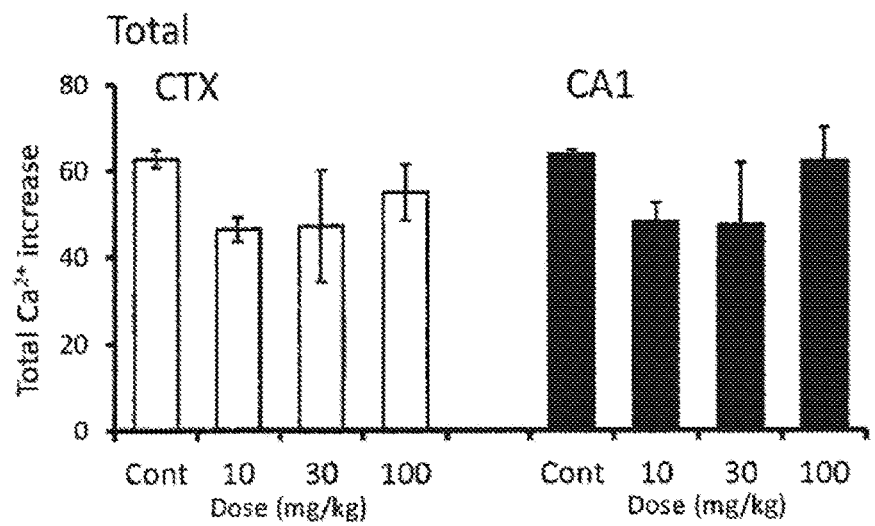
FIG. 35A to FIG. 35C show the dose response relationship of the protective effects of β-NMN on the cytoplasmic Ca$^{2+}$ concentration when exposed to 80K ACSF. Statistic analysis of β-NMN effects on 80K induced cytosolic Ca$^{2+}$ increase. The data in FIG. 33 A to FIG. 33D are quantitatively shown (refer to FIG. 37).
Figure 35B:
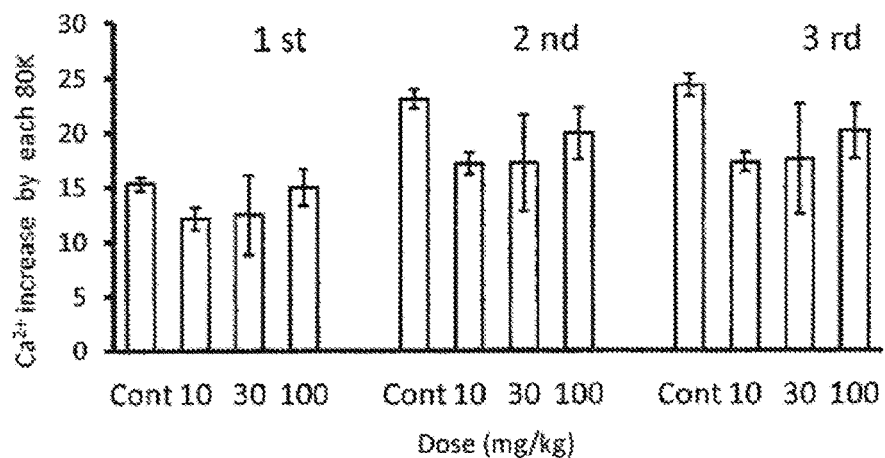
Figure 35C:
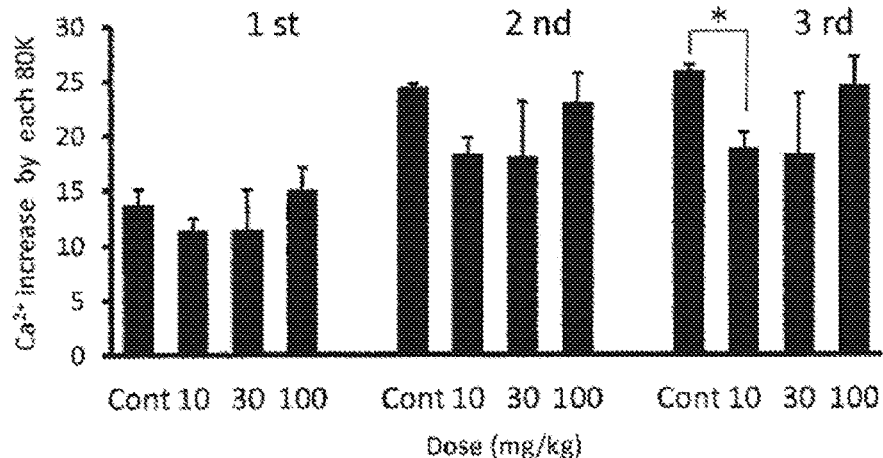
Figure 36A:
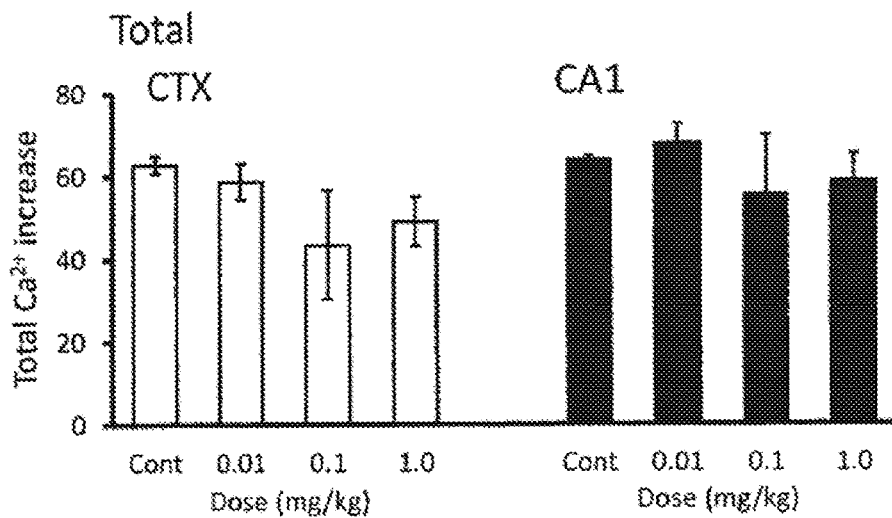
FIG. 36A to FIG. 36C show the dose response relationship of the protective effects of Specimen 1 (TND1128) on the cytoplasmic Ca$^{2+}$ concentration when exposed to 80K ACSF. Dose response relationship to effects of 1128 on cytosolic Ca$^{2+}$ increase induced by three times 80 K challenge. The data in FIG. 34 A to FIG. 34D are quantitatively shown (refer to FIG. 37).
Figure 36B:
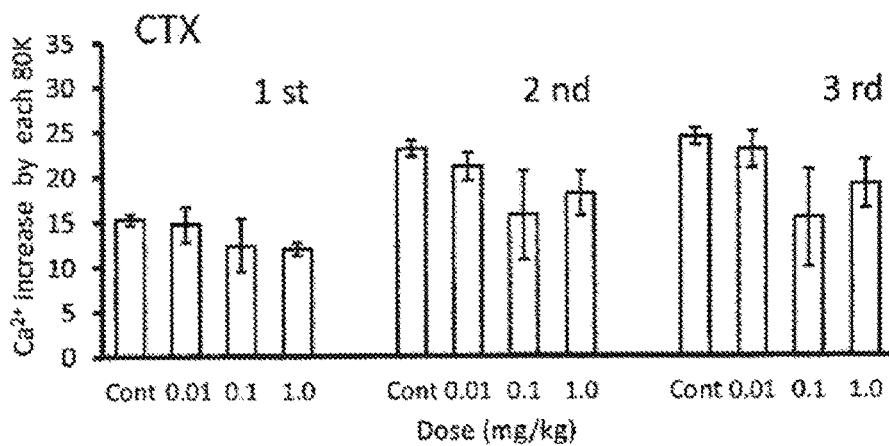
Figure 36C:
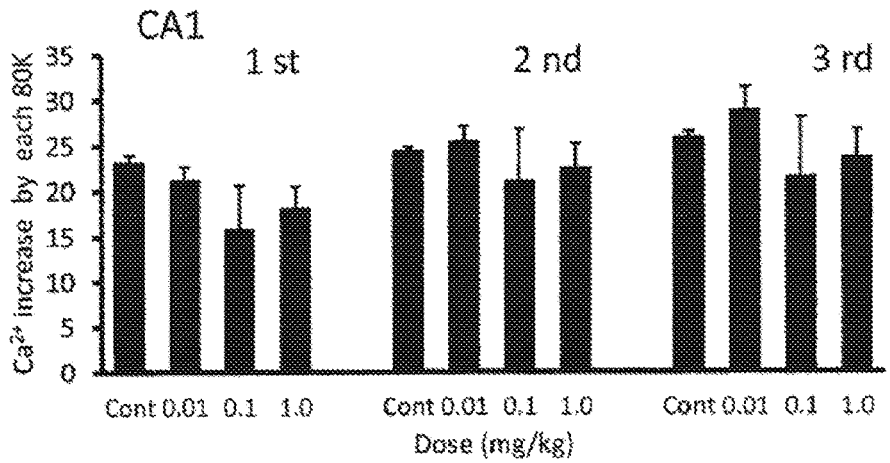

Effects of β-NMN and Specimen 1 (TND1128) on variations of mitochondrial calcium concentration FIG. 29A to FIG. 29D show variations of a mitochondrial $Ca^{2+}$ concentration when the preparations formed from mice pretreated for 24 hours by subcutaneous administration with β-NMN (FIG. 29A: 0 (control) (n=6), FIG. 29B: 10 (n=5), FIG. 29C: 30 (n=5), and FIG. 29D: 100 mg/kg (n=5)) were exposed to 80K ACSF three times. Similarly, FIG. 30A to FIG. 30D show variations of a mitochondrial calcium concentration when the brain preparations of mice administered with Specimen 1 (TND1128) (FIG. 30A: 0 (control) (n=6), FIG. 30B: 0.01 (n=5), FIG. 30C: 0.1 (n=5), and FIG. 30D: 1.0 mg/kg (n=5) s.c.) were exposed to 80K ACSF. The response of the preparations obtained from individuals treated with both drugs at respective doses is normalized (normalized) with fluorescence intensity at the first 80K administration time as a standard and a time average of the cytoplasmic or mitochondrial $Ca^{2+}$ concentration and a standard deviation thereof are shown. It is obvious from these FIG. 29A to FIG. 30D that these drugs dose-dependently suppress a mitochondrial $Ca^{2+}$ increase within a range of their doses.

Figure 37:
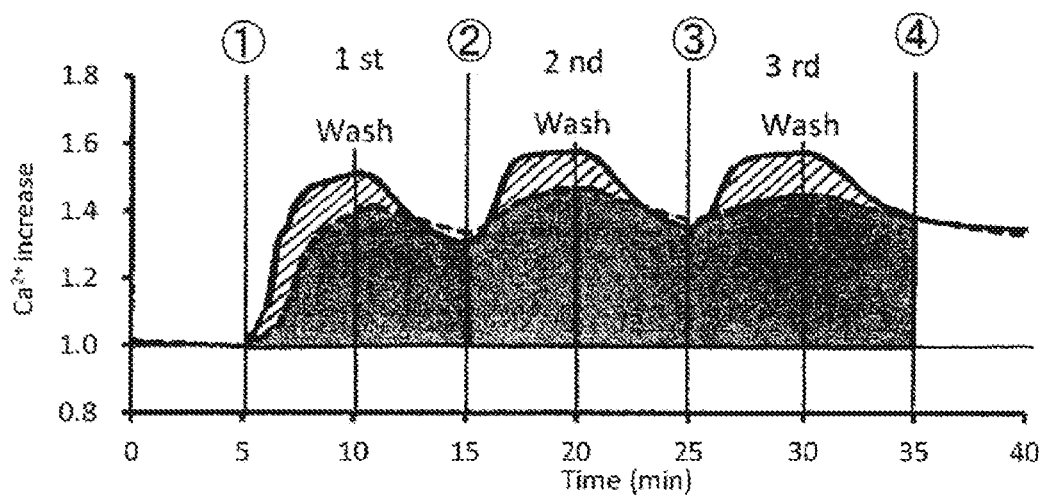
FIG. 37 is a drawing for describing a quantification method of a mitochondrial or cytoplasmic Ca$^{2+}$ increase amount when exposed to 80K three successive times. Quantification of Ca$^{2+}$ increase. Quantification method of Ca$^{2+}$ increase amount in mitochondria or cytoplasm when exposed to 80K three successive times. All the data were normalized with the value upon first administration as a standard. 1st: from first 80 ACSF administration (1) to second administration (2). 2nd: from second 80 ACSF administration (2) to third administration (3). 3rd: from third 80 ACSF administration (3) to fourth administration (4). Total response: 1st+2nd+3rd. How to determine AUC.Area under the curve(AUC) is determined as a value obtained by subtracting the measured number (60 for 10 minutes and 180 in total) from the total Ca$_{2+}$ response normalized every 10 seconds.

FIG. 31A to FIG. 32C show the quantification results of the effects of β-NMN and Specimen 1 (TND1128) at each concentration. In FIG. 31A to FIG. 32C, FIG. 31A and FIG. 32A show the results of calculating a mitochondrial calcium concentration, as AUC (Area under the curve), for 35 minutes from 5 minutes after starting of the experiment by administration to three times exposure to 80K-ACSF and 5-minute washing (refer to FIG. 37). FIG. 31B, FIG. 31C, FIG. 32B and FIG. 32C show the drug effects on 5-minute 80K administration and 5-minute subsequent washing (1st: from 5 minutes to 15 minutes, 2nd: from 15 minutes to 25 minutes, and 3rd: from 25 minutes to 35 minutes) in the cerebral cortex (CTX) and the hippocampus (CA1), respectively (refer to FIG. 37). A significant difference test was performed using Tukey's method. Within the dose range thus studied, a dose response relationship of β-NMN and TND1128 was observed.

Effects of β-NMN and Specimen 1 (TND1128) on variations in cytoplasmic calcium concentration FIG. 33A to FIG. 34D show the effects of β-NMN and Specimen 1 (TND1128) on cytoplasmic calcium variations at the time of administration of 80K ACSF three successive times. In the Control response shown in FIG. 33A to FIG. 34D, the response recovery is small at each 80K-ACSF administration time and the response of a calcium indicator seems to reach its peak. An intracellular calcium concentration indicator fura-4F used in the test has a $Ca^{2+}$ chelating ability (Kd) of 770 nM and it is presumed to be able to respond to an expected drastic increase in intracellular calcium concentration, so that it can be presumed that variations of the intracellular $Ca^{2+}$ in the control group show that the $Ca^{2+}$ pump of the cytoplasmic membrane reaches its functional limit. In the preparations obtained from mice treated with 30 mg/kg or 100 mg/kg of β-NMN or the preparations obtained from mice treated with from 0.01 mg/kg to 1.0 mg/kg of Specimen 1 (TND1128), variations of the cytoplasmic calcium concentration at each administration show similar recovery. As can be observed from FIG. 35A to FIG. 36C, however, when those values were quantified by a method similar to that for mitochondria, a significant difference was not observed at concentrations other than that of the group administered with 10 mg/kg of β-NMN.

Effecting Manner of Both Drugs in Terms of Effective Concentration

Both drugs show a similar level of mitochondrial $Ca^{2+}$ concentration suppressing effect. Judging from the effective concentration, the effect of Specimen 1 (TND1128) was 100 times stronger. Non-Patent Document 6 has reported that $NAD^+$ reached a peak 30 minutes after administration of β-NMN and the blood level of the administered NMN decreases correspondingly, suggesting the possibility of the administered NMN becoming a matrix for $NAD^+$ biosynthesis. The effective amount of Specimen 1 (TND1128) used in the present experiment was as trace as 1.0 mg/kg or less and it cannot be considered as a raw material for the biosynthesis, different from β-NMN. Even if the biosynthesis amount of $NAD^+$ increases in an oxidative energy acquiring process of mitochondria finally, it should be considered that a significant mitochondrial function stabilizing effect observed 24 hours after the administration owes to an increase in $NAD^+$ caused by expression promotion of a sirtuin gene group. Since in the present research, 24-hr pretreatment with β-NMN induces significant mitochondrial protective function, it should be considered that the effect of β-NMN does not result simply from supply of it as a substrate for $NAD^+$ but is mediated by the effect on the sirtuin gene group.

On the other hand, β-NMN and Specimen 1 (TND1128) each showed no significant effect on a drastic increase in cytoplasmic $Ca^{2+}$ concentration caused by 80K-ACSF. Effects of 100 mg/kg of β-NMN and 1 mg/kg of Specimen 1 (TND1128) on the variations of a mitochondrial $Ca^{2+}$ concentration shown in FIG. 29A to FIG. 30D and effects of β-NMN and Specimen 1 (TND1128) on the variations of a cytoplasmic $Ca^{2+}$ concentration shown in FIG. 33A to FIG. 34D have revealed that irrespective of severe stimulation of 80K-ACSF, the preparations can maintain a markedly stable physiological response. If this can be reproduced in the human brain, a strong brain protective effect can be expected.

Pharmacological effects of synthetic sirtuin activating drugs such as resveratrol, a component of red wine, and SRT1720, a derivative thereof, have already been reported (Non-Patent Document 8), but there is not report actually referring to the effectiveness on the mitochondrial function of subcutaneously administered mouse brain as in the present experiment.

As is apparent from the above description, Specimen 1 (TND1128) is a highly hydrophobic and stable compound, which is a large advantage over β-NMN.

By making use of this advantage, this compound can be prepared into an external medicine and can be used for activating the damaged hair root, thereby treating silver hair or baldness or for rejuvenating flabby skin cells. Further, the compound is also expected to have an effect on the brain after being percutaneously absorbed.

The above experimental results show that the 5-deazaflavin compounds represented by the formulas (I) to (IV) activate intracellular ATP production.

The invention claimed is:
1. Use of a deazaflavino-testosterone compound represented by the following formula (III):

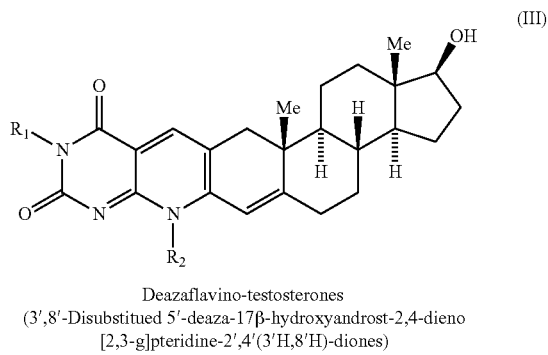

Deazaflavino-testosterones
(3',8'-Disubstitued 5'-deaza-17β-hydroxyandrost-2,4-dieno
[2,3-g]pteridine-2',4'(3'H,8'H)-diones)

wherein, $R_1$ represents a hydrogen atom, an alkyl group, a halogen-substituted alkyl group, a carboxy-substituted alkyl group, a phenyl group, or a phenyl group substituted by one of a halogen atom, a lower alkyl group, or a lower alkoxy group and $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group for activating intracellular ATP production, the use comprising introducing said deazaflavino-testosterone compound to a human-derived neuron cells, wherein said deazaflavino-testosterone compound is used as a coenzyme factor effective for activating intracellular ATP production.

2. Use of a deazaflavino-cholesterol compound represented by the following formula (IV):

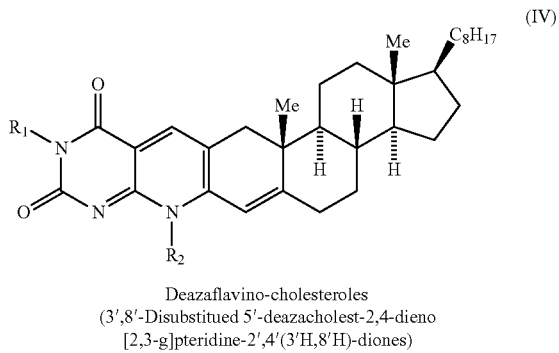

Deazaflavino-cholesteroles
(3′,8′-Disubstitued 5′-deazacholest-2,4-dieno
[2,3-g]pteridine-2′,4′(3′H,8′H)-diones)

wherein, $R_1$ represents a hydrogen atom, an alkyl group, a halogen-substituted alkyl group, a carboxy-substituted alkyl group, a phenyl group, or a phenyl group substituted by one of a halogen atom, a lower alkyl group, or a lower alkoxy group and $R_2$ represents an alkyl group, a cycloalkyl group, a phenyl-substituted lower alkyl group, a phenyl group, a phenyl group substituted by one of a halogen atom, a lower alkyl group, or a lower alkoxy group, or a lower alkyl disubstituted phenyl group for activating intracellular ATP production, the use comprising introducing said deazaflavino-cholesterol compound to a human-derived neuron cells, wherein said deazaflavino-cholesterol compound is used as a coenzyme factor effective for activating intracellular ATP production.

* * * * *